United States Patent
Smid et al.

(10) Patent No.: US 9,096,612 B2
(45) Date of Patent: Aug. 4, 2015

(54) FUSED HETEROCYCLIC DERIVATIVES AS S1P MODULATORS

(71) Applicants: Abbvie B.V., Hoofddorp (NL); AbbVie, Inc., North Chicago, IL (US)

(72) Inventors: Pieter Smid, Hoofddorp (NL); Wouter I. Iwema Bakker, Hoofddorp (NL); Hein K. A. C. Coolen, Hoofddorp (NL); Leonardus A. J. M. Sliedregt, Hoofddorp (NL); Maria J. P. van Dongen, Hoofddorp (NL); Jacobus A. J. den Hartog, Hoofddorp (NL); Adrian Hobson, Worcester, MA (US)

(73) Assignees: AbbVie B.V., Hoofddorp (NL); AbbVie Inc., North Chicago, IL (US)

( * ) Notice: Subject to any disclaimer, the term of this patent is extended or adjusted under 35 U.S.C. 154(b) by 0 days.

(21) Appl. No.: 14/019,236

(22) Filed: Sep. 5, 2013

(65) Prior Publication Data

US 2014/0066433 A1    Mar. 6, 2014

Related U.S. Application Data

(62) Division of application No. 13/808,908, filed as application No. PCT/EP2011/061586 on Jul. 8, 2011, now Pat. No. 8,796,262.

(60) Provisional application No. 61/362,784, filed on Jul. 9, 2010, provisional application No. 61/446,541, filed on Feb. 25, 2011.

(30) Foreign Application Priority Data

Jul. 9, 2010   (EP) .................................... 10169107
Feb. 25, 2011  (EP) .................................... 11156007

(51) Int. Cl.
| | |
|---|---|
| *A01N 43/00* | (2006.01) |
| *A01N 43/46* | (2006.01) |
| *C07D 513/04* | (2006.01) |
| *C07D 487/04* | (2006.01) |
| *C07D 491/04* | (2006.01) |
| *C07D 498/04* | (2006.01) |
| *C07D 471/04* | (2006.01) |
| *C07D 491/048* | (2006.01) |
| *C07D 495/04* | (2006.01) |

(52) U.S. Cl.
CPC ............ *C07D 513/04* (2013.01); *C07D 471/04* (2013.01); *C07D 487/04* (2013.01); *C07D 491/04* (2013.01); *C07D 491/048* (2013.01); *C07D 495/04* (2013.01); *C07D 498/04* (2013.01)

(58) Field of Classification Search
USPC .......... 514/215, 301, 302, 303, 412; 540/593; 546/114, 115, 118, 453
See application file for complete search history.

(56) References Cited

U.S. PATENT DOCUMENTS

| | | |
|---|---|---|
| 2009/0023797 A1 | 1/2009 | Azzaoui et al. |
| 2009/0192154 A1 | 7/2009 | Maekawara et al. |

FOREIGN PATENT DOCUMENTS

| | | |
|---|---|---|
| EP | 2364976 | 9/2011 |
| SU | 1069387 | 11/1985 |
| SU | 1069387 A1 | 11/1985 |
| WO | 2008/012010 | 1/2008 |
| WO | 2008/012010 A1 | 1/2008 |

OTHER PUBLICATIONS

British Journal of Clinical Practice, Nov./Dec. 1994, vol. 48, No. 6, pp. 327-330.*
Jo et al, Kidney Int. Jun. 2008; 73(11): 1220-1230.*
Deary et al, Br Med Bull (2009) 92 (1): 135-152; Jo et al, Kidney Int. Jun. 2008; 73(11).*
Adlard et al, Aging cell (2014) 13, pp. 351-359.*
Yutilov et al., "Synthesis and antiviral activity of spinaceamine derivatives," XP-002613847 (1989).
Yutilov et al., "Synthesis and biological activity of N-4-beta-hydroxyethylspinacemines," XP-002613848 (1989).
International Search Report issued in International Patent Application No. PCT/EP2011/061586 (2011).
Yutilov et al., "Synthesis and antiviral activity of spinaceamine derivatives," Khimiko-Farnriatsevticheskii Zhurnal (1989) 23(1):56-59, XP002613847.
Yutilov et al., "Synthesis and biological activity of N-4-beta-hydroxyethylspinaceamines," Khimiko-Farmatsevticheskii Zhurnal (1989) 23(2):160-163, XP002613848.
International Search Report for Application No. PCT/EP2011/061586 mailed Aug. 25, 2011.
Written Opinion for Application No. PCT/EP2011/061586 dated Jan. 12, 2012.

* cited by examiner

Primary Examiner — Wu-Cheng Winston Shen
Assistant Examiner — Jean Cornet
(74) Attorney, Agent, or Firm — Lisa V. Mueller; Michael Best & Friedrich LLP

(57) ABSTRACT

The present invention relates to a fused heterocyclic derivative of the formula (I) The variables R1-R4, z, A, Q, X and Y are as defined in the claims. The following heterocycles are exemplified sub-structures of formula (I): The compounds of formula (I) are modulators of the S1P receptor (Sphingosine-1-phosphate receptor), More specifically, they are agonists of S1P5. The compounds have therapeutic use in treatment of cognitive disorders, age-relate cognitive decline and dementia.

(I)

-continued
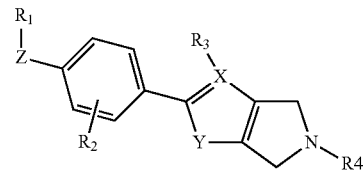
A
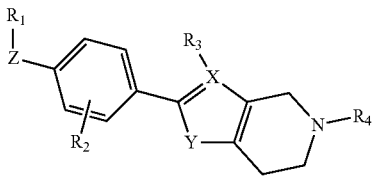
B
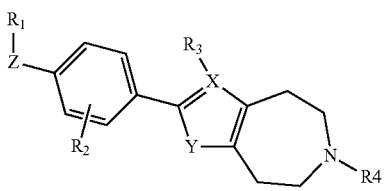
C
-continued
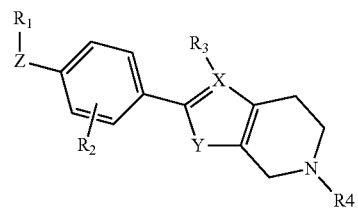
D
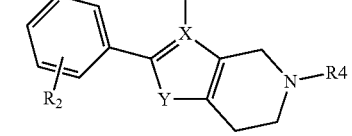
22 Claims, 1 Drawing Sheet

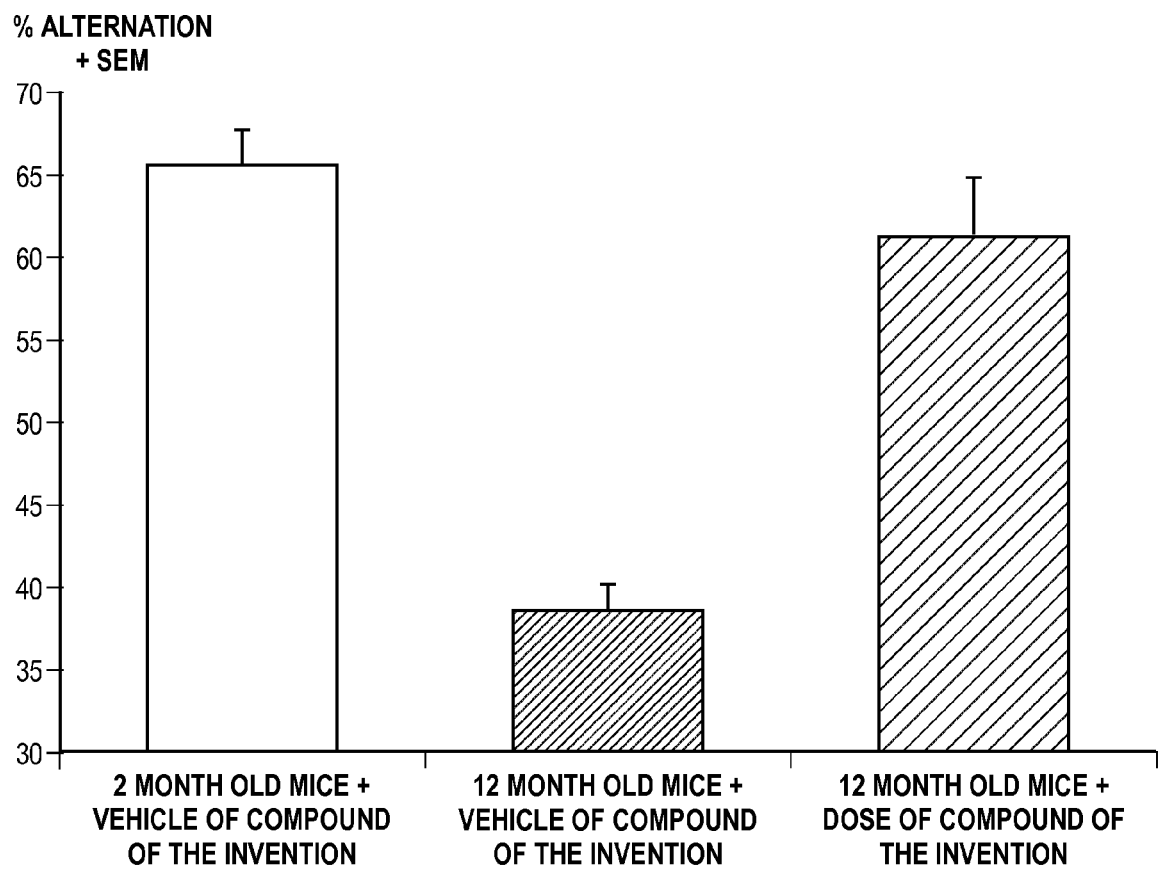

FUSED HETEROCYCLIC DERIVATIVES AS S1P MODULATORS

CROSS-REFERENCE TO RELATED APPLICATIONS

This is a divisional of U.S. patent application Ser. No. 13/808,908, filed on Apr. 18, 2013, now U.S. Pat. No. 8,796,262, which is a national stage entry under 35 U.S.C. §371 of International Patent Application No. PCT/EP2011/061586, filed on Jul. 8, 2011, which claims priority to U.S. Patent Application No. 61/362,784, filed on Jul. 9, 2010, U.S. Patent Application No. 61/446,541, filed on Feb. 25, 2011, European Patent Application No. 10169107.9, filed on Jul. 9, 2010, and European Patent Application No. 11156007.4, filed on Feb. 25, 2011, the contents of all of which are fully incorporated herein by reference.

FIELD OF THE INVENTION

This invention relates to new fused heterocyclic derivatives having affinity to S1P receptors, a pharmaceutical composition containing said compounds, as well as the use of said compounds for the preparation of a medicament for treating, alleviating or preventing diseases and conditions in which any S1P receptor is involved or in which modulation of the endogenous S1P signaling system via any S1P receptor is involved.

BACKGROUND OF THE INVENTION

Sphingosine-1-phosphate (S1P) is a bioactive sphingolipid that mediates a wide variety of cellular responses, such as proliferation, cytoskeletal organization and migration, adherence- and tight junction assembly, and morphogenesis. S1P can bind with members of the endothelial cell differentiation gene family (EDG receptors) of plasma membrane-localized G protein-coupled receptors. To date, five members of this family have been identified as S1P receptors in different cell types, S1P1 (EDG-1), S1P2 (EDG-5), S1P3 (EDG-3), S1P4 (EDG-6) and S1P5 (EDG-8). S1P can produce cytoskeletal re-arrangements in many cell types to regulate immune cell trafficking, vascular homeostasis and cell communication in the central nervous system (CNS) and in peripheral organ systems.

It is known that S1P is secreted by vascular endothelium and is present in blood at concentrations of 200-900 nanomolar and is bound by albumin and other plasma proteins. This provides both a stable reservoir in extracellular fluids and efficient delivery to high-affinity cell-surface receptors. S1P binds with low nanomolar affinity to the five receptors S1P1-5. In addition, platelets also contain S1P and may be locally released to cause e.g. vasoconstriction. The receptor subtypes S1P1, S1P2 and S1P3 are widely expressed and represent dominant receptors in the cardiovascular system. Further, S1P1 is also a receptor on lymphocytes. S1P4 receptors are almost exclusively in the haematopoietic and lymphoid system. S1P5 is primarily (though not exclusively) expressed in central nervous system. The expression of S1P5 appears to be restricted to oligodendrocytes in mice, the myelinating cells of the brain, while in rat and man expression at the level of astrocytes and endothelial cells was found but not on oligodendrocytes.

S1P receptor modulators are compounds which signal as (ant)agonists at one or more S1P receptors. The present invention relates to modulators of the S1P5 receptor, in particular agonists, and preferably to agonists with selectivity over S1P1 and/or S1P3 receptors, in view of unwanted cardiovascular and/or immunomodulatory effects. It has now been found that S1P5 agonists can be used in the treatment of cognitive disorders, in particular age-related cognitive decline.

Although research is ongoing to develop therapeutics that can be used to treat age related cognitive decline and dementia, this has not yet resulted in many successful candidates. Therefore, there is a need for new therapeutics with the desired properties.

DESCRIPTION OF THE INVENTION

It has now been found that fused heterocyclic derivatives of the formula (I)

A fused heterocyclic derivative of the formula (I)

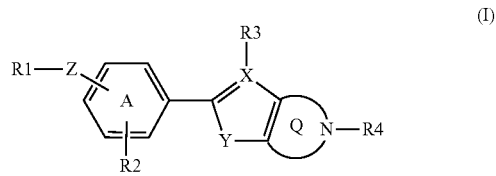

(I)

wherein
R1 is selected from
  cyano,
  (2-4C)alkenyl, (2-4C)alkynyl, (1-4C)alkyl, each optionally substituted with CN or one or more fluoro atoms,
  (3-6C)cycloalkyl, (4-6C)cycloalkenyl or a (8-10C)bicyclic group, each optionally substituted with halogen or (1-4C)alkyl optionally substituted with one or more fluoro atoms,
  phenyl, biphenyl, naphthyl, each optionally substituted with one or more substituents independently selected from halogen, cyano, (1-4C)alkyl optionally substituted with one or more fluoro atoms, (1-4C)alkoxy optionally substituted with one or more fluoro atoms, amino, dimethylamino, and (3-6C)cycloalkyl optionally substituted with phenyl which may be substituted with (1-4C)alkyl or halogen, and
  phenyl substituted with phenoxy, benzyl, benzyloxy, phenylethyl or monocyclic heterocycle, each optionally substituted with (1-4C)alkyl,
Z is a linking group —W—($C_n$-alkylene)-T- wherein
  W is attached to R1 and selected from a bond, —O—, —CO—, —S—, —SO—, —SO$_2$—, —NH—, —CH=CH—, —C(CF$_3$)=CH—, —C≡C—, —CH$_2$—O—, —O—CO—, —CO—O—, —CO—NH—, —NH—CO— and trans-cyclopropylene;
  n is an integer from 0 to 10; and
  T is attached to the phenylene/pyridyl moiety and selected from a bond, —O—, —S—, —SO—, —SO$_2$—, —NH—, —CO—, —C≡C—, —C≡C—, and trans-cyclopropylene;
R2 is H or one or more substituents independently selected from cyano, halogen, (1-4C)alkyl optionally substituted with one or more halogen atoms, or (1-4C)alkoxy optionally substituted with one or more halogen atoms;
ring structure A may contain one nitrogen atom;
X is selected from C or N; if X is C, R3 is selected from H and (1-4C)alkyl, otherwise R3 is not present;
Y is selected from NH, O and S;
structure Q is a 5-, 6- or 7-membered cyclic amine; and
R4 is (1-4C)alkylene-R5 wherein one or more carbon atoms in the alkylene group may independently be substituted with one or more halogen atoms or with (CH₂)₂ to form a cyclopropyl moiety, or R4 is (3-6C)cycloalkylene-R5, —CH₂-(3-6C)cycloalkylene-R5, (3-6C)cycloalkylene-CH₂—R5 or —CO—CH₂—R5, wherein R5 is —OH, —PO₃H₂, —OPO₃H₂, —COOH, —COO(1-4C)alkyl or tetrazol-5-yl;

or a pharmaceutically acceptable salt, a solvate or hydrate thereof or one or more N-oxides thereof display affinity for S1P receptors. In particular, compounds of the invention show selective affinity for the S1P5 receptor over the S1P1 and/or S1P3 receptor(s).

In WO 2008/012010, some of the disclosed compounds have somewhat structural similarity to the compounds of the present invention; however, they are described as histamine H3-receptor ligands.

The compounds of the invention are modulators of the S1P receptor, in particular of the S1P5 receptor. More specifically, the compounds of the invention are S1P5 receptor agonists. The compounds of the invention are useful for treating, alleviating and preventing diseases and conditions in which (any) S1P receptor(s)—in particular S1P5—is (are) involved or in which modulation of the endogenous S1P signaling system via any S1P receptor is involved. In particular, the compounds of the present invention may be used to treat, alleviate or prevent CNS (central nervous system) disorders, such as neurodegenerative disorders, in particular—but not limited to—cognitive disorders (in particular age-related cognitive decline) and related conditions, Alzheimer's disease, (vascular) dementia, Nieman's Pick disease, and cognitive deficits in schizophrenia, obsessive-compulsive behavior, major depression and autism, multiple sclerosis, pain, etc. Preferably, the compounds of the present invention may be used to treat, alleviate or prevent cognitive disorders (in particular age-related cognitive decline) and related conditions.

In a preferred embodiment of the invention, the compounds have formula (I) wherein
R1 is selected from
(3-6C)cycloalkyl or a (8-10C)bicyclic group optionally substituted with halogen, (1-4C)alkyl, and
phenyl optionally substituted with one or more substituents independently selected from halogen, cyano, (1-4C)alkyl, (1-4C)alkoxy, trifluoromethyl and trifluoromethoxy;
W is selected from a bond, —O—, —CO—, —S—, —SO—, —SO₂—, —NH—, —CH═CH—, —C≡C—, and trans-cyclopropylene; and
n is an integer from 0 to 4; and preferably, n is selected from 0, 1 and 2; and R2 is H or one or more substituents independently selected from halogen, (1-4C)alkyl optionally substituted with one or more fluoro atoms or (1-4C)alkoxy optionally substituted with one or more fluoro atoms;
and wherein the definition of the other groups/symbols is as defined previously.

In another embodiment, the compound of the invention has the structure (Ia)

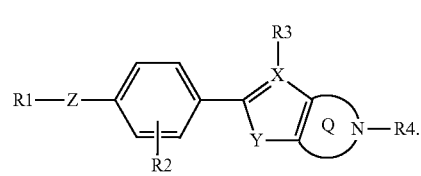

(Ia)

In an embodiment of the invention, ring structure Q is a 6-membered ring. In particular, the compound of the invention has the structure (Ib)

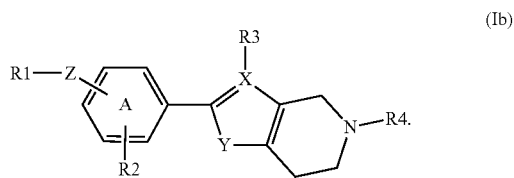

(Ib)

In a further embodiment of the invention, R4 is selected from —(CH₂)₂—OH, —CH₂—COOH, —(CH₂)₂—COOH, —(CH₂)₃—COOH, —CH₂—CHCH₃—COOH, —CH₂—C(CH₃)₂—COOH, —CHCH₃—CH₂—COOH, —CH₂—CF₂—COOH, —CO—CH₂—COOH, ![structure]

1,3-cyclobutylene-COOH, —(CH₂)₂—PO₃H₂, —(CH₂)₃—PO₃H₂, —(CH₂)₂—OPO₃H₂, —(CH₂)₃—OPO₃H₂, —CH₂-tetrazol-5-yl, —(CH₂)₂-tetrazol-5-yl and —(CH₂)₃-tetrazol-5-yl. Preferred R4 groups are selected from —(CH₂)₂—COOH, —(CH₂)₃—COOH, —CH₂—CHCH₃—COOH, —CH₂—C(CH₃)₂—COOH, —CHCH₃—CH₂—COOH, —CH₂—CF₂—COOH and. Highly preferred are —(CH₂)₂—COOH, —CHCH₃—CH₂—COOH, —CH₂—CHCH₃—COOH and 1,3-cyclobutylene-COOH. In particular preferred is —CH₂—CHCH₃—COOH.

In another preferred embodiment, the compounds have formula (I) wherein Y is O.

Further, in a preferred embodiment of the invention, X is N.

In preferred embodiments of the invention, R1 is indanyl optionally substituted with halogen, (1-4C)alkyl, or—more preferred—R1 is optionally substituted phenyl, wherein the optional substituents are selected from any of the previously defined substituents, but in particular the optional substituents are one or more substituents independently selected from halogen, cyano, (1-4C)alkyl, (1-4C)alkoxy, trifluoromethyl and trifluoromethoxy. In highly preferred embodiments, R1 is 4Cl-phenyl or 4CF₃-phenyl.

In an embodiment of the invention, R2 is H or one or more substituents independently selected from methyl, methoxy, chloro or fluoro. In a preferred embodiment, R2 is H or R2 represents one methyl, one methoxy, one chloro, one chloro, or one or two fluoro atoms.

In embodiments of the invention, wherein X is CR3, R3 is preferably H or methyl and in particular, R3 is H.

Further, in an embodiment of the invention, Z is the linking group —W—(CH₂)ₙ-T-, the meaning of which is selected from a bond, —O—, —CO—, —S—, —SO₂—, —NH—, —CH₂—, —(CH₂)₂—, —CCH₃—O—, —CH═CH—, —C≡C—, —CH₂—O—, —O—CH₂—, —CH₂—S—, —S—CH₂—, —CH₂—SO₂—, —SO₂—CH₂—, —CH₂—NH—, —NH—CH₂—, and trans-cyclopropylene. In preferred embodiments, Z is —O—, —CH₂—O— or trans-cyclopropylene. In particular, Z is —CH₂—O—.

The term halogen refers to fluoro, chloro, bromo, or iodo. Preferred halogens are fluoro and chloro, and in particular chloro.

The term (1-4C)alkyl means a branched or unbranched alkyl group having 1-4 carbon atoms, for example methyl, ethyl, propyl, isopropyl and butyl. A preferred alkyl group is methyl.

The term (1-4C)alkoxy means an alkoxy group having 1-4 carbon atoms, wherein the alkyl moiety is as defined above. A preferred alkoxy group is methoxy.

The terms (1-4C)alkylene and ($C_n$-alkylene) mean a branched or unbranched alkylene group having 1-4 or n carbon atoms, respectively, for example methylene, —CHCH$_3$—, —C(CH$_3$)$_2$—, —CHCH$_3$CH$_2$—, and the like. In the definition of R4 which is (1-4C)alkylene-R5, one or more carbon atoms in the alkylene group may (amongst others) independently be substituted with (CH$_2$)$_2$ to form a cyclopropyl moiety, meaning to form a R4 group such as

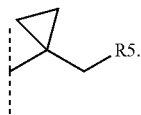

The term (2-4C)alkynyl means a branched or unbranched alkynyl group having 2-4 carbon atoms, wherein the triple bond may be present at different positions in the group, for example ethynyl, propargyl, 1-butynyl, 2-butynyl, etc.

The term (3-6C)cycloalkyl means a cyclic alkyl group having 3-6 carbon atoms, thus cyclopropyl, cyclobutyl, cyclopentyl or cyclohexyl. Preferred are cyclopentyl and cyclohexyl.

The term (4-6C)cycloalkenyl means a cyclic alkenyl group having 4-6 carbon atoms and comprising one or two double bonds, for example cyclohexenyl.

The term (3-6C)cycloalkylene means a cyclic alkyl group having two attachment points. Preferred is 1,3-cyclobutylene, having the structure

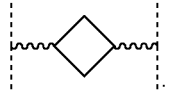

The term (8-10C)bicyclic group means a fused ring system of two groups selected from aromatic and non-aromatic ring structures having together 8-10 carbon atoms, for example the indane group.

With reference to substituents, the term "independently" means that the substituents may be the same or different from each other in the same molecule.

The compounds of the invention may suitably be prepared by methods available in the art, and as illustrated in the experimental section of this description.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Compounds may exist as polymorphs and as such are intended to be included in the present invention. In addition, compounds may form solvates with water (i.e., hydrates) or common organic solvents, and such solvates are also intended to be encompassed within the scope of this invention.

Isotopically-labeled compound of formula (I) or pharmaceutically acceptable salts thereof, including compounds of formula (I) isotopically-labeled to be detectable by PET or SPECT, also fall within the scope of the invention. The same applies to compounds of formula (I) labeled with [$^{13}$C]-, [$^{14}$C]-, [$^{3}$H]-, [$^{18}$F]-, [$^{125}$I]- or other isotopically enriched atoms, suitable for receptor binding or metabolism studies.

The term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They can be prepared in situ when isolating and purifying the compounds of the invention, or separately by reacting them with pharmaceutically acceptable non-toxic bases or acids, including inorganic or organic bases and inorganic or organic acids.

The compounds of the invention may be administered enterally or parenterally. The exact dose and regimen of these compounds and compositions thereof will be dependent on the biological activity of the compound per se, the age, weight and sex of the patient, the needs of the individual subject to whom the medicament is administered, the degree of affliction or need and the judgment of the medical practitioner. In general, parenteral administration requires lower dosages than other methods of administration which are more dependent upon adsorption. However, the dosages for humans are preferably 0.001-10 mg per kg body weight. In general, enteral and parenteral dosages will be in the range of 0.1 to 1,000 mg per day of total active ingredients.

Mixed with pharmaceutically suitable auxiliaries, e.g. as described in the standard reference "Remington, The Science and Practice of Pharmacy" (21$^{st}$ edition, Lippincott Williams & Wilkins, 2005, see especially Part 5: Pharmaceutical Manufacturing) the compounds may be compressed into solid dosage units, such as pills or tablets, or be processed into capsules or suppositories. By means of pharmaceutically suitable liquids the compounds can also be applied in the form of a solution, suspension or emulsion.

For making dosage units, e.g. tablets, the use of conventional additives such as fillers, colorants, polymeric binders and the like, is contemplated. In general, any pharmaceutically suitable additive which does not interfere with the function of the active compounds can be used.

Suitable carriers with which the compounds of the invention can be administered include for instance lactose, starch, cellulose derivatives and the like, or mixtures thereof, used in suitable amounts. Compositions for intravenous administration may for example be solutions of the compounds of the invention in sterile isotonic aqueous buffer. Where necessary, the intravenous compositions may include for instance solubilizing agents, stabilizing agents and/or a local anesthetic to ease the pain at the site of the injection.

Pharmaceutical compositions of the invention may be formulated for any route of administration and comprise at least one compound of the present invention and pharmaceutically acceptable salts thereof, with any pharmaceutically suitable ingredient, excipient, carrier, adjuvant or vehicle.

By "pharmaceutically suitable" it is meant that the carrier, diluent or excipient must be compatible with the other ingredients of the formulation and not deleterious to the recipient thereof.

In an embodiment of the invention, a pharmaceutical pack or kit is provided comprising one or more containers filled with one or more pharmaceutical compositions of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described in this document.

LEGEND TO THE FIGURES

FIG. 1 Percentage of alternation of young and old C57BL/6J male mice in the T-maze with either vehicle (control groups) or compound of the invention (dose in mg/kg; p.o.)

The following examples are intended to further illustrate the invention in more detail.

Any novel intermediate as disclosed herein is a further embodiment of the present invention.

EXAMPLES

§1. Analytical Methods

Nuclear magnetic resonance spectra ($^1$H NMR and $^{13}$C NMR, APT) were determined in the indicated solvent using a Bruker ARX 400 ($^1$H: 400 MHz, $^{13}$C: 100 MHz) at 300 K, unless indicated otherwise. $^{19}$F NMR and $^{13}$C NMR experiments were carried out on a Varian Inova 500 spectrometer operating at 11.74 T (499.9 MHz for $^1$H, 125.7 MHz for $^{13}$C, 50.7 Mhz, 470.4 MHz for $^{19}$F) using a 5 mm SW probe. The spectra were determined in deuterated chloroform or DCM obtained from Cambridge Isotope Laboratories Ltd. Chemical shifts (δ) are given in ppm downfield from tetramethylsilane ($^1$H, $^{13}$C) or CCl$_3$F ($^{19}$F). Coupling constants J are given in Hz. Peak shapes in the NMR spectra are indicated with the symbols 'q' (quartet), 'dq' (double quartet), 't' (triplet), 'dt' (double triplet), 'd' (doublet), 'dd' (double doublet), 's' (singlet), 'bs' (bs) and 'm' (multiplet). NH and OH signals were identified after mixing the sample with a drop of D$_2$O.

Flash chromatography refers to purification using the indicated eluent and silica gel (either Acros: 0.030-0.075 mm or Merck silica gel 60: 0.040-0.063 mm).

Column chromatography was performed using silica gel 60 (0.063-0.200 mm, Merck).

Reactions were monitored by using thin-layer chromatography (TLC) on silica coated plastic sheets (Merck precoated silica gel 60 F254) with the indicated eluent. Spots were visualized by UV light (254 nm) or I$_2$.

Melting points were recorded on a Büchi B-545 melting point apparatus.

Liquid Chromatography-Mass Spectrometry (LC-MS):
—Method A.

The LC-MS system consists of a Waters 1525 μ-pump. The pump is connected to a Waters 2777 auto sampler.

The LC method is:

| step | total time | flow (ul/min) | A(%) | B(%) |
|---|---|---|---|---|
| 0 | 0.2 | 1600 | 90 | 10 |
| 1 | 2.5 | 1600 | 0 | 100 |
| 2 | 2.8 | 1600 | 0 | 100 |
| 3 | 2.9 | 1600 | 90 | 10 |
| 4 | 3.10 | 1600 | 90 | 10 |
| 5 | 3.11 | 500 | 90 | 10 |

A = 100% Water with 0.2% HCOOH
B = 100% ACN with 0.2% HCOOH

The auto sampler has a 10 ul injection loop; the injection volume is 10 μl. The auto sampler is connected to a Waters Sunfire C18 30*4.6 mm column with 2.5 um particles. The column is thermo stated at Room temperature +/−23° C.

The column is connected to a Waters 2996 PDA. The wavelength is scanned from 240 to 320 nm. The resolution is 1.2 nm and the sampling rate is 20 Hz. After the PDA the flow is split 1:1 and connected to a Waters 2424 ELSD.

The ELSD has the following parameters:

Gas pressure: 40 psi
Data rate 20 points/sec
Gain 500
Time constant 0.2 sec
Nebulizer mode cooling
Drift tube 50° C.

The samples are also measured with a Waters ZQ mass detector.

The mass spectrometer has the following parameters:

Scan range: 117-900 Amu
Polarity: positive
Data format: centroid
Time per scan: 0.500 sec
Interscan time: 0.05 sec
Capillary 2.5 kV
Cone 25 V
Extractor 2 V
RF lens 0.5 V
Source Temp. 125° C.
Desolvation Temp 400° C.
Cone gas 100 L/Hr
Desolvation Gas 800 L/Hr
LM 1 Resolution 15
HM 1 Resolution 15
Ion energy 0.5
Multiplier 500 V The complete system is controlled by Masslynx 4.1.
—Method B.

The LC-MS system consists of 2 Perkin Elmer series 200 micro pumps. The pumps are connected to each other by a 50 ul tee mixer. The mixer is connected to the Gilson 215 auto sampler.

The LC method is:

| step | total time | flow (ul/min) | A (%) | B (%) |
|---|---|---|---|---|
| 0 | 0 | 1800 | 95 | 5 |
| 1 | 1.8 | 1800 | 0 | 100 |
| 2 | 2.6 | 1800 | 0 | 100 |
| 3 | 2.8 | 1800 | 95 | 5 |
| 4 | 3.0 | 1800 | 95 | 5 |

A = 100% Water with 0.1% HCOOH
B = 100% Acetonitril with 0.1% HCOOH

The auto sampler has a 2 ul injection loop. The auto sampler is connected to a Waters Sunfire C18 4.6×30 mm column with 2.5 □m particles. The column is thermo stated in a Perkin Elmer series 200 column oven at 23° C. The column is connected to a Perkin Elmer 785 UV/VIS meter with a 2.7 ul flow cell. The wavelength is set to 254 nm. The UV meter is connected to a Sciex API 150EX mass spectrometer. The mass spectrometer has the following parameters:
Scan range: 100-900 Amu
Polarity: positive
Scan mode: profile
Resolution Q1: UNIT
Step size: 0.10 amu
Time per scan: 0.500 sec
NEB: 10
CUR: 10
IS: 5200
TEM: 325
DF: 30
FP: 225
EP: 10

The light scattering detector is connected to the Sciex API 150. The light scattering detector is a Polymer Labs PL-ELS 2100 operating at 70° C. and 1.7 bar $N_2$ pressure.

The complete system is controlled by a Dell precision GX370 computer operating under Windows 2000.

The reported retention times in Table 1 ($R_t$) are for the peak in the Total Ion Current (TIC) chromatogram which showed the mass for $[M+H]^+$ within 0.5 amu accuracy of the calculated exact MW and had an associated peak in the Evaporative Light Scattering (ELS) chromatogram with a relative area % (purity) of >85%.

§2. Abbreviations

ACE-Cl 1-Chloroethyl chloroformate
9-BBN 9-borabicyclo[3.3.1]nonane dimer
$CHCl_3$ Chloroform
$CH_2Cl_2$ Dichloromethane
$CH_3CN$ Acetonitrile
$CuBr_2$ Copper(II) bromide
DBU 1,8-Diazabicyclo[5.4.0]undec-7-cne
DIAD Diisopropyl azodicarboxylate
DIPEA N,N-Diisopropylethylamine
DMF N,N-dimethylformamide
DMSO Dimethyl sulfoxide
$Et_3N$ Triethylamine
$Et_2O$ Diethyl ether
EtOH Ethanol
EtOAc Ethyl acetate
HCl Hydrogen chloride
$K_2CO_3$ Potassium carbonate
$KHCO_3$ Potassium bicarbonate
KI Potassium iodide
KOH Potassium hydroxide
KOtBu Potassium tert-butoxide
MeOH Methanol
$NaBH_4$ Sodium borohydride
$NaHCO_3$ Sodium bicarbonate
NaI Sodium iodide
NaOH Sodium hydroxide
NaOtBu Sodium tert-butoxide
$NasSO_4$ Sodium sulfate
NBS N-Bromosuccinimide
$iPr_2O$ Diisopropyl ether
RT Room Temperature
$SiO_2$ Silica gel
TFA Trifluoroacetic acid
THF Tetrahydrofuran
TMSCl Chlorotrimethylsilane
TMSOTf Trimethylsilyl trifluoromethanesulfonate

§3. General Aspects of Syntheses

Suitable syntheses of claimed compounds are described below.

For the synthesis of compounds 1, two routes are described in respectively Schemes 2 and 3. Both routes start with compound 6, the synthesis of which is depicted in Scheme 1. Alpha alkylation of the pyrrolidine-enamine of 4 with alpha-bromo-acetophenones (3)—thereby introducing the Rb-group in the molecule—gives compound 5. Subsequent ring-closure of 5 under acidic conditions yielded compound 6 in fair yields.

Scheme 1. Synthesis of key-intermediate 6.

-continued

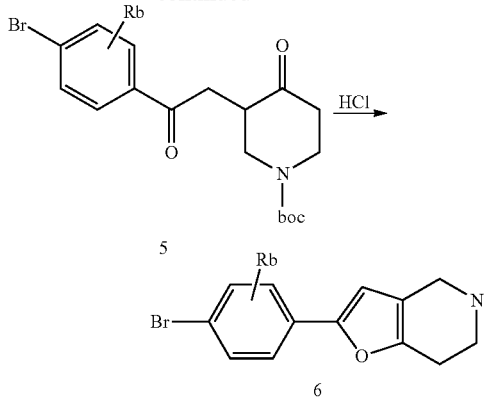

Route A (see Scheme 2) starts with the alkylation of the piperidine moiety in 6 by either a standard alkylation, reductive alkylation or Michael addition reaction to give the protected carboxylic acid compounds 7. The benzyl ether moiety could be introduced in two ways. Firstly, the bromine in 7 could be converted directly to the benzyl ether derivative 9 by a palladium catalyzed reaction. Additionally, bromide 7 can be converted to the phenol derivative 8 derivative via a palladium mediated reaction. Compound 8 can be converted to the desired benzyl ether derivatives 9 under phase transfer conditions with benzyl bromides or via a Mitsunobu reaction with benzyl alcohols. Finally, compounds 9 could be deprotected to give the end-products 1.

Scheme 2. Route A to compounds 1

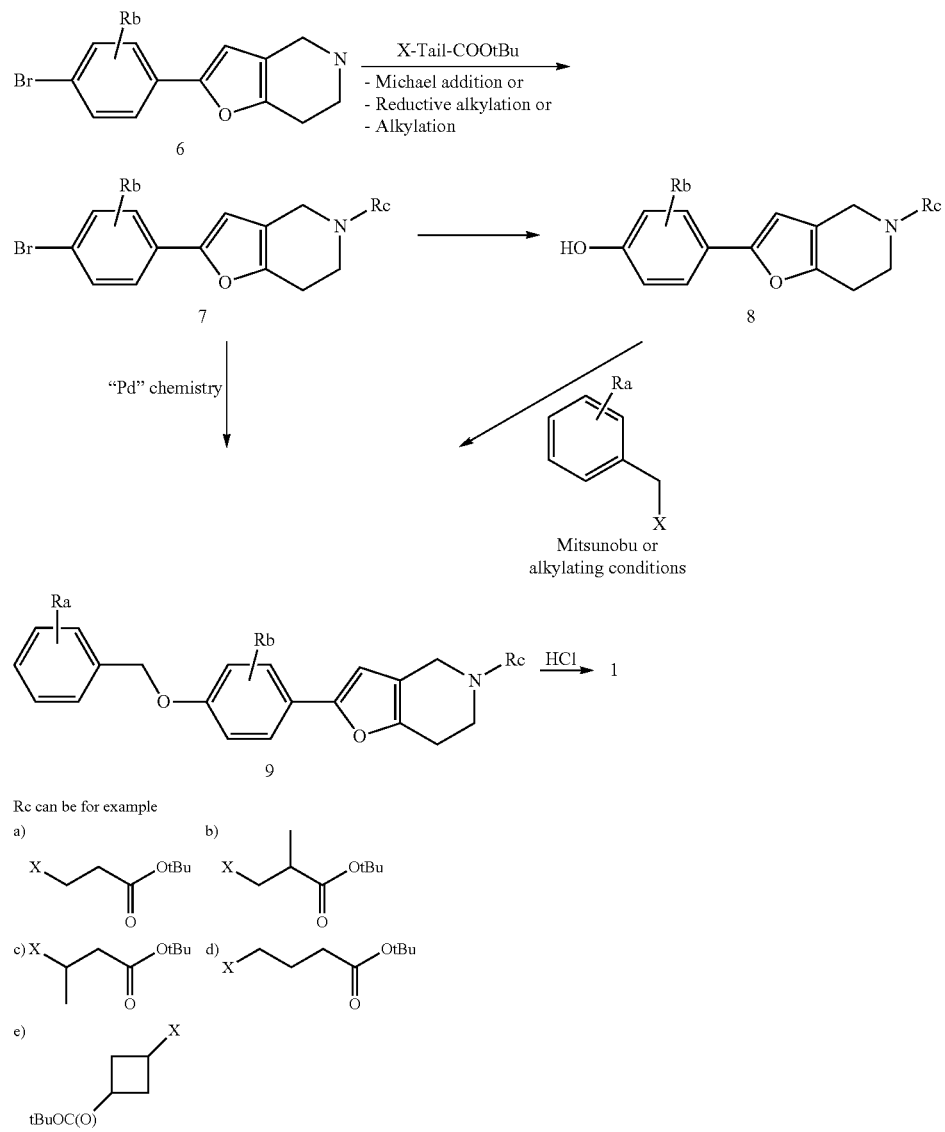

Alternatively, Route B (see Scheme 3) could be followed for the synthesis of compounds 1. The piperidine in compound 6 was protected with a BOC group. Hereafter, first the benzyl ether moiety was introduced either via a direct palladium mediated reaction of the bromine in 10 to 12 or via transforming the bromine to the phenol derivative 11, which could be converted to 12 under alkylation or Mitsunobu conditions. Finally, compound 12 could be converted to 9 by acidic removal of the BOC group and subsequent introduction of the protected carboxylic acid tails.

Scheme 3. Route B to compounds 1

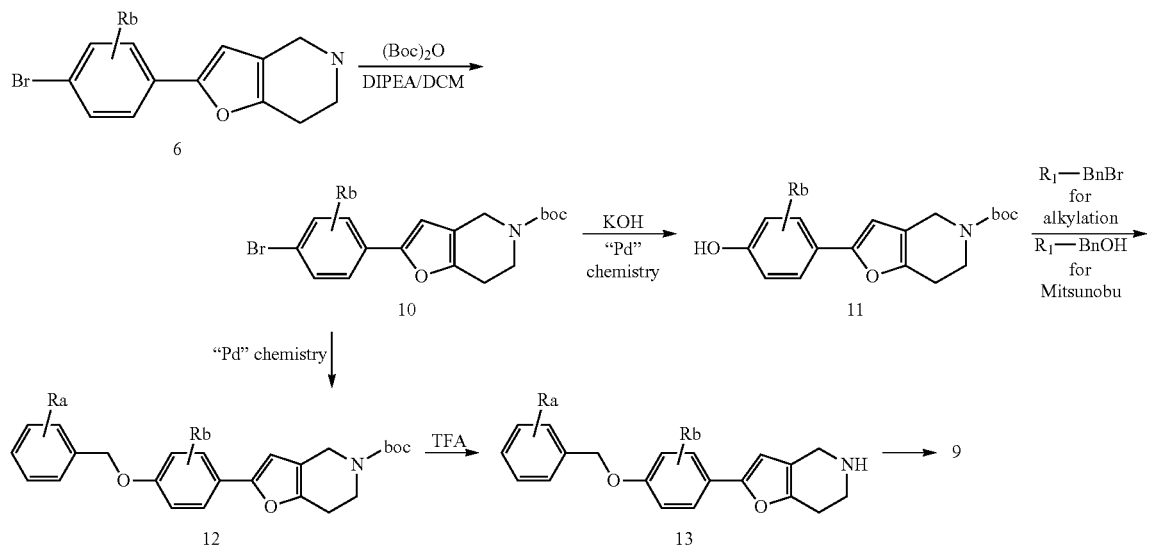

For the synthesis of oxazolo-derivatives 2, three routes were developed. The synthesis of key-intermediate 20 is depicted in Scheme 4. Acylation of commercially available 14 with a properly substituted benzoyl chloride (15) gave 16, which was subsequently ring-closed to 17 by using triphenylphosphine and hexachloroethane. Methylation of the pyridine in 17 to the quaternary salt 18 and subsequent reduction of 18 with sodium borohydride yielded compound 19. Compound 19 was demethylated with 1-chloroethyl chloroformate to furnish key-intermediate 20.

Scheme 4. Synthesis of compounds 20.

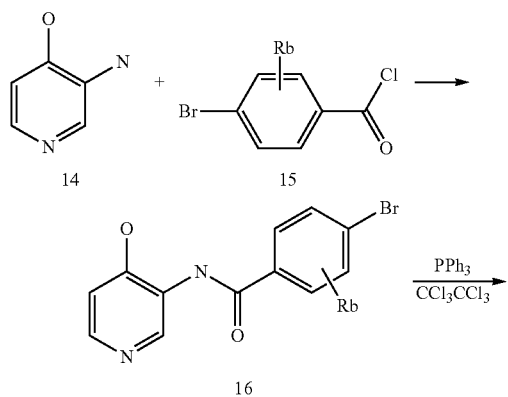

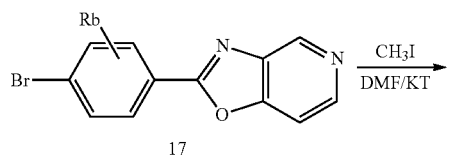

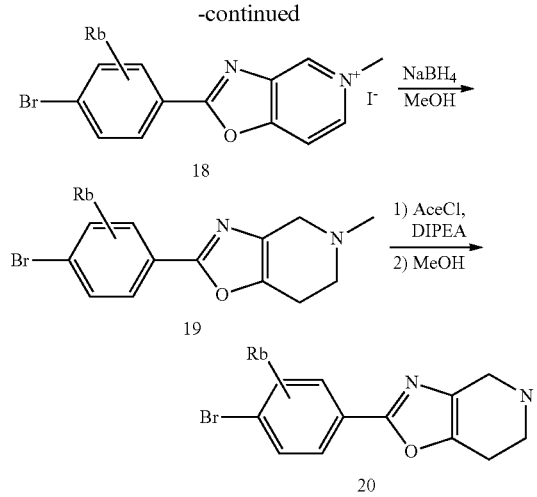

The first route (Route C) to compounds 2 is outlined in Scheme 5 and starts from compound 20. In a similar fashion as described for the synthesis of compounds 7 in the furanyl series, the t-butyl protected carboxylic acid tails could be introduced in 20 to give 21. Starting from 21, the benzyl ether derivatives 23 could be prepared by either a direct palladium mediated coupling (21 to 23) with benzyl alcohols or by first transforming the bromide in 21 to phenol 22 and subsequent benzylation of 22 (to 23) under phase transfer or Mitsunobu conditions. Finally, acidic deprotection of the carboxylic acid in 23 yielded compounds 2.

Scheme 5. Route C to compounds 2.

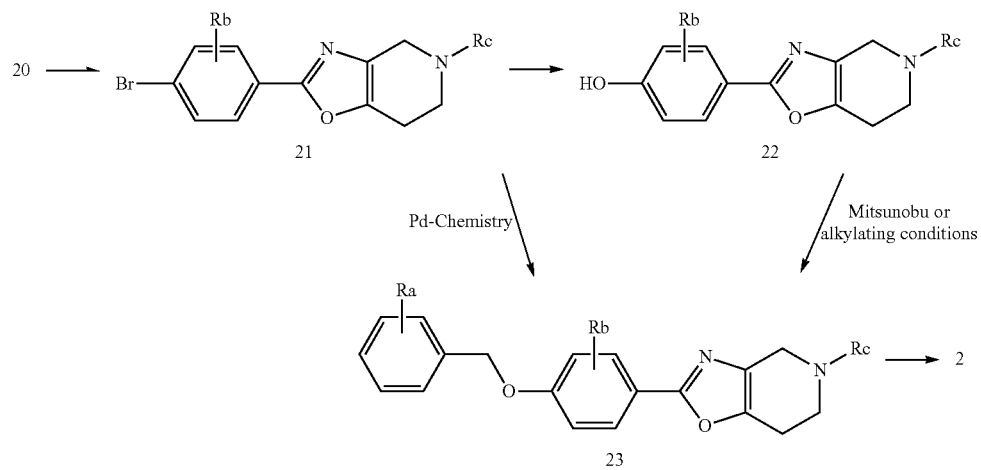

Rc can be for example

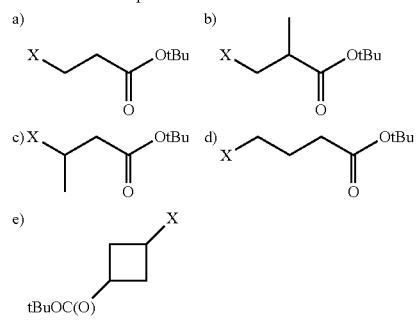

Alternatively, route D could be followed as depicted in Scheme 6. Compounds 25 could be prepared starting from 14 and a properly substituted 4-benzyloxy-benzoic acid derivative (24) under the influence of triphenylphosphine and trichloroacetonitril. Compound 25 could be converted to the benzyloxy-derivatives 23 in a similar fashion as described above in Schemes 4 and 5 for the synthesis of compounds 21. Thus, methylation of 25 and subsequent reduction with NaBH$_4$ gave 26, which was demethylated with ACE-Cl to give 27. Finally, the tails were introduced in 27 to give compound 23. From here, the t-butyl group in 23 could be removed under acidic conditions to give compound 2. On the other hand, the benzyl in 23 can be removed by hydrogenation to give phenol derivatives 22.

Scheme 6. Route D to compounds 2.

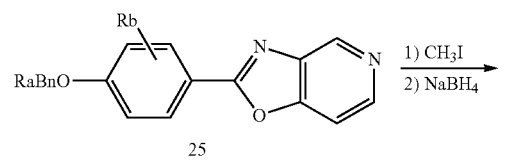

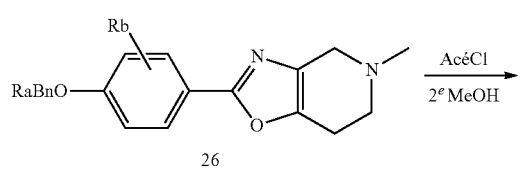

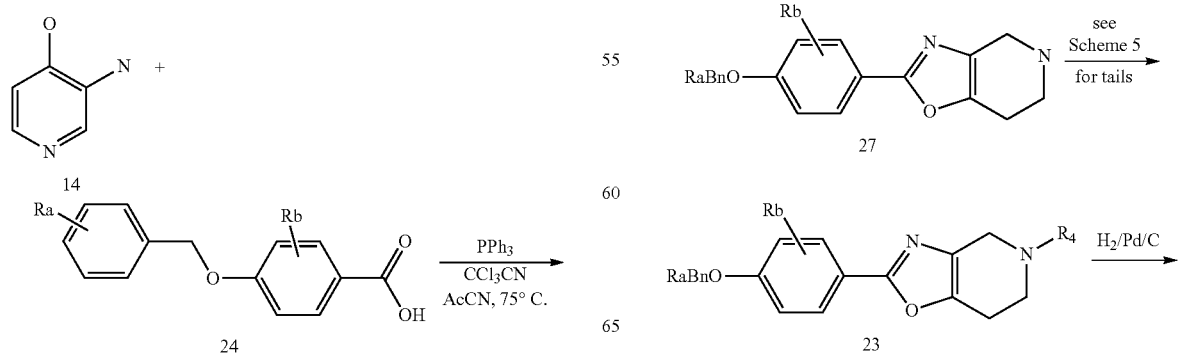

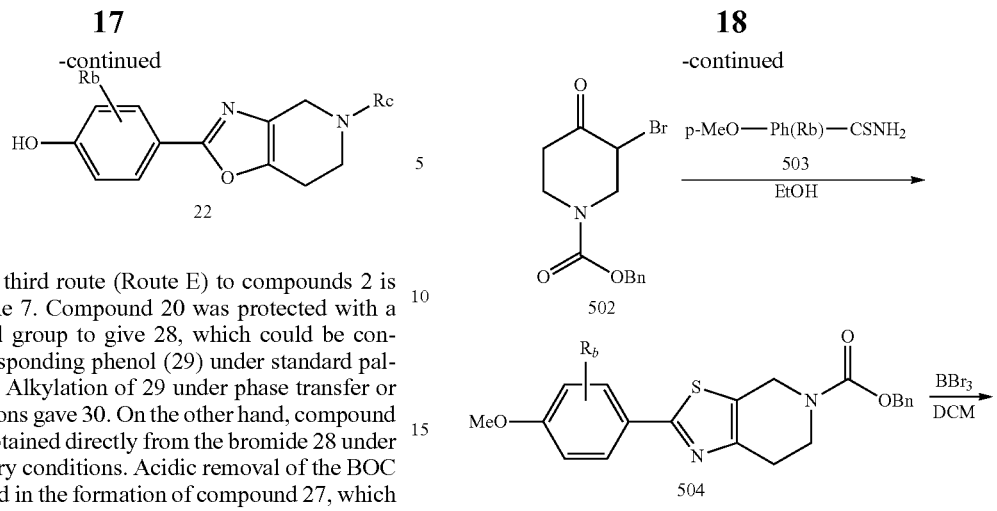

And finally, the third route (Route E) to compounds 2 is depicted in Scheme 7. Compound 20 was protected with a t-butyloxycarbonyl group to give 28, which could be converted to the corresponding phenol (29) under standard palladium conditions. Alkylation of 29 under phase transfer or Mitsunobu conditions gave 30. On the other hand, compound 30 could also be obtained directly from the bromide 28 under palladium chemistry conditions. Acidic removal of the BOC group in 30 resulted in the formation of compound 27, which could be alkylated to 23 as described in Scheme 5.

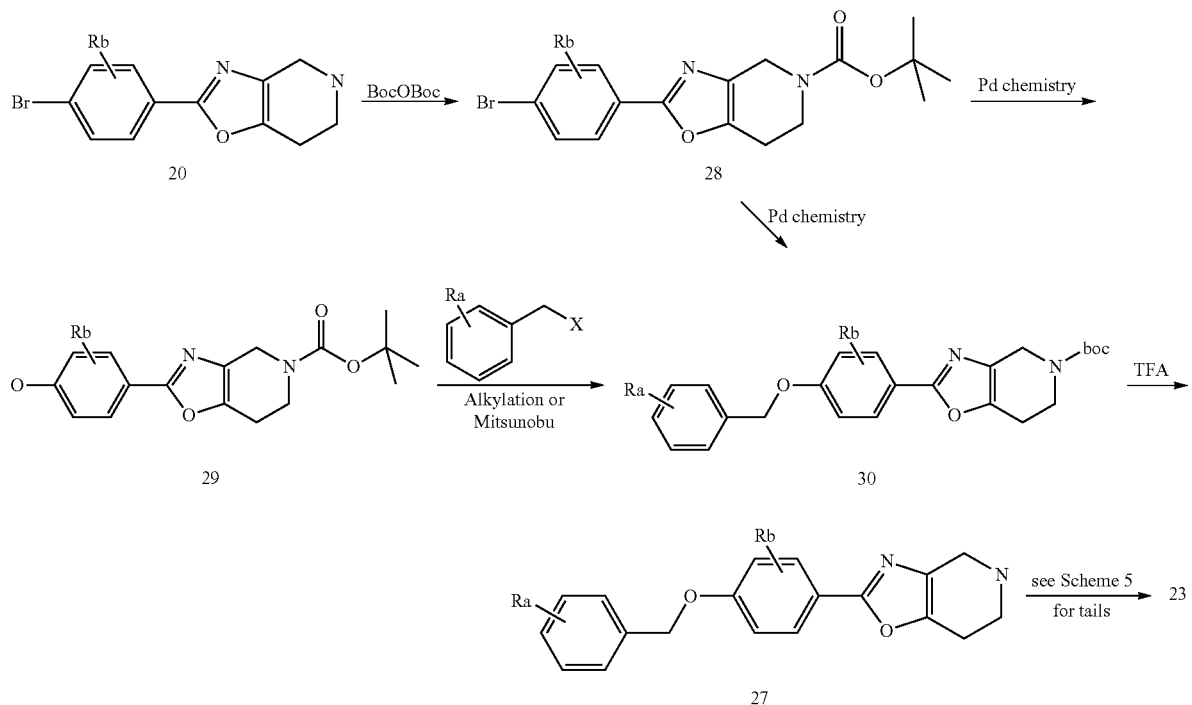

Scheme 7.
Route E for the synthesis of compounds 2

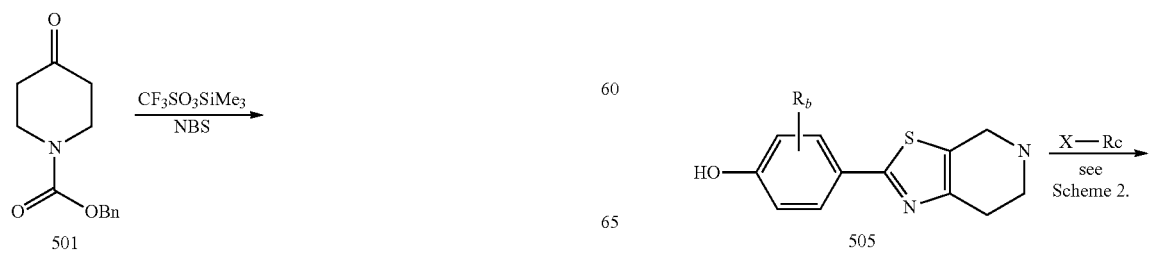

Scheme 8.

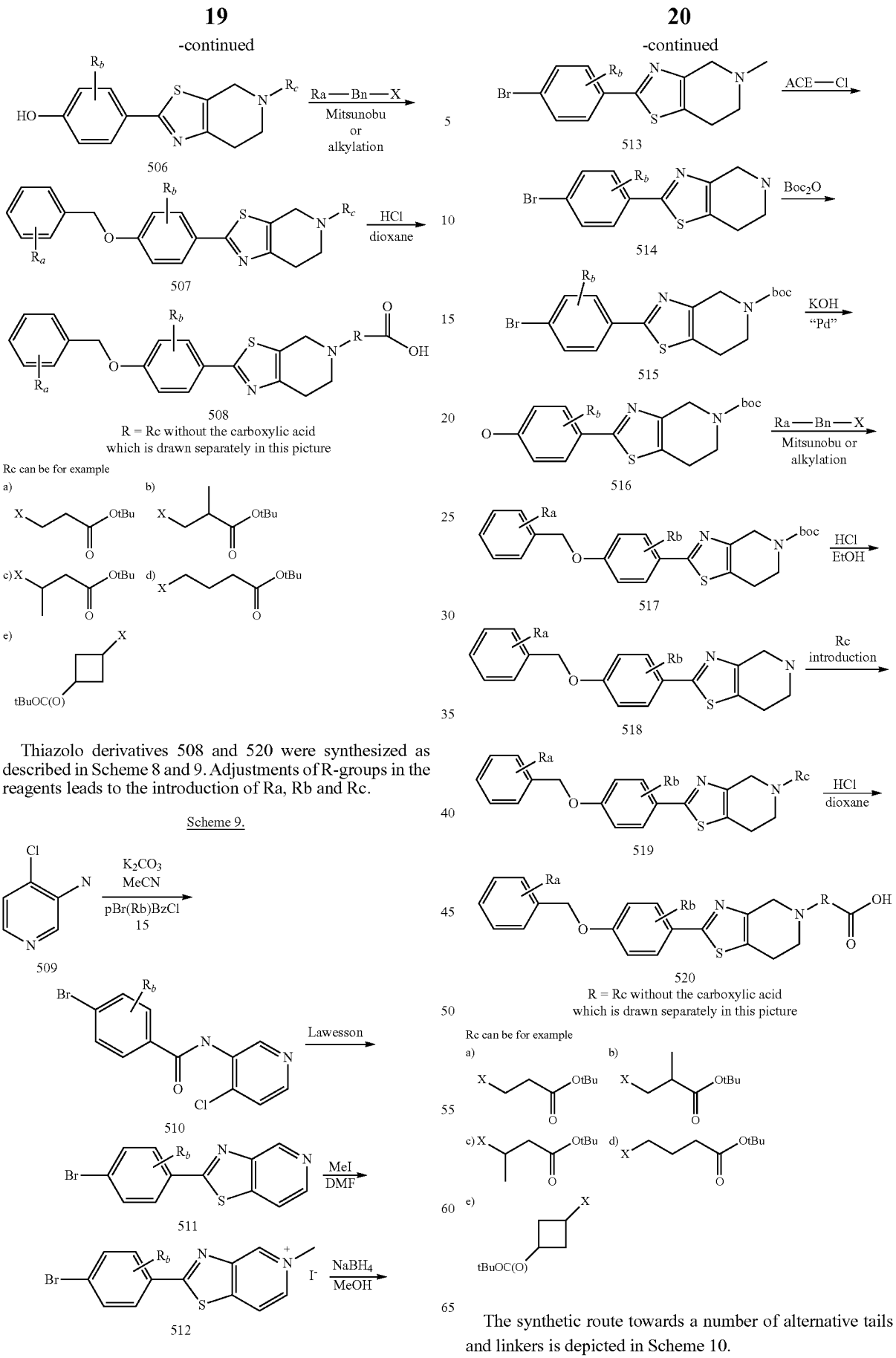
Thiazolo derivatives 508 and 520 were synthesized as described in Scheme 8 and 9. Adjustments of R-groups in the reagents leads to the introduction of Ra, Rb and Rc.
The synthetic route towards a number of alternative tails and linkers is depicted in Scheme 10.

Scheme 10.
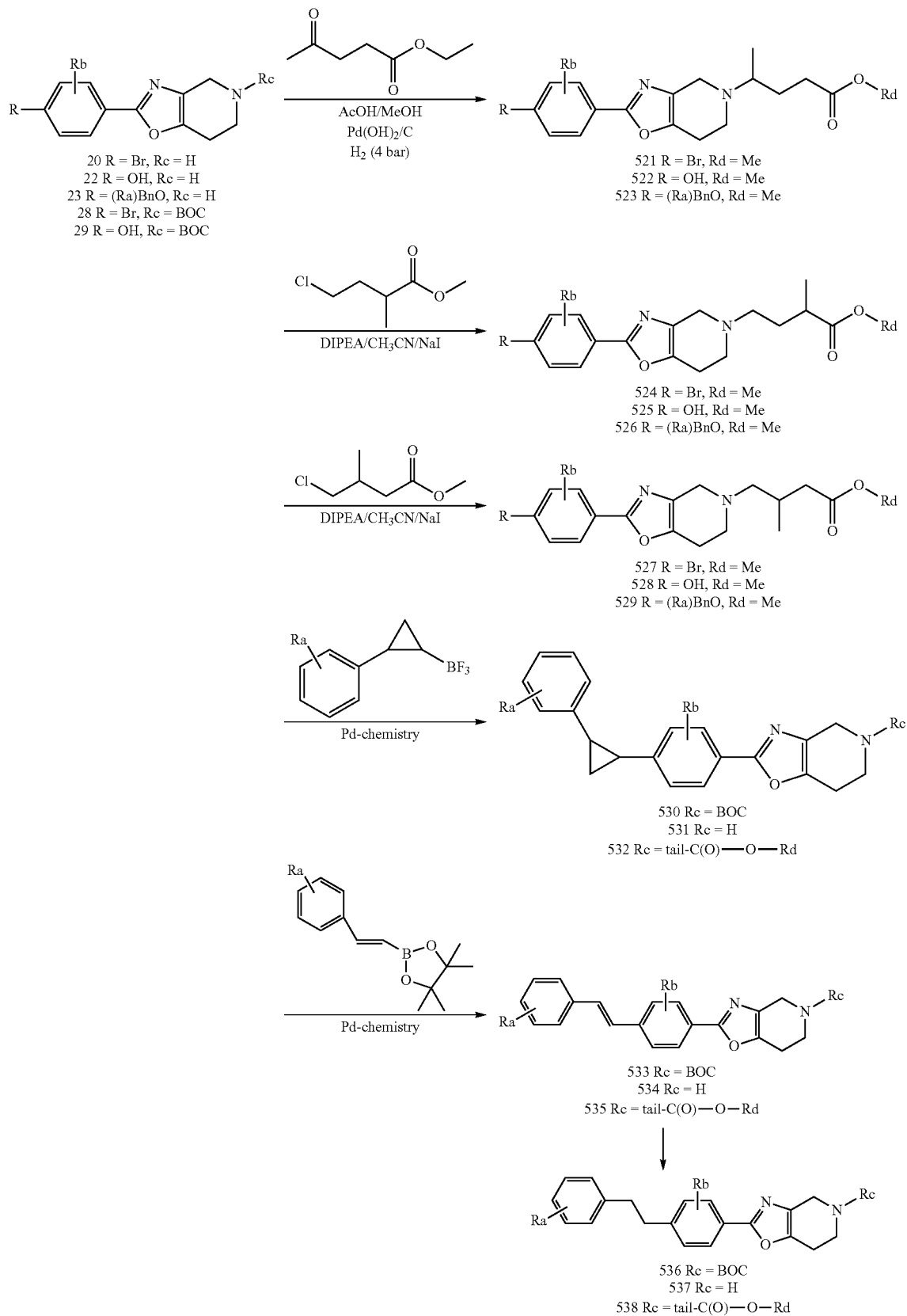

For those skilled in the art, it is clear that the choice for a certain route can be based on the availability of the reagents. In addition, the routes B, D and E are very suitable for the introduction of diversity in the Rc-tail part of compounds 1 and 2. Routes A and C have the introduction of the Ra-Bn moiety in the last part of the synthesis which makes it more suitable for exploring diversity in that part of the molecule.

§4. Syntheses of Intermediates

General Procedure for the Synthesis of Compounds 5.

To a solution of 4-oxo-piperidine-1-carboxylic acid t-butyl ester in toluene (2 ml/mmol) was added a catalytic amount of para-toluenesulphonic acid mono hydrate (0.1 eq) and pyrrolidine (4 eg). The mixture was heated to reflux under Dean Stark conditions for 18 hours. The mixture was concentrated under reduced pressure and the residue was redissolved in toluene. To this solution was added slowly (in 25 minutes) a solution of a properly substituted 2-bromo-1-(4-bromo-phenyl)-ethanone (1.05 eq) in toluene/DCM (2 ml/mmol, 1/2, v/v). The mixture was stirred overnight at room temperature and the resulting white slurry was poured out into water. The water layer was extracted with DCM (3 times) and the combined organic layers were dried ($MgSO_4$) and subsequently concentrated under reduced pressure. The resulting oil was purified by silica gel chromatography giving compound 5 in a yield of 50-90%.

General Procedure for the Synthesis of Compounds 6.

Compound 5 was suspended in concentrated hydrochloric acid (10 eq, 12N). The mixture was heated (in steps of 10° C. per 30 minutes) to 80° C. The mixture starts to foam heavily, so allow enough volume in the starting reaction vessel. After 45 minutes, the mixture was cooled to 0° C. and neutralized with 50 wt % solution of NaOH (exothermic). After stirring overnight at room temperature, the resulting solid material was collected by filtration and washed with 0.1M NaOH. The light brown material was purified by Soxhlet extraction in EtOAc giving 6 as beige solid which was used in the next step without further purification.

General Procedure for the Introduction of the Protected Carboxylic Acid Tails (7).

a) Introduction of the Propionic Acid t-butyl Ester.

Compound 6 was suspended in methanol (4 ml/mmol) and DIPEA was added (1.05 eg). To the mixture was added t-butyl acrylate (1.2 eq) and the mixture was refluxed for 16 hrs. Conversion was checked by TLC analysis. The solvents were evaporated and the residue was redissolved in EtOAc and extracted with a 5% solution of $NaHCO_3$. The organic layer was dried ($MgSO_4$), concentrated in vacuo and the residue was purified by silica gel column chromatography to give pure 7a.

b) Introduction of the 2-methyl-propionic acid t-butyl Ester.

Compound 6 was suspended in DMF (6 ml/mmol). To this suspension was added 1,8-diazabicyclo[5.4.0]undec-7-ene (3 eg) and t-butyl methacrylate (2 eq). The mixture was heated at 125° C. for 16-100 hrs. The solution was cooled and 5% $NaHCO_3$ was added (15 ml/mmol) and extracted with EtOAc. The organic layer was washed with water (4×), dried on $MgSO_4$, concentrated in vacuo and the residue was purified by silica gel column chromatography to give pure 7b.

c) Introduction of the 3-butyric acid t-butyl Ester.

Compound 6 was suspended in 1,2-dichloroethane (6 ml/mmol). To this suspension was added t-butylacetoacetate (1 eq) and sodium triacetoxy borohydride (1.4 eq). The mixture was stirred at room temperature for 16 hrs. If the reaction was not complete, another portion of t-butylacetoacetate (1 eq) and sodium triacetoxy borohydride (1.4 eq) was added. To the solution was added 5% $NaHCO_3$ (15 ml/mmol) and the mixture was extracted with DCM. The combined organic layers were dried on $Na_2SO_4$, concentrated in vacuo and the residue was purified by silica gel column chromatography to furnish pure 7c.

d) Introduction of the 4-butyric Acid t-Butyl Ester.

Compound 6 was suspended in acetonitril (3 ml/mmol). To this suspension was added potassium carbonate (2 eq), t-butyl 4-bromo-butanoate (1.1 eq) and potassium iodide (1.1 eq). The mixture was stirred at room temperature for 16 hrs after which time TLC analysis revealed complete reaction. The mixture was concentrated in vacuo and the residue was dissolved in EtOAc, washed with 5% NaHCO3 (15 ml/mmol). The organic layer was dried on $Na_2SO_4$, concentrated in vacuo and the residue was purified by silica gel column chromatography to yield 7d.

General Procedure for the Introduction of the Benzyl Ether Moiety in 7 to Compound 9.

A solution of compound 7, the properly substituted benzyl alcohol (1.1 eq), palladium(II) acetate (0.02 eq), 2-dit-butylphosphino-3,4,5,6-tertamethyl-2',4',6'-triisopropyl-1,1'biphenyl (0.02 eq), cesium carbonate (1.5 eq) in degassed toluene (4 ml/mmol) was heated at 75° C. for 16 hrs. Conversion was checked by TLC analysis. The solution was cooled to room temperature, diluted with DCM, filtered and concentrated in vacuo. The residue was purified by silica gel column chromatography to give compound 9 in yields varying from 30-80%.

General Procedure for the Conversion of the Bromine Derivatives 7 to the Phenol Derivatives 8.

Compound 7 was dissolved in toluene (8 mml/mmol) and to the solution was added potassium hydroxide (2 eq, 11.7N) and the solution was degassed. To the solution was added 2-dit-butylphosphino-2',4',6'-triisopropylbiphenyl (0.06 eq) and tris-(dibenzylideneaceton)-dipalladium(0) (0.03 eq). The mixture was stirred at 60° C. for 1.25 hrs. The mixture was allowed to reach room temperature, diluted with EtOAc and washed with 5% NaHCO3 solution (10 ml/mmol). The organic layers were dried on $MgSO_4$, filtered and concentrated in vacuo. The residue was purified by silica gel column chromatography to give compound 8 in yields varying from 25-85%.

General Procedure for the Conversion of the Phenol 8 to Benzyl Ethers 9.

Method A) Compound 8 was dissolved in DCM/water, 2/1, v/v (4 ml/mmol) and to this solution was added sodium hydroxide (2N, 3 eq). To this mixture were added tetrabutylammonium bromide (0.1 eq) and the properly substituted benzyl bromide (1.1 eq). The mixture was stirred for 16 hrs at room temperature after which time TLC analysis showed complete reaction. The mixture was diluted with DCM (15 ml/mmol), the layers were separated and the water layer was extracted with DCM. The organic layers were dried on $MgSO_4$, filtered and concentrated in vacuo. The residue was purified by silica gel column chromatography to give compound pure 9 in yields varying from 80-90%.

Method B) Compound 8 was dissolved in N,N'-dimethylacetamide (4 ml/mmol) and to this solution was added triphenylphosphine (1.25 eq) and diisopropyl azodicarboxylate (1.25 eq) and the properly substituted benzyl alcohol (1.2 eq). The mixture was stirred at room temperature for 16 hrs after which time TLC analysis showed complete reaction. The mixture was diluted with diethyl ether and washed with water (3×). The combined organic layers were dried on $MgSO_4$, filtered and concentrated in vacuo. The residue was purified by silica gel column chromatography to give compound 9 in yields varying from 70-90%.

General Procedure for the Acidic Deprotection of Compounds 9 to 1.

Compound 9 was dissolved in a solution of HCl in 1,4-dioxan (4N, 45 eq) and the mixture was stirred at room temperature for 24 hrs. Heating at 50° C. was applied when needed to push the reaction to completion. The solvents were evaporated and diisopropyl ether was added to precipitate the product. The white solid material was filtered and dried in vacuo to give compound 1 in a yield varying from 80-100%.

General Procedure for the Synthesis of the BOC Protected Derivatives of 6.

To a suspension of compound 6 in DCM (6 ml/mmol) were added DIPEA (1 eq), dimethylamino pyridine (DMAP, 0.05 eq) and di-t-butyl dicarbonate (1.1 eq). The mixture was stirred at room temperature for 16 hrs after which time TLC analysis revealed complete reaction. The reaction mixture was washed with 5% ag. NaHCO$_3$ solution and the resulting water layers were extracted with DCM. The combined organic layers were dried on MgSO$_4$, filtered and concentrated in vacuo. The residue was purified by silica gel column chromatography to give compound 10 in yields varying from 70-90%.

General Procedure for the Synthesis of Compounds 11.

Compound 10 was dissolved in 1,4-dioxan/water, 1/1, v/v (2 ml/mmol) and to the solution was added potassium hydroxide (4 eq, 11.7N) and the solution was degassed. To the solution was added 2-dit-butylphosphino-2',4',6'-triisopropylbiphenyl (0.04 eq) and tris-(dibenzylideneaceton)-dipalladium(0) (0.02 eq). The mixture was stirred at 80° C. for 16 hrs. The mixture was cooled to room temperature, diluted with EtOAc, acidified to pH 6 with 0.1N HCl and extracted with EtOAc. The organic layers were dried on MgSO$_4$, filtered and concentrated in vacuo. The residue was purified by silica gel column chromatography to give pure compound 11 in yields varying from 60-95%.

General Procedure for the Synthesis of the Benzyl Ether Derivatives 12.

Method A) Compound 11 was dissolved in DCM/water, 2/1, v/v (4 ml/mmol) and to this solution was added sodium hydroxide (2N, 3 eq). To this mixture were added tetrabutylammonium bromide (0.1 eq) and the properly substituted benzyl bromide (1.1 eq). The mixture was stirred for 16 hrs at room temperature after which time TLC analysis showed complete reaction. The mixture was diluted with DCM (15 ml/mmol), the layers were separated and the water layer was extracted with DCM. The organic layers were dried on MgSO$_4$, filtered and concentrated in vacuo. The residue was purified by silica gel column chromatography to give compound 12 in yields varying from 80-90%.

Method B) Compound 11 was dissolved in N,N'-dimethylacetamide (4 ml/mmol) and to this solution was added triphenylphosphine (1.25 eq), diisopropyl azodicarboxylate (DIAD, 1.25 eq) and a properly substituted benzyl alcohol (1.2 eq). The mixture was stirred for 16 hrs at room temperature after which time TLC analysis showed complete reaction. The mixture was diluted with diethyl ether and washed with water (3×). The combined organic layers were dried on MgSO$_4$, filtered and concentrated in vacuo. The residue was purified by silica gel column chromatography to give compound 12 in yields varying from 70-90%.

Method C) Compound 10 was dissolved in toluene (8 mml/mmol) and to the solution was added potassium hydroxide (2 eq, 11.7N) and the solution was degassed. To the solution was added properly substituted benzyl bromide (1.1 eq), 2-di-t-butylphosphino-2',4',6'-triisopropylbiphenyl (0.06 eq) and tris-(dibenzylideneaceton)-dipalladium(0) (0.03 eq). The mixture was stirred at 60° C. for 1.25 hrs. The mixture was cooled to room temperature, diluted with EtOAc and washed with 5% NaHCO$_3$ solution (10 ml/mmol). The organic layers were dried on MgSO$_4$, filtered and concentrated in vacuo. The residue was purified by silica gel column chromatography to give compound 12 in yields varying from 30-80%.

General Procedure for the Deprotection of Compounds 12 to 13.

Compound 12 was dissolved in DCM (10 ml/mmol) and trifluoroacetic acid (10 eq) was added. The solution was refluxed for 16 hrs after which time TLC analysis showed complete reaction. The mixture was neutralized with 5% aq. NaHCO$_3$. The mixture was extracted with DCM (3×) and the combined organic layers were washed with brine, dried on Na$_2$SO$_4$ and concentrated in vacuo to give compound 13 which was used in the next step without further purification.

General Procedure for the Introduction of the Protected Carboxylic Acid Tails (9) Starting from Compound 13.

a) Introduction of the Propionic acid t-butyl Ester.

Compound 13 was suspended in methanol (4 ml/mmol) and DIPEA was added (1.05 eg). To the mixture was added 1.2 eg of t-butyl acrylate and the mixture was refluxed for 16 hrs. Conversion was checked by TLC analysis. The solvents were evaporated and the residue was redissolved in EtOAc and extracted with a 5% solution of NaHCO$_3$. The organic layer was dried (MgSO$_4$), concentrated in vacuo and the residue was purified by silica gel column chromatography to give pure 9a.

b) Introduction of the 2-methyl-propionic Acid t-butyl Ester.

To a solution of compound 13 in DMF (6 ml/mmol) in a pyrex bottle was added 1,8-diazabicyclo[5.4.0]undec-7-ene (3 eg) and t-butyl-methacrylate (2 eq). The mixture was heated at 125° C. for 100 hrs. The solution was cooled and 5% NaHCO$_3$ was added (15 ml/mmol) and extracted with diethyl ether/EtOAc, 1/1, v/v. The organic layer was washed with water (4×), dried on MgSO$_4$, concentrated in vacuo and the residue was purified by silica gel column chromatography to give pure 9b.

c) Introduction of the 3-butyric Acid t-butyl Ester.

Compound 13 was suspended in 1,2-dichloroethane (6 ml/mmol). To this suspension was added t-butylacetoacetate (1 eq) and sodium triacetoxy borohydride (1.4 eq). The mixture was stirred at room temperature for 16 hrs. If the reaction was not complete, another portion of t-butylacetoacetate (1 eq) and sodium triacetoxy borohydride (1.4 eq) was added. After complete reaction, the solution was diluted with 5% NaHCO$_3$ (15 ml/mmol) and the mixture was extracted with DCM. The combined organic layers were dried on Na$_2$SO$_4$, concentrated in vacuo and the residue was purified by silica gel column chromatography to furnish pure compound 9c.

d) Introduction of the 4-butyric Acid t-butyl Ester.

Compound 13 was suspended in acetonitril (3 ml/mmol). To this suspension were added potassium carbonate (2 eq), t-butyl 4-bromo-butanoate (1.1 eq) and potassium iodide (1.1 eq). The mixture was heated at room temperature for 16 hrs after which time TLC analysis revealed complete reaction. The mixture was concentrated in vacuo and the residue was dissolved in EtOAc, washed with 5% NaHCO$_3$ (15 ml/mmol). The organic layer was dried on Na$_2$SO$_4$, concentrated in vacuo and the residue was purified by silica gel column chromatography to yield compound 9d.

General Procedure for the Synthesis of 2-(4-Bromo-phenyl)-oxazolo[4,5-c]pyridine 17.

To a cooled (0° C.) suspension of commercially available 4-hydroxy-3-amino-pyridine in DCM (14, 6 ml/mmol) was added triethyl amine (1.25 eq) and a solution of properly substituted benzoyl chloride 15 (1 eq, 0.3M in DCM). The reaction mixture was allowed to reach room temperature and the mixture was stirred for 16 to 64 hrs after which time TLC analysis showed complete reaction. The mixture was filtered, washed with DCM and ether to furnish 16 as a solid material (50-80% yield) which was used in the next step without further purification. Hexachloroethane (2.5 eq) was dissolved in DCM and triphenyl phosphine (3 eq) and triethyl amine (8 eq) was added. The mixture was stirred for 10 minutes at room temperature and compound 16 was added slowly in 5 equal portions. The mixture was stirred at room temperature for 64 hrs after which time TLC analysis (DCM/MeOH, 97/3, v/v) revealed complete reaction. The solution was concentrated and the residue was suspended in DCM. The mixture was filtered and the residue washed with DCM and diethyl ether to give 17 in a yield of 30-80%.

General Procedure for the Synthesis of Compounds 19.

To a solution of compound 17 in DMF was added iodomethane (4 eg) and the mixture was stirred for 16 hrs. The mixture was concentrated in vacuo and the residue was stirred in EtOAc to give 18 as a white solid. Compound 18 was dissolved in methanol (10 ml/mmol) and the solution was cooled to 0° C. Sodium borohydride (2 eg) was added and the mixture was stirred at 0° C. for 2 hrs after which time it was allowed to reach room temperature and stirring was continued for 16 hrs. Water was added (1 ml/mmol) and the mixture was stirred for 5 minutes. The mixture was co-evaporated with acetonitrile and the residue was purified by silica gel column chromatography to yield compound 19 in 50-90%.

General Procedure for the Synthesis of Compounds 20.

To a cooled (0° C.) solution of compound 19 in 1,2-dichloroethane (10 ml/mmol) was added DIPEA (2 eq). At 0° C. 1-chloroethyl chloroformate (3 eq) was added and the mixture was stirred for 10 minutes at 0° C. after which time the temperature was raised to reflux temperature. After 2 hrs, the mixture was concentrated in vacuo and the residue was dissolved in methanol (10 ml/mmol). The solution was stirred for 48 hrs at room temperature. Removal of the solvent resulted in the isolation of compound 20 in a yield of 70-90%.

General Procedure for the Synthesis of Compounds 21.

a) Introduction of the Propionic Acid t-butyl Ester.

Compound 20 was suspended in methanol (10 ml/mmol) and DIPEA was added (2.05 eg). To the mixture was added 1.2 eg of t-butyl acrylate and the mixture was refluxed for 16 to 120 hrs. Conversion was checked by TLC analysis and when needed additional reagents were added to push the reaction to completion. The solvents were evaporated and the residue was redissolved in EtOAc and extracted with a 5% solution of $NaHCO_3$. The organic layer was dried ($MgSO_4$), concentrated in vacuo and the residue was purified by silica gel column chromatography to give 21a in yields varying from 50-90% b) Introduction of the 2-methyl-propionic acid t-butyl Ester.

To a solution of compound 20 in DMF (6 ml/mmol) was added 1,8-diazabicyclo[5.4.0]undec-7-ene (DBU, 3 eg) and t-butylmethacrylate (5 eq). The mixture was heated at 125° C. for 100 hrs. The solution was cooled and 5% $NaHCO_3$ was added (15 ml/mmol) and extracted with diethyl ether/EtOAc, 1/1, v/v. The organic layer was washed with water (4×), dried on $MgSO_4$, concentrated in vacuo and the residue was purified by silica gel column chromatography to give pure 21b.

c) Introduction of the 3-butyric acid t-butyl Ester.

Compound 20 was suspended in 1,2-dichloroethane (8 ml/mmol). To this suspension were added t-butylacetoacetate (1.4 eq), acetic acid (1 eg) and sodium triacetoxy borohydride (1.8 eq). The mixture was stirred at room temperature for 16 hrs. If the reaction was not complete, another portion of t-butylacetoacetate (1 eq) and sodium triacetoxy borohydride (1.4 eq) was added. After complete reaction, the solution was diluted with 5% NaHCO3 (15 ml/mmol) and the mixture was extracted with DCM. The combined organic layers were dried on $Na_2SO_4$, concentrated in vacuo and the residue was purified by silica gel column chromatography to furnish pure compound 21c.

d) Introduction of the 4-butyric acid t-butyl Ester.

Compound 20 was suspended in DMF (5 ml/mmol). To this suspension was added potassium carbonate (3 eq) and t-butyl 4-bromobutanoate (3 eq). The mixture was heated at 80° C. for 16 hrs after which time TLC analysis revealed complete reaction. The mixture was concentrated in vacuo and the residue was purified by silica gel column chromatography to yield 21d.

General Procedure for the Synthesis of Compounds 22.

Compound 21 was dissolved in acetonitril (25 mml/mmol) and to the solution was added powdered potassium hydroxide (2 cq) and the solution was degassed. To the solution was added 2-dit-butylphosphino-3,4,5,6-tetramethyl-2',4',6'-triisopropyl-1,1-biphenyl (0.06 eq) and tris-(dibenzylideneaceton)-dipalladium(0) (0.03 eq). The mixture was stirred at 60° C. for 4 hrs. The mixture was cooled to room temperature and concentrated in vacuo. The residue was dissolved in DCM and washed with 0.1M HCl and water. The water layers were extracted with DCM and the combined organic layers was dried on $MgSO_4$. Compound 22 was obtained after silica gel column chromatography in yields varying from 30-70%.

General Procedure for the Introduction of the Benzyl Ether Moiety in 21 to Compound 23.

A solution of compound 21, the properly substituted benzyl alcohol (2 eq), palladium(II) acetate (0.02 eq), 2-dit-butylphosphino-3,4,5,6-tetramethyl-2',4',6'-triisopropyl-1, 1'biphenyl (0.02 eq), cesium carbonate (1.5 eq) in degassed toluene (3 ml/mmol) was heated at 75° C. for 16 hrs. Conversion was checked by TLC analysis. The solution was cooled to room temperature, diluted with DCM, filtered and concentrated in vacuo. The residue was purified by silica gel column chromatography to give compound pure 23 in yields varying from 30-80%.

General Procedure for the Conversion of the Phenol 22 to Benzyl Ethers 23.

Method A) Compound 22 was dissolved in DCM/water, 2/1, v/v (4 ml/mmol) and to this solution was added sodium hydroxide (2N, 3 eq). To this mixture were added tetrabutylammonium bromide (0.1 eq) and a properly substituted benzyl bromide (1.1 eq). The mixture was stirred for 16 hrs at room temperature after which time TLC analysis showed complete reaction. The mixture was diluted with DCM (15 ml/mmol), the layers were separated and the water layer was extracted with DCM. The organic layers were dried on $MgSO_4$, filtered and concentrated in vacuo. The residue was purified by silica gel column chromatography to give compound pure 23 in yields varying from 80-90%.

Method B) Compound 22 was dissolved in dry DCM (15 ml/mmol) and to this solution were added triphenylphosphine (1.8 eq) and the properly substituted benzyl alcohol (1.8 eq). To this mixture was added diisopropyl azodicarboxylate (1.8 eq) and the mixture was stirred for 16 hrs at room temperature after which time TLC analysis showed complete reaction. The mixture was concentrated in vacuo. The residue was purified by silica gel column chromatography to give compound pure 23 in yields varying from 70-90%.

Method C) PS-TBD (3.7 eq.) resin was incubated with a solution of 22 (1.1 eg) in 1 mL of acetonitril for 1.5 h at 50° C. Thereafter, the properly substituted benzyl bromide (1.10 eq.) in acetonitril was added. Subsequently, the reaction mixture was shaken and heated at 75° C. for 16 hrs. Next, the solvent was removed by filtration and the resin was washed with 3×2.5 mL ACN. The combined organics were concentrated in vacuo, followed by flash column chromatography on silica to give compound 23 in yields varying from 60-95%.

General Procedure for the Deprotection of 23 to Compounds 2.

Compound 23 was dissolved in a solution of HCl in 1,4-dioxan (4N, 100 eq) and the mixture was stirred for 16 hrs at room temperature. Heating at 50° C. was applied when needed to push the reaction to completion. The solvents were evaporated and diisopropyl ether was added to precipitate the product. The white solid material was filtered and dried in vacuo to give compound 2 in a yield varying from 70-100%.

General Procedure for the Synthesis of Compounds 25.

To a cooled (0° C.) suspension of commercially available 4-hydroxy-3-amino-pyridine (14) in acetonitril (15 ml/mmol) was added a properly substituted 4-benzyloxy-benzoic acid (24, 1 eq), triphenylphosphine (3 eq) and trichloroacetonitril (3 eq). The reaction mixture was allowed to reach room temperature and the mixture was stirred for 16 to 64 hrs at 80° C. The mixture was concentrated in vacuo and the residues was dissolved in DCM and washed with 2N NaOH (3×). The combined water layers were extracted with DCM and the organic layers dried (Na2SO4) to give crude 25 as oil which was used in the next step without further purification.

General Procedure for the Synthesis of Compounds 26.

To a solution of compound 25 in DMF (5 ml/mmol) was added iodomethane (4 eg) and the mixture was stirred for 16 hrs. The mixture was concentrated in vacuo and the residue was stirred in EtOAc to give the quaternary salt of 25 as a white solid. The crude material was dissolved in methanol (10 ml/mmol) and the solution was cooled to 0° C. Sodium borohydride (2.5 eg) was added and the mixture was stirred at 0° C. for 2 hrs after which time it was allowed to reach room temperature and stirring was continued for 16-64 hrs. Water was added (1 ml/mmol) and the mixture was stirred for 5 minutes. The mixture was concentrated in vacuo, the residues suspended in 2 N NaOH (5 ml/mmol) and extracted with DCM (3×). The combined organic layers were dried (Na2SO4) and concentrated to give crude 26 as a yellow solid which was used in the next step without further purification.

General Procedure to Compounds 27.

To a cooled (0° C.) solution of compound 26 in 1,2-dichloroethane (10 ml/mmol) was added DIPEA (2 eq) and 1-chloroethyl chloroformate (3 eq) was added. The mixture was stirred for 10 minutes at 0° C. after which time the temperature was raised to reflux temperature. After 4 hrs, the mixture was allowed to reach room temperature and stirring was continued for 16 hrs. The mixture was concentrated in vacuo and the residue was dissolved in methanol (10 ml/mmol). The solution was stirred for 16-48 hrs at room temperature. Removal of the solvent resulted in the isolation of crude 27 in an overall yield of 20-40% based on 25.

General Procedure for the Introduction of the Protected Carboxylic Acid Tails (to 23) Starting from Compound 27.

a) Introduction of the Propionic Acid t-butyl Ester.

Compound 27 was suspended in methanol (4 ml/mmol) and DIPEA was added (1.05 eg). To the mixture was added 1.2 eg of t-butyl acrylate and the mixture was refluxed for 16 hrs. Conversion was checked by TLC analysis. The solvents were evaporated and the residue was redissolved in EtOAc and extracted with a 5% solution of NaHCO3. The organic layer was dried (MgSO4), concentrated in vacuo and the residue was purified by silica gel column chromatography to give pure 23a.

b) Introduction of the 2-methyl-propionic Acid t-butyl Ester.

To a solution of compound 27 in DMF (6 ml/mmol) was added 1,8-diazabicyclo[5.4.0]undec-7-ene (3 eg) and t-butyl-methacrylate (4 eq). The mixture was heated at 125° C. for 100 hrs. The solution was cooled and 5% NaHCO3 was added (15 ml/mmol) and extracted with diethyl ether/EtOAc, 1/1, v/v. The organic layer was washed with water (4×), dried on MgSO4, concentrated in vacuo and the residue was purified by silica gel column chromatography to give pure 23b.

c) Introduction of the 3-butyric Acid t-butyl Ester.

Compound 27 was suspended in 1,2-dichloroethane (6 ml/mmol). To this suspension was added t-butylacetoacetate (1 eq) and sodium triacetoxy borohydride (1.4 eq). The mixture was stirred at room temperature for 16 hrs. If the reaction was not complete, another portion of t-butylacetoacetate (1 eq) and sodium triacetoxy borohydride (1.4 eq) was added. After complete reaction, the solution was diluted with 5% NaHCO3 (15 ml/mmol) and the mixture was extracted with DCM. The combined organic layers were dried on Na2SO4, concentrated in vacuo and the residue was purified by silica gel column chromatography to furnish pure compound 23c.

d) Introduction of the 4-butyric Acid t-butyl Ester.

Compound 27 was suspended in acetonitril (3 ml/mmol). To this suspension was added potassium carbonate (2 eq), t-butyl 4-bromobutanoate (1.1 eq) and potassium iodide (1.1 eq). The mixture was heated at room temperature for 16 hrs after which time TLC analysis revealed complete reaction. The mixture was concentrated in vacuo and the residue was dissolved in EtOAc, washed with 5% NaHCO3 (15 ml/mmol). The organic layer was dried on Na2SO4, concentrated in vacuo and the residue was purified by silica gel column chromatography to yield 23d.

e) Introduction of the 3-cyclobutanecarboxylic Acid.

Compound 27 was suspended in 1,2-dichloroethane (20 ml/mmol). To this suspension was added 3-oxocyclobutanecarboxylic acid (1.3 eq) and sodium triacetoxy borohydride (1.6 eq). The mixture was stirred at room temperature for 16 hrs. If the reaction was not complete, another portion of 3-oxocyclobutanecarboxylic acid (1.3 eq) and sodium triacetoxy borohydride (1.6 eq) was added. After complete reaction, the solution was diluted with 5% NaHCO3 (15 ml/mmol) and the mixture was extracted with DCM. The combined organic layers were dried on Na2SO4, concentrated in vacuo and the residue was purified by silica gel column chromatography to furnish pure compound 2e.

General Procedure for the Hydrogenation of 23 to Compound 22.

To a solution of compound 23 in ethanol (10 ml/mmol) was added palladium hydroxide on carbon (20%, 0.22 eg). Hydrogenation was started under atmospheric pressure of hydrogen. Stirring was continued for 16 hrs at room temperature. The mixture was filtered over Hyflo and the residue washed with ethanol. The filtrate was concentrated in vacuo to give compound 22.

General Procedure for the Synthesis of Compounds 28.

To a suspension of compound 20 in DCM (6 ml/mmol) were added DIPEA (1 eq), dimethylamino pyridine (DMAP, 0.05 eq) and di-t-butyl dicarbonate (1.1 eq). The mixture was stirred at room temperature for 16 hrs after which time TLC analysis revealed complete reaction. The mixture was concentrated in vacuo. The residue was purified by silica gel column chromatography to give compound pure 28 in yields varying from 70-90%.

General Procedure for the Synthesis of Compounds 29.

Compound 28 was dissolved in 1,4-dioxan/water, 1/1, v/v (10 ml/mmol) and to the solution was added potassium hydroxide (4 eq, 11.7N) and the solution was degassed. To the solution was added 2-di-t-butylphosphino-2',4',6'-triisopropylbiphenyl (0.04 eq) and tris-(dibenzylideneaceton)-dipalladium(0) (0.02 eq). The mixture was stirred at 80° C. for 16 hrs. The mixture was cooled to room temperature, diluted with EtOAc, acidified to pH 6 with 0.1N HCl and extracted with EtOAc. The organic layers were dried on MgSO$_4$, filtered and concentrated in vacuo. The residue was purified by silica gel column chromatography to give compound pure 29 in yields varying from 60-95%.

General Procedure for the Synthesis of the Benzyl Ether Derivatives 30.

Method A) Compound 29 was dissolved in DCM/water, 2/1, v/v (4 ml/mmol) and to this solution was added sodium hydroxide (2N, 3 eq). To this mixture was added tetrabutylammonium bromide (0.1 eq) and the properly substituted benzyl bromide (1.1 eq). The mixture was stirred for 16 hrs at room temperature after which time TLC analysis showed complete reaction. The mixture was diluted with DCM (15 ml/mmol), the layers were separated and the water layer was extracted with DCM. The organic layers were dried on MgSO$_4$, filtered and concentrated in vacuo. The residue was purified by silica gel column chromatography to give compound pure 30 in yields varying from 80-90%.

Method B) Compound 29 was dissolved in N,N'-dimethylacetamide (4 ml/mmol) and to this solution was added triphenylphosphino (1.25 cq), diisopropyl azodicarboxylate (1.25 eq) and a properly substituted benzyl alcohol (1.2 eq). The mixture was stirred for 16 hrs at room temperature after which time TLC analysis showed complete reaction. The mixture was diluted with diethyl ether and washed with water (3×). The combined organic layers were dried on MgSO$_4$, filtered and concentrated in vacuo. The residue was purified by silica gel column chromatography to give compound pure 30 in yields varying from 70-90%.

Method C) Compound 28 was dissolved in toluene (8 mml/mmol) and to the solution was added potassium hydroxide (2 eq, 11.7N) and the solution was degassed. To the solution was added properly substituted benzyl bromide (1.1 eq), 2-di-t-butylphosphino-2',4',6'-triisopropylbiphenyl (0.06 eq) and tris-(dibenzylideneaceton)-dipalladium(0) (0.03 eq). The mixture was stirred at 60° C. for 1.25 hrs. The mixture was cooled to room temperature, diluted with EtOAc and washed with 5% NaHCO$_3$ solution (10 ml/mmol). The organic layers were dried on MgSO$_4$, filtered and concentrated in vacuo. The residue was purified by silica gel column chromatography to give compound pure 30 in yields varying from 30-80%.

General Procedure for the Deprotection of Compounds 30 to 27.

Compound 30 was dissolved in DCM (10 ml/mmol) and trifluoroacetic acid (6 eq) was added. The solution was refluxed for 16 hrs after which time TLC analysis showed complete reaction. The mixture was neutralized with 5% aq. NaHCO$_3$. The mixture was extracted with DCM (3×) and the combined organic layers were washed with brine, dried on Na$_2$SO$_4$ and concentrated in vacuo to give compound 27 which was used in the next step without further purification.

§5. Syntheses of Specific Compounds (See Table 1)

All furanyl derivatives from Table 1 could be prepared by following either route A or B appropriate reagents. The following compounds are typical examples.

All oxazolo derivatives from Table 1 could be prepared by following either route C, D or E by choosing the appropriate reagents. The following compounds are typical examples.

3-[2-(4-Bromo-phenyl)-2-oxo-ethyl]-4-oxo-piperidine-1-carboxylic acid t-butyl ester (5, Rb=H)

To a solution of 4-oxo-piperidine-1-carboxylic acid t-butyl ester (4, 104.1 g, 522 mmol) in toluene (800 ml) was added a catalytic amount of para-toluenesulphonic acid mono hydrate (0.5 g, 2.6 mmol) and pyrrolidine (172.8 ml, 2090 mmol). The mixture was heated to reflux under Dean Stark conditions for 18 hours. The mixture was concentrated under reduced pressure and the residue was redissolved in toluene (600 ml). To this solution was added slowly (in 25 minutes) a solution of 2-bromo-1-(4-bromo-phenyl)-ethanone (3, Rb=H, 145.2 g, 522 mmol) in toluene/DCM (900 ml, 1/2, v/v). The mixture was stirred overnight at room temperature and the resulting white slurry was poured out in water (1.5 L). The water layer was extracted with DCM (3×300 ml) and the combined organic layers were dried (MgSO$_4$) and subsequently concentrated under reduced pressure. The resulting oil was purified by silica gel chromatography (diethyl ether/petroleum ether, 2/3, v/v to 100% diethyl ether) giving compound 5 (Rb=H, 166.6 g, 87%) as a yellow solid. TLC analysis, Rf 0.3 in diethyl ether/petroleum ether, 1/1, v/v.

2-[4-Bromo-phenyl]-4,5,6,7-tetrahydro-furo[3,2-c]pyridine (6, Rb=H)

Compound 5 (Rb=H, 166 g, 456 mmol) was suspended in concentrated hydrochloric acid (500 ml, 12N, 6 mol). The mixture was heated with 10° C. per 30 minutes to 80° C. The mixture starts to foam heavily, so allow enough volume in the starting reaction vessel. After 45 minutes, the mixture was cooled to 0° C. and neutralized with 50 wt % solution of NaOH (exothermic). After stirring overnight at room temperature, the resulting solid material was collected by filtration and washed with 250 ml 0.1M NaOH. The light brown material was purified by Soxhlet extraction in EtOAc giving 6 (Rb=H, 51 g, 38%) as a beige solid which was used in the next step without further purification. LC-MS (Method A): Rt 1.19, [M+H] 278.

3-[2-(4-Bromo-phenyl)-6,7-dihydro-4H-furo[3,2-c]pyridine-5-yl]-propionic acid t-butyl ester (7a, Rb=H)

Compound 6 (Rb=H, 1.46 g, 5 mmol) was suspended in methanol (30 ml) and DIPEA was added (0.91 ml, 1.05 eg). To the mixture was added t-butyl acrylate (0.88 ml, 1.2 eq) and the mixture was refluxed for 16 hrs. Conversion was checked by TLC analysis (diethyl ether/petroleum ether, 1/1, v/v). The solvents were evaporated and the residue was redissolved in EtOAc and extracted with a 5% solution of NaHCO$_3$. The organic layer was dried (MgSO$_4$), concentrated in vacuo and the residue was purified by silica gel column chromatography (diethyl ether/petroleum ether, 2/3 to 1/1, v/v) to give pure 7a (Rb=H, 1.75 g, 86%) as a white solid. LC-MS (Method A): Rt 1.38, [M+H] 407.

3-[2-(4-Hydroxy-phenyl)-6,7-dihydro-4H-furo[3,2-c]pyridine-5-yl]-propionic acid t-butyl ester (8a, Rb=H)

Compound 7a (Rb=H, 3.85 g, 9.5 mmol) was dissolved in toluene (80 ml) and to the solution was added potassium hydroxide (2 eq, 11.7N) and the solution was degassed. To the solution was added 2-di-t-butylphosphino-2',4',6'-triisopropylbiphenyl (0.24 g, 0.57 mmol, 0.06 eq) and tris-(dibenzylideneaceton)-dipalladium(0) (0.26 g, 0.28 mmol, 0.03 eq). The mixture was stirred at 60° C. for 1.25 hrs. The mixture was cooled to room temperature, diluted with EtOAc and washed with 5% $NaHCO_3$ solution (10 ml/mmol). The organic layers were dried on $MgSO_4$, filtered and concentrated in vacuo. The residue was purified by silica gel column chromatography (diethyl ether/petroleum ether, 1/1, v/v, Rf 0.1) to give pure compound 8a (Rb=H, 1.86 g, 57%) as a yellow solid. LC-MS (Method A): Rt 1.14, [M+H] 344.

3-{2-[4-(2-Fluoro-benzyloxy)-phenyl]-6,7-dihydro-4H-furo[3,2-c]pyridine-5-yl}-propionic acid t-butyl ester (9a, Ra=2F, Rb=H)

Compound 8a (Rb=H, 1.24 g, 3.61 mmol) was dissolved in N,N-dimethylacetamide (10 ml) and to this solution was added triphenylphosphine (1.33 g, 5.06 mmol, 1.4 eq), diisopropyl azodicarboxylate (1 ml, 5.05 mmol, 1.4 eq) and 2-fluorobenzyl alcohol (0.46 ml, 4.33 mmol, 1.2 eq). The mixture was stirred for 16 hrs at room temperature after which time TLC analysis (diethyl ether, Rf 0.3) showed complete reaction. The mixture was diluted with diethyl ether and washed with water (3×). The combined organic layers were dried on $MgSO_4$, filtered and concentrated in vacuo. The residue was purified by silica gel column chromatography (diethyl ether/petroleum ether, 1/1, v/v to 2/1, v/v) to give compound pure 9a (Ra=2F, Rb=H, 1.38 g, 84%) as an oil. LC-MS (Method A): Rt 1.46, [M+H] 452.

3-{2-[4-(2-Fluoro-benzyloxy)-phenyl]-6,7-dihydro-4H-furo[3,2-c]pyridine-5-yl}-propionic acid (33)

Compound 9a (Ra=2F, Rb=H, 1.38 g, 3.1 mmol) was dissolved in a solution of HCl in 1,4-dioxan (4N, 30 ml) and the mixture was stirred for 2 hrs at 35° C. The solvents were evaporated and diisopropyl ether (30 ml) was added to precipitate the product as the hydrochloric acid salt. The white solid material was filtered and dried in vacuo to give compound 33 (0.75 g, 54%) as a white solid. $^1$H NMR (400 MHz, DMSO-$d_6$): δ ppm 2.93 (t, J=7.6 Hz, 2H), 3.07 (bs, 2H), 3.28-3.55 (bs, 2H), 3.44 (t, J=7.6 Hz, 2H), 3.60-3.90 (bs, 2H), 4.06-4.56 (bs, 2H), 5.17 (s, 2H), 6.76 (s, 1H), 7.10 (d, J=8.8 Hz, 2H), 7.21-7.31 (m, 2H), 7.39-7.48 (m, 1H), 7.57 (t, J=7.5 Hz, 1H), 7.63 (d, J=8.8 Hz, 2H), 10.7-11.5 (bs, 1H), 12.3-13.2 (bs, 1H); LC-MS (Method A): Rt 1.39, [M+H] 396.

2-(4-Bromo-phenyl)-6,7-dihydro-4H-furo[3,2-c]pyridine-5-carboxylic acid t-butyl ester 10 (Rb=H)

To a suspension of compound 6 (Rb=H, 5 g, 17 mmol) in DCM (100 ml) were added DIPEA (2.92 ml, 1 eq), DMAP (0.1 g, 0.05 cq) and di-t-butyl dicarbonate (4.1 g, 18.8 mmol, 1.1 eq). The mixture was stirred at room temperature for 16 hrs after which time TLC analysis (DCM, Rf, 0.40) revealed complete reaction. The reaction mixture was washed with 5% ag. $NaHCO_3$ solution and the resulting water layers were extracted with DCM. The combined organic layers were dried on $MgSO_4$, filtered and concentrated in vacuo. The residue was purified by silica gel column chromatography (eluent: 100% DCM) to give compound 10 (Rb=H, 5.99 g, 92%) as an oil.

2-(4-Hydroxy-phenyl)-6,7-dihydro-4H-furo[3,2-c]pyridine-5-carboxylic acid t-butyl ester 11a (Rb=H)

Compound 10 (Rb=H, 11.77 g, 31 mmol) was dissolved in 1,4-dioxan/water, 1/1, v/v (200 ml) and to the solution was added potassium hydroxide (6.98 g, 124.5 mmol, 4 eq) and the solution was degassed. To the solution was added 2-di-t-butylphosphino-2',4',6'-triisopropylbiphenyl (0.53 g, 1.24 mmol, 0.04 eq) and tris-(dibenzylideneaceton)-dipalladium (0) (0.57 g, 0.62 mmol, 0.02 eq). The mixture was stirred at 80° C. for 16 hrs. The mixture was cooled to room temperature, diluted with EtOAc, acidified to pH 6 with 0.1N HCl and extracted with EtOAc. The organic layers were dried on $MgSO_4$, filtered and concentrated in vacuo. The residue was purified by silica gel column chromatography (eluent: DCM/MeOH, 1/0 to 99.5/0.5) to give compound 11 (Rb=H, 9 g, 90%) as a white solid.

2-[4-(4-Chloro-benzyloxy)-phenyl]-6,7-dihydro-4H-furo[3,2-c]pyridine-5-carboxylic acid t-butyl ester (12, Ra=4Cl, Rb=H)

Compound 11a (Rb=H, 2.0 g, 6.34 mmol) was dissolved in DCM/water, 2/1, v/v (30 ml) and to this solution was added sodium hydroxide (2N, 10 ml). To this mixture was added tetrabutylammonium bromide (0.2 g, 0.63 mmol, 0.1 eq) and 4-chlorobenzyl bromide (1.43 g, 6.98 mmol, 1.1 eg). The mixture was stirred for 16 hrs at room temperature after which time TLC analysis (100% DCM, Rf 0.55) showed complete reaction. The mixture was diluted with DCM (15 ml/mmol), the layers were separated and the water layer was extracted with DCM. The organic layers were dried on $MgSO_4$, filtered and concentrated in vacuo. The residue was purified by silica gel column chromatography (DCM/petroleum ether, 3/1 to 1/0, v/v) to give compound 12 (Ra=4Cl, Rb=H, 2.3 g, 82%) as a yellow oil. $^1$H NMR (400 MHz, $CDCl_3$) δ ppm 1.4 (s, 9H); 2.75 (bs, 2H); 3.75 (bs, 2H); 4.35 (bs, 2H); 5.05 (s, 2H); 6.4 (s, 1H), 6.94 (d, 1H); 7.30-755 (m, 7H).

2-[4-(4-Chloro-benzyloxy)-phenyl]-6,7-dihydro-4H-furo[3,2-c]pyridine (13, Ra=4Cl, Rb=H)

Compound 12 (Ra=4Cl, Rb=H, 2.3 g, 5.2 mmol) was dissolved in DCM (50 ml) and trifluoroacetic acid (4 ml, 10 eq) was added. The solution was refluxed for 16 hrs after which time TLC analysis (100% DCM, Rf 0.05) showed complete reaction. The mixture was neutralized with 5% aq. $NaHCO_3$. The mixture was extracted with DCM (3×) and the combined organic layers were washed with brine, dried on $Na_2SO_4$ and concentrated in vacuo to give crude 13 (Ra=4Cl, Rb=H, 1.79 g) which was used in the next step without further purification. LC-MS (Method A): Rt 1.49, [M+H] 340.

3-{2-[4-(4-Chloro-benzyloxy)-phenyl]-6,7-dihydro-4H-furo[3,2-c]pyridine-5-yl}-2-methyl-propionic acid t-butyl ester (9b, Ra=4Cl, Rb=H)

To a solution of compound 13a (0.25 g, 0.74 mmol) in DMF (5 ml) in a 25 ml pyrex bottle were added 1,8-diazabicyclo[5.4.0]undec-7-ene (0.33 ml, 2.21 mmol) and t-butyl-methacrylate (0.24 ml, 1.47 mmol). The mixture was heated at 140° C. for 16 hrs. The solution was cooled and 5% $NaHCO_3$ was added (10 ml) and extracted with diethyl ether/EtOAc, 1/1, v/v. The organic layer was washed with water (4×20 ml), dried on $MgSO_4$, concentrated in vacuo and the residue was purified by silica gel column chromatography (diethyl ether/petroleum ether, 9/1 to 4/1, v/v, Rf 0.65) to give pure 9b (Ra=4Cl, Rb=H, 0.1 g, 28%) as a colorless oil. LC-MS (Method A): Rt 1.88, [M+H] 482.

3-{2-[4-(4-Chloro-benzyloxy)-phenyl]-6,7-dihydro-4H-furo[3,2-c]pyridine-5-yl}-2-methyl-propionic acid (77)

Compound 9b (Ra=4Cl, Rb=H, 0.12 g, 0.25 mmol) was dissolved in a solution of HCl in 1,4-dioxan (4N, 2.8 ml) and the mixture was stirred for 16 hrs at room temperature. The solvent was evaporated and diisopropyl ether (30 ml) was added to precipitate the product as the hydrochloric acid salt. The white solid material was filtered and dried in vacuo to give compound 77 (0.09 g, 74%) as a white solid. $^1$H NMR (400 MHz, DMSO-$d_6$): δ ppm 1.29 (d, J=7.2 Hz, 3H), 3.05-3.17 (m, 3H), 3.23 (dd, J=5.4, 13.3 Hz, 1H), 3.51-3.68 (m, 3H), 4.24 (br. s., 2H), 5.16 (s, 2H), 6.73 (s, 1H), 7.08 (d, J=8.9 Hz, 2H), 7.42-7.53 (m, 4H), 7.61 (d, J=8.9 Hz, 2H), 10.4-13.1 (bs, 2H); $^{13}$C NMR (101 MHz, DMSO-$d_6$): δ ppm 16.42 (q, 1C), 20.36 (t, 1C), 35.17 (d, 1C), 48.74 (t, 1C), 49.57 (t, 1C), 56.96 (t, 1C), 68.60 (t, 1C), 102.92 (d, 1C), 113.06 (s, 1C), 115.41 (d, 1C), 123.20 (s, 1C), 124.87 (d, 1C), 128.41 (d, 1C), 129.42 (d, 1C), 132.46 (s, 1C), 136.01 (s, 1C), 145.10 (s, 1C), 152.99 (s, 1C), 157.85 (s, 1C), 174.95 (s, 1C). LC-MS (Method A): Rt 1.56, [M+H] 426.

2-[4-(Benzyloxy)-phenyl]-6,7-dihydro-4H-furo[3,2-c]pyridine-5-carboxylic acid t-butyl ester 12 (Ra=Rb=H)

Compound 11 (Rb=H, 0.84 g, 2.66 mmol) was dissolved in DCM/water, 2/1, v/v (30 ml) and to this solution was added sodium hydroxide (2N, 4.2 ml). To this mixture was added tetrabutyl-ammonium bromide (0.09 g, 0.27 mmol, 0.1 eq) and benzyl bromide (0.35 ml, 2.93 mmol, 1.1 eg). The mixture was stirred for 16 hrs at room temperature after which time TLC analysis (DCM/MeOH, 98/2, v/v, Rf 0.8) showed complete reaction. The mixture was diluted with DCM (100 ml), the layers were separated and the water layer was extracted with DCM. The organic layers were dried on MgSO$_4$, filtered and concentrated in vacuo. The residue was purified by silica gel column chromatography (DCM/petroleum ether, 3/1 to 1/0, v/v) to give compound 12 (Ra=Rb=H, 1.03 g, 95%) as a white solid. $^1$H NMR (400 MHz, CDCl$_3$) δ ppm 1.4 (s, 9H); 2.75 (bs, 2H); 3.75 (bs, 2H); 4.35 (bs, 2H); 5.05 (s, 2H); 6.35 (s, 1H); 6.98 (d, 2H); 7.30-7.55 (m, 7H).

2-[4-Benzyloxy-phenyl]-6,7-dihydro-4H-furo[3,2-c]pyridine (13, Ra=Rb=H)

Compound 12 (Ra=Rb=H, 1.03 g, 2.54 mmol) was dissolved in DCM (20 ml) and trifluoroacetic acid (1.5 ml) was added. The solution was refluxed for 16 hrs after which time TLC analysis (100% DCM, Rf 0.05) showed complete reaction. The mixture was neutralized with 5% aq. NaHCO$_3$ (40 ml) and extracted with DCM (3×50 ml) and the combined organic layers were washed with brine, dried on Na$_2$SO$_4$ and concentrated in vacuo to give compound 13 (Ra=Rb=H, 0.67 g, 86%) which was used in the next step without further purification. LC-MS (Method A): Rt 1.50, [M+H] 306.

3-{2-[4-Benzyloxy-phenyl]-6,7-dihydro-4H-furo[3,2-c]pyridine-5-yl}-butyric acid t-butyl ester (9c, Ra=Rb=H)

Compound 13 (Ra=Rb=H, 0.16 g, 0.52 mmol) was suspended in 1,2-dichloroethane (3.2 ml). To this suspension was added t-butylacetoacetate (0.09 ml, 0.52 mmol) and sodium triacetoxy borohydride (0.16 g, 0.73 mmol). The mixture was stirred at room temperature for 16 hrs, after which time another portion of t-butylacetoacetate (1 eq) and sodium triacetoxy borohydride (1.4 eq) were added together with a drop of acetic acid. After stirring for another 60 hrs, again a portion of t-butylacetoacetate (1 eq) and sodium triacetoxy borohydride (1.4 eq) were added and stirring was continued for 36 hrs. The solution was diluted with 5% NaHCO$_3$ (10 ml) and the mixture was extracted with DCM (3×100 ml). The combined organic layers were dried on Na$_2$SO$_4$, concentrated in vacuo and the residue was purified by silica gel column chromatography (diethyl ether/petroleum ether, 9/1 to 4/1, v/v) to furnish pure compound 9c (Ra=Rb=H, 0.06 g, 25%) as a white solid. LC-MS (Method A): Rt 1.68, [M+H] 448.

3-{2-[4-Benzyloxy-phenyl]-6,7-dihydro-4H-furo[3,2-c]pyridine-5-yl}-butyric acid (76)

Compound 9c (Ra=Rb=H, 0.08 g, 0.18 mmol) was dissolved in a solution of HCl in 1,4-dioxan (4 ml, 2N) and the mixture was stirred for 16 hrs at room temperature. The solvents were evaporated and the residue was co-evaporated with cyclohexane. Diisopropyl ether (30 ml) was added to precipitate the product as the hydrochloric acid salt, the white solid material was filtered and dried in vacuo to give compound 76 (0.06 g, 80%). $^1$H NMR (400 MHz, DMSO-$d_6$), δ ppm: 1.38 (d, J=6.6 Hz, 3H), 2.58-2.75 (m, 1H), 2.90-3.18 (m, 3H), 3.39-3.54 (m, 1H), 3.61-3.78 (m, 1H), 3.80-3.93 (m, 1H), 4.13-4.32 (m, 2H), 5.14 (s, 2H), 6.76 (s, 1H), 7.07 (d, J=8.8 Hz, 2H), 7.30-7.36 (m, 1H), 7.40 (s, 2H), 7.45 (s, 2H), 7.62 (d, J=8.8 Hz, 2H), 10.15-10.80 (m, 1H), 12.54-13.10 (m, 1H). LC-MS (Method A): Rt 1.46, [M+H] 392.

4-[2-(4-Bromo-phenyl)-6,7-dihydro-4H-furo[3,2-c]pyridine-5-yl]-butyric acid t-butyl ester (7d)

Compound 6 (Rb=H, 4.55 g, 16.3 mmol) was suspended in acetonitril (55 ml). To this suspension were added potassium carbonate (4.52 g, 32.7 mmol), t-butyl 4-bromobutanoate (4.38 g, 19.6 mmol, 1.2 cq) and potassium iodide (3.2 g, 19.6 mmol, 1.2 eq). The mixture was heated to reflux for 16 hrs after which time TLC analysis (diethyl ether/petroleum ether, 1/1, v/v, Rf 0.1) revealed complete reaction. The mixture was concentrated in vacuo and the residue was dissolved in EtOAc and washed with 5% NaHCO$_3$ (2×60 ml). The organic layer was dried on Na$_2$SO$_4$, concentrated in vacuo and the residue was purified by silica gel column chromatography (diethyl ether/petroleum ether, 1/1, v/v) to yield 7d (Rb=H, 4.94 g, 71%) as a yellow solid. LC-MS (Method A): Rt 1.37, [M+H] 420.

4-[2-(4-Hydroxy-phenyl)-6,7-dihydro-4H-furo[3,2-c]pyridine-5-yl]-butyric acid t-butyl ester (8d)

Compound 7d (Rb=H, 4.91 g, 11.68 mmol) was dissolved in toluene (100 ml) and to the solution was added potassium hydroxide (2 ml, 11.7N) and the solution was degassed. To the solution was added 2-di-t-butylphosphino-2',4',6'-triisopropylbiphenyl (0.27 g, 0.64 mmol, 0.06 eq) and tris-(dibenzylideneaceton)-dipalladium(0) (0.29 g, 0.32 mmol, 0.03 eq). The mixture was stirred at 60° C. for 1.25 hrs. The mixture was cooled to room temperature, diluted with EtOAc and washed with 5% NaHCO$_3$ solution (100 ml). The organic layers were dried on MgSO$_4$, filtered and concentrated in vacuo. The residue was purified by silica gel column chromatography (diethyl ether/petroleum ether, 1/1 to 1/0, v/v, Rf 0.1) to give pure compound 8d (Rb=H, 4.0 g) as a yellow solid. LC-MS (Method A): Rt 1.21, [M+H] 358.

4-{2-[4-(2-Fluoro-benzyloxy)-phenyl]-6,7-dihydro-4H-furo[3,2-c]pyridine-5-yl}-butyric acid t-butyl ester (9d)

Compound 8d (Rb=H, 0.43 g, 1.2 mmol) was dissolved in DCM/water, 2/1, v/v (5 ml) and to this solution was added sodium hydroxide (1.8 ml, 2N, 3 eq). To this mixture was added tetrabutylammonium bromide (0.1 eq) and 2F-benzyl bromide (1.32 mmol, 250 mg). The mixture was stirred for 16 hrs at room temperature after which time TLC analysis (diethyl ether, Rf 0.5) showed complete reaction. The mixture was diluted with DCM (15 ml), the layers were separated and the water layer was extracted with DCM. The organic layers were dried on $MgSO_4$, filtered and concentrated in vacuo. The residue was purified by silica gel column chromatography (diethyl ether/petroleum ether, 1/1 to 1/0, v/v to give compound 9d (Ra=2F, Rb=H) in a yield of 80%. LC-MS (Method A): Rt 1.49, [M+H] 466.

4-{2-[4-(2-Fluoro-benzyloxy)-phenyl]-6,7-dihydro-4H-furo[3,2-c]pyridine-5-yl}-butyric acid (35)

Compound 9d (Ra=2F, Rb=H, 0.3 g, 0.64 mmol) was dissolved in a solution of HCl in 1,4-dioxan (4N, 2.8 ml) and the mixture was stirred for 16 hrs at room temperature. The solvents were evaporated and diisopropyl ether (30 ml) was added to precipitate the product as the hydrochloric acid salt. The white solid material was filtered and dried in vacuo to give compound 35 (0.32 g, 95%) as a white solid. $^1$H NMR (400 MHz, DMSO-d) □ PPM: 1.69-1.83 (m, 2H), 2.18 (t, J=7.2 Hz, 2H), 2.81-2.91 (m, 2H), 3.02-3.13 (m, 2H), 3.23-3.36 (bs, 1H), 3.50-3.68 (bs, 1H), 3.89-4.05 (m, 1H), 4.15-4.29 (m, 1H), 4.98 (s, 2H), 6.58 (s, 1H), 6.91 (d, J=8.7 Hz, 2H), 7.02-7.12 (m, 2H), 7.21-7.29 (m, 1H), 7.38 (dt, J=7.7, 1.5 Hz, 1H), 7.44 (d, J=8.7 Hz, 2H), 9.80 (br.s., 1H), 11.37-13.06 (bs, 1H); LC-MS (Method A): Rt 1.37, [M+H] 410.

4-{2-[4-(2-Fluoro-benzyloxy)-2-fluoro-phenyl]-6,7-dihydro-4H-furo[3,2-c]-pyri-dine-5-yl}-butyric acid (73)

Compound 73 was prepared in a similar fashion as described for 35 starting from 2-bromo-1-(4-bromo-2-fluoro-phenyl)-ethanone. Compound 73: $^1$H NMR (400 MHz, DMSO-$d_6$), □ PPM: 1.92-2.04 (m, 2H), 2.38 (t, J=7.1 Hz, 2H), 3.02-3.13 (m, 2H), 3.17-3.28 (m, 2H), 3.44-3.92 (bs, 2H), 3.98-4.54 (bs, 2H), 5.21 (s, 2H), 6.70 (d, J=2.8 Hz, 1H), 7.00 (dd, J=8.9, 1.9 Hz, 1H), 7.12 (dd, J=13.4, 1.9 Hz, 1H) 7.23-7.32 (m, 2H) 7.41-7.50 (m, 1H) 7.56-7.63 (m, 1H) 7.69 (t, J=9.0 Hz, 1H), 10.06-10.93 (bs, 1H), 12.07-12.85 (bs, 1H); LC-MS (Method A): Rt 1.35, [M+H] 428.

2-(4-Bromo-phenyl)-oxazolo[4,5-c]pyridine (17, Rb=H)

To a cooled (0° C.) suspension of commercially available 4-hydroxy-3-amino-pyridine 14 (4 g, 36 mmol) in DCM (200 ml) were added triethyl amine (6.3 ml, 1.25 eq) and a solution of 4-bromo-benzoyl chloride (15, Rb=H, 8 g, 36 mmol, 1 eq, 0.3M in DCM). The reaction mixture was allowed to reach room temperature and the mixture was stirred for 16 hrs. The mixture was filtered, washed with DCM and ether to furnish crude 16 (Rb=H) as a solid material which was used in the next step without further purification. Hexachloroethane (10.2 g, 43 mmol, 2.5 eq) was dissolved in DCM (150 ml) and triphenyl phosphine (13.56 g, 51.69 mmol, 3 eq) and triethyl amine (19.2 ml, 137.8 mmol, 8 eq) was added. The mixture was stirred for 10 minutes at room temperature and crude compound 16 (Rb=H) was added slowly in 5 equal portions. The mixture was stirred at room temperature for 64 hrs after which time TLC analysis (DCM/MeOH, 97/3, v/v, Rf 0.3) revealed complete reaction. The solution was concentrated and the residue was suspended in DCM. The mixture was filtered and the residue washed with DCM and diethyl ether to give crude 17 (Rb=H) which was used in the next step without further purification.

2-(4-Bromo-phenyl)-5-methyl-4,5,6,7-tetrahydro-oxazolo[4,5-c]pyridine (19, Rb=H)

To a solution of compound 17 (Rb=H, 11.4 mmol) in DMF (95 ml) was added iodomethane (2.84 ml, 45.58 mmol, 4 eg) and the mixture was stirred for 16 hrs. The mixture was concentrated in vacuo and the residue was stirred in EtOAc to give crude 18 (Rb=H, 3.3 g, 69%) as a white solid. Compound 18 (Rb=H, 2.3 g, 5.5 mmol) was dissolved in methanol (55 ml) and the solution was cooled to 0° C. Sodium borohydride (0.42 g, 11 mmol, 2 cg) was added and the mixture was stirred at 0° C. for 2 hrs after which time it was allowed to reach room temperature and stirring was continued for 16 hrs. Water was added (4 ml) and the mixture was stirred for 5 minutes. The mixture was co-evaporated with acetonitril and the residue was purified by silica gel column chromatography (DMA 0.5) to yield compound 19 (Rb=H) in a yield of 61%.

2-(4-Bromo-phenyl)-4,5,6,7-tetrahydro-oxazolo[4,5-c]pyridine (20, Rb=H)

To a cooled (0° C.) solution of compound 19 (Rb=H, 0.95 g, 3.2 mmol) in 1,2-dichloroethane (32 ml) was added DIPEA (1.1 ml, 6.4 mmol, 2 eq). At 0° C., 1-chloroethylchloroformate (1.05 ml, 9.72 mmol, 3 eq) was added and the mixture was stirred for 10 minutes at 0° C. after which time the temperature was raised to reflux temperature. After 2 hrs, the mixture was concentrated in vacuo and the residue was dissolved in methanol (35 ml). The solution was stirred for 48 hrs at room temperature. The precipitate was filtered, the solid product was washed with diethyl ether to give compound 20 (Rb=H, 0.9 g, 88%). LC-MS (Method A): Rt 1.1, [M+H] 280.

3-[2-(4-Bromo-phenyl)-6,7-dihydro-H-oxazolo[4,5-c]pyridine-5-yl]-propionic acid t-butyl ester (21, Rb=H)

Compound 20 (Rb=H, 8 g, 22.8 mmol) was suspended in methanol (200 ml) and DIPEA was added (8.15 ml, 46.8 mmol, 2.05 eg). To the mixture was added t-butyl acrylate (3.97 ml, 27.4 mmol, 1.2 eq) and the mixture was refluxed for 120 rs. Conversion was checked by TLC analysis and after 16 and 64 hrs additional t-butyl acrylate (3.97 ml, 27.4 mmol, 1.2 eq) was added to push the reaction to completion. The solvents were evaporated and the residue was redissolved in EtOAc and extracted with a 5% solution of $NaHCO_3$. The organic layer was dried ($MgSO_4$), concentrated in vacuo and the residue was purified by silica gel column chromatography (eluent: diethyl ether/petroleum ether, 1/1, v/v) to give 21a (Rb=H, 8.8 g, 93%). LC-MS (Method A): Rt 1.38, [M+H] 408.

3-{2-[4-(Benzyloxy)-phenyl)]-6,7-dihydro-H-oxazolo[4,5-c]pyridine-5-yl}-propionic acid t-butyl ester (23a, Ra=Rb=H)

Compound 21a (Rb=H, 0.9 g, 2.21 mmol) was dissolved in degassed toluene (7 ml) and to the solution was added cesium carbonate (1.08 g, 3.3 mmol), benzyl alcohol (0.46 ml, 4.42 mmol, 2 eq), 2-di-t-butylphosphino-3,4,5,6-tetramethyl-2',4',6'-triisopropyl-1,1-biphenyl (25.5 mg, 0.05 mmol, 0.02 eq) and palladium(II) acetate (9.92 mg, 0.04 mmol, 0.02 eq). The mixture was stirred at 70° C. for 16 hrs. The mixture was cooled to room temperature, concentrated in vacuo and the residue was purified by silica gel column chromatography (diethyl ether/petroleum ether, 3/1, v/v) to give pure 23a (Ra=Rb=H, 0.71 g, 74%) as a white solid. LC-MS (Method A): Rt 1.46, [M+H] 435.

3-{2-[4-(Benzyloxy)-phenyl)]-6,7-dihydro-H-oxazolo[4,5-c]pyridine-5-yl}-propionic acid (47)

Compound 23a (Ra=Rb=H, 0.71 g, 1.63 mmol) was dissolved in a solution of HCl in 1,4-dioxan (4N, 12 ml, 30 eq) and the mixture was stirred for 16 hrs at 50° C. The solvents were evaporated and diethyl ether was added to precipitate the product. The white solid material was filtered and dried in vacuo to give compound 47 (0.67 g, 93%) as a white solid. $^1$H NMR (400 MHz, DMSO-d$_6$): □ ppm, 2.92 (t, J=7.1 Hz, 2H), 3.06-3.31 (bs, 2H), 3.57 (t, J=7.1 Hz, 2H), 3.50-3.61 (bs, 1H), 3.79-4.04 (bs, 1H), 4.21-4.42 (bs, 1H), 4.42-4.60 (bs, 1H), 5.20 (s, 2H), 7.16 (d, J=8.6 Hz, 2H), 7.35 (t, J=7.5 Hz, 1H), 7.41 (t, J=7.5 Hz, 2H), 7.49 (d, J=7.5 Hz, 2H), 7.93 (d, J=8.6 Hz, 2H), 10.31-10.84 (bs, 1H). LC-MS (Method A): Rt 1.32, [M+H] 379.

4-[2-(4-Bromo-phenyl)-6,7-dihydro-H-oxazolo[4,5-c]pyridine-5-yl]-butyric acid t-butyl ester (21d, Rb=H)

Compound 20 (Rb=H, 2.5 g, 7.92 mmol) was suspended in DMF (40 ml). To this suspension was added potassium carbonate (3.8 g, 27.7 mmol, 3.5 eq) and t-butyl 4-bromobutanoate (5.3 g, 23.7 mmol, 3 eq). The mixture was heated at 80° C. for 16 hrs after which time TLC analysis revealed complete reaction. The mixture was concentrated in vacuo and the residue was purified by silica gel column chromatography (eluent: diethyl ether/petroleum ether, 1/1, v/v to 100% diethyl ether) to yield 21d (Rb=H, 3.15 g, 94%) as a white solid.

4-{2-[4-(2,3-Difluoro-benzyloxy)-phenyl)]-6,7-dihydro-H-oxazolo[4,5-c]pyridine-5-yl}-butyric acid t-butyl ester (23d, Ra=2,3-diF, Rb=H)

Compound 21d (Rb=H, 0.6 g, 1.42 mmol) was dissolved in degassed toluene (5 ml) and to the solution was added cesium carbonate (0.7 g, 2.14 mmol), 2,3-difluoro-benzyl alcohol (0.32 ml, 2.85 mmol, 2 eq), 2-di-t-butylphosphino-3,4,5,6-tetramethyl-2',4',6'-triisopropyl-1,1-biphenyl (16.43 mg, 0.03 mmol, 0.02 eq) and palladium(II) acetate (6.39 mg, 0.03 mmol, 0.02 eq). The mixture was stirred at 70° C. for 16 hrs. The mixture was cooled to room temperature, concentrated in vacuo and the residue was purified by silica gel column chromatography (diethyl ether/petroleum ether, 2/1, v/v to 100% diethyl ether) to give pure 23d (Ra=2,3-diF, Rb=H, 0.48 g, 70%) as an oil.

4-{2-[4-(2,3-Difluoro-benzyloxy)-phenyl)]-6,7-dihydro-H-oxazolo[4,5-c]pyridine-5-yl}-butyric acid (57)

Compound 23d (Ra=2,3-diF, Rb=H, 0.46 g, 0.95 mmol) was dissolved in a solution of HCl in 1,4-dioxan (4N, 14 ml, 60 eq) and the mixture was stirred for 16 hrs at room temperature. The solvents were evaporated and diethyl ether was added to precipitate the product. The white solid material was filtered and dried in vacuo to give compound 57 (0.45 g, 99%) as a white solid. $^1$H NMR (400 MHz, DMSO-d$_6$): □□ ppm 2.08 (m., 2H), 2.41 (t, J=7.0 Hz, 2H), 3.00-3.29 (m, 2H), 3.31-3.40 (m, 2H), 3.48-3.70 (bs, 1H), 3.70-3.96 (bs, 1H), 4.18-4.38 (m, 1H), 4.38-4.61 (m, 1H), 5.26 (s, 2H), 7.16 (d, J=8.8 Hz, 2H), 7.19-7.25 (m, 1H), 7.28-7.39 (m, 2H), 7.94 (d, J=8.8 Hz, 2H), 10.37-10.88 (bs, 1H); LC-MS (Method A): Rt 1.16, [M+H] 429.

4-{2-[4-Benzyloxy-phenyl]-6,7-dihydro-H-oxazolo[4,5-c]pyridine-5-yl}-butyric acid (53)

Compound 53 was prepared in a similar fashion as described for the synthesis of 57 starting from 23d (Ra=Rb=H). $^1$H NMR (400 MHz, DMSO-d$_6$): □ ppm 2.01-2.17 (m, 2H), 2.42 (t, J=6.9 Hz 2H), 3.00-3.30 (m, 2H), 3.32-3.41 (m, 2H), 3.50-3.69 (m, 1H), 3.78-3.96 (m, 1H), 4.18-4.37 (m, 1H), 4.43-4.59 (m, 1H), 5.18 (s, 2H), 7.14 (d, J=8.8 Hz, 2H), 7.34 (t, J=7.9 Hz, 1H), 7.40 (t, J=7.9 Hz, 2H), 7.47 (d, J=7.9 Hz, 2H), 7.93 (d, J=8.8 Hz, 2H), 10.45-10.89 (bs, 1H); LC-MS (Method A): Rt 1.17, [M+H] 393.

4-{2-[4-(4-Trifluoromethyl-benzyloxy)-2-fluoro-phenyl]-6,7-dihydro-H-oxazolo[4,5-c]pyridine-5-yl}-butyric acid (85)

Compound 85 was prepared following route C starting from 2-fluoro-4-bromo-benzoyl chloride. $^1$H NMR (400 MHz, DMSO-d$_6$), □ ppm: 1.98-2.11 (m, 2H), 2.40 (t, J=7.1 Hz, 2H), 3.10-3.24 (m, 2H), 3.30-3.42 (m, 2H), 3.51-3.66 (bs, 1H), 3.79-3.97 (bs, 1H), 4.25-4.39 (m, 1H), 4.49-4.65 (m, 1H), 5.32 (s, 2H), 6.98-7.13 (m, 2H), 7.66-7.78 (m, 4H), 7.93 (t, J=8.6 Hz, 1H), 9.91-10.46 (bs, 1H); LC-MS (Method A): Rt 1.77, [M+H] 479.

4-{2-[4-(2-Fluoro-benzyloxy)-2-methyl-phenyl]-6,7-dihydro-H-oxazolo[4,5-c]pyridine-5-yl}-butyric acid (89)

Compound 89 was prepared following route C starting from 2-methyl-4-bromo-benzoyl chloride. $^1$H NMR (400 MHz, DMSO-d$_6$), □ ppm: 2.00-2.12 (m, 2H), 2.41 (t, J=7.1 Hz, 2H), 2.64 (s, 3H), 3.05-3.26 (m, 2H), 3.32-3.42 (m, 2H), 3.50-3.70 (bs, 1H), 3.79-3.95 (bs, 1H), 4.22-4.39 (m, 1H), 4.48-4.65 (m, 1H), 5.21 (s, 2H), 6.97-7.04 (m, 2H), 7.17-7.27 (m, 2H), 7.37-7.46 (m, 1H), 7.56 (dt, J=7.4, 1.4 Hz, 1H), 7.89 (d, J=8.5 Hz, 1H), 9.97-10.46 (bs, 1H); LC-MS (Method A): Rt 1.61, [M+H] 425.

4-{2-[4-(3,4-Dichloro-benzyloxy)-2-fluoro-phenyl]-6,7-dihydro-H-oxazolo[4,5-c]pyridine-5-yl}-butyric acid (227)

Compound 227 was prepared following route C starting from 2-fluoro-4-bromo-benzoyl chloride. $^1$H NMR (600 MHz, DMSO-d$_6$), □ ppm: 1.74 (q, J=7.1 Hz, 2H), 2.26 (t, J=7.1 Hz, 2H), 2.55 (t, J=7.1 Hz, 2H), 2.73-2.78 (m, 2H), 2.81 (t, J=5.3 Hz, 2H), 3.43 (br.s, 2H), 5.21 (s, 2H), 7.00 (dd, J=8.8, 2.5 Hz, 1H), 7.11 (dd, J=13.0, 2.5 Hz, 1H), 7.47 (dd, J=8.4, 2.0 Hz, 1H), 7.69 (d, J=8.3 Hz, 1H), 7.76 (d, J=1.9 Hz, 1H), 7.89 (t, J=8.3 Hz, 1H), 11.30-12.80 (bs, 1H); LC-MS (Method A): Rt 1.42, [M+H] 479.

4-{2-[4-(2-Fluoro-benzyloxy)-3-chloro-phenyl]-6,7-dihydro-H-oxazolo[4,5-c]pyridine-5-yl}-butyric acid (283)

Compound 283 was prepared following route C starting from 3-chloro-4-bromo-benzoyl chloride. $^1$H NMR (400 MHz, DMSO-d$_6$): □ ppm 1.69-1.80-1.74 (m, 2H), 2.27 (t, J=7.2 Hz, 2H), 2.55 (t, J=7.0 Hz, 2H), 2.73-2.79 (m, 2H), 2.81 (t, J=4.6 Hz, 2H), 3.43 (s, 2H), 5.32 (s, 2H), 7.25-7.33 (m, 2H), 7.42-7.50 (m, 2H), 7.58-7.65 (m, 1H), 7.88 (dd, J=8.7, 2.1 Hz, 1H), 7.93 (d, J=2.1 Hz, 1H), 11.0-13.0 (bs, 1H); LC-MS (Method B): Rt 1.99*, [M+H] 445.

4-{2-[4-(4-Chloro-benzyloxy)-3-fluoro-phenyl]-6,7-dihydro-H-oxazolo[4,5-c]pyridine-5-yl}-butyric acid (211)

Compound 211 was prepared following route C starting from 3-fluoro-4-bromo-benzoyl chloride. $^1$H NMR (400 MHz, DMSO-d$_6$) □ ppm: 1.95-2.06 (m, 2H), 2.38 (t, J=7.2 Hz, 2H), 3.09-3.20 (m, 2H), 3.23-3.32 (m., 2H), 3.44-3.53 (m, 1H), 3.76-3.86 (m, 1H), 4.20-4.32 (m, 1H), 4.43-4.52 (m, 1H), 5.28 (s, 2H), 7.43 (t, J=8.6 Hz, 1H), 7.51 (m, 4H), 7.76 (m, 2H), 10.65-11.02 (bs, 1H), 12.03-12.77 (bs, 1H); LC-MS (Method B): Rt 2.03*, [M+H] 445.

2-(4-Benzyloxy-phenyl)-oxazolo[4,5-c]pyridine (25, Ra=Rb=H)

To a cooled (0° C.) suspension of commercially available 4-hydroxy-3-amino-pyridine (14, 19.3 g, 175 mmol) in acetonitril (1500 ml) was added 4-benzyloxy-benzoic acid (24, Ra=Rb=H, 40 g, 175 mmol), triphenylphosphine (142.5 g, 543 mmol, 3.1 eq) and trichloroactonitril (54.5 ml, 543 mmol, 3.1 eq). The reaction mixture was allowed to reach room temperature and the mixture was stirred for 16 hrs at 80° C. The mixture was concentrated in vacuo and the residues was dissolved in DCM and washed with 2N NaOH (3×). The combined water layers were extracted with DCM and the organic layers dried (Na$_2$SO$_4$) to give crude 25 (Ra=Rb=H) as oil which was used in the next step without further purification.

2-(4-Benzyloxy-phenyl)-5-methyl-4,5,6,7-tetrahydro-oxazolo[4,5-c]pyridine (26, Ra=Rb=H)

To a solution of crude 25 (Ra=Rb=H, 117 mmol) in DMF (540 ml) was added iodomethane (29.35 ml, 471 mmol, 4 eg) and the mixture was stirred for 16 hrs. The mixture was concentrated in vacuo and the residue was stirred in EtOAc to give the quaternary salt of 25 a white solid, which dissolved in methanol (950 ml) and the solution was cooled to 0° C. Sodium borohydride (10.2 g, 268 mmol, 2.5 eg) was added and the mixture was stirred at 0° C. for 2 hrs after which time it was allowed to reach room temperature and stirring was continued for 64 hrs. Water was added (117 ml) and the mixture was stirred for 5 minutes. The mixture was concentrated in vacuo, the residues suspended in 2N NaOH (5 ml/mmol) and extracted with DCM (3×). The combined organic layers were dried (Na$_2$SO$_4$) and concentrated to give crude 26 (Ra=Rb=H) as a yellow solid which was used in the next step without further purification.

2-(4-Benzyloxy-phenyl)-4,5,6,7-tetrahydro-oxazolo[4,5-c]pyridine (27, Ra=Rb=H)

To a cooled (0° C.) solution of compound 26 (Ra=Rb=H, 35.2 g, 109.8 mmol) in 1,2-dichloroethane (880 ml) was added DIPEA (37.61 ml, 219.7 mmol, 2 eq) and 1-chloroethyl chloroformate (35.56 ml, 329.6 mmol, 3 eq) was added. The mixture was stirred for 10 minutes at 0° C. after which time the temperature was raised to reflux temperature. After 4 hrs, the mixture was allowed to reach room temperature and stirring was continued for 16 hrs. The mixture was concentrated in vacuo and the residue was dissolved in methanol (880 ml). The solution was stirred for 16 hrs at room temperature after which time TLC analysis revealed the reaction to be complete. Removal of the solvent resulted in the isolation of crude 27 (Ra=Rb=H) in an overall yield of 20% based on 25 (Ra=Rb=H).

3-[2-(4-Benzyloxy-phenyl)-4,5,6,7-tetrahydro-oxazolo[4,5-c]pyridine]-2-methyl-propionic acid t-butyl ester (28b)

To a solution of compound 27 (Ra=Rb=H, 13.45 g, 43.9 mmol) in DMF (270 ml) was added 1,8-diazabicyclo[5.4.0]undec-7-ene (3 eg) and t-butylmethacrylate (28.54 ml, 175.6 mmol, 4 eq). The mixture was heated at 125° C. for 100 hrs. The solution was cooled and 5% NaHCO$_3$ was added (15 ml/mmol) and extracted with diethyl ether/EtOAc, 1/1, v/v. The organic layer was washed with water (4×), dried on MgSO$_4$, concentrated in vacuo and the residue was purified by silica gel column chromatography (eluent: diethyl ether/petroleum ether, 1/2 to 3/1, v/v) to give 23b (Ra=Rb=H, 14.58 g, 74%) as an oil.

3-[2-(4-Benzyloxy-phenyl)-6,7-dihydro-H-oxazolo[4,5-c]pyridine-5-yl]-2-methyl-propionic acid (146)

Compound 23b (Ra=Rb=H, 0.45 g, 1 mmol) was dissolved in a solution of HCl in 1,4-dioxan (4N, 14 ml, 60 eq) and the mixture was stirred for 16 hrs at room temperature. The solvents were evaporated and diethyl ether was added to precipitate the product. The white solid material was filtered and dried in vacuo to give compound 146 (0.43 g, 99%) as a white solid. $^1$H NMR (400 MHz, DMSO-d$_6$), □ ppm: 1.28 (d, J=7.3 Hz, 3H), 3.07-3.20 (m, 3H), 3.26 (dd, J=13.2, 4.9 Hz, 1H), 3.60 (dd, J=13.2, 7.9 Hz, 1H), 3.66 (bs, 2H), 4.34 (br. s., 2H), 5.18 (s, 2H), 7.11-7.17 (m, 2H), 7.31-7.37 (m, 1H), 7.37-7.43 (m, 2H), 7.44-7.49 (m, 2H), 7.85-7.93 (m, 2H), 10.17-12.85 (bs, 1H); LC-MS (Method A): Rt 1.48, [M+H] 393.

3-{2-[4-(4-Trifluoromethyl-benzyloxy)-phenyl]-6,7-dihydro-H-oxazolo[4,5-c]pyridine-5-yl}-2-methyl-propionic acid (156)

Compound 156 was prepared following Route C. $^1$H NMR (400 MHz, DMSO-d$_6$): □ ppm: 1.29 (d, J=7.2 Hz, 3H), 3.09-3.21 (bs, 3H), 3.27 (dd, J=13.1, 5.3 Hz, 1H), 3.57-3.72 (dd, J=13.1, 7.3 Hz, 1H), 3.65-3.72 (bs, 2H), 4.34 (br. s., 2H), 5.33 (s, 2H), 7.21 (d, J=8.8 Hz, 2H), 7.68-7.74 (m, 2H), 7.75-7.81 (m, 2H), 7.93 (d, J=8.8 Hz, 2H), 10.50-12.32 (bs, 1H); $^{13}$C NMR (101 MHz, DMSO-d$_6$), □ PPM: 16.35 (q, 1C), 19.25 (t, 1C), 35.14 (d, 1C), 49.04 (br. t., 1C), 49.76 (br. t., 1C), 57.23 (t, 1C), 68.66 (t, 1C), 115.60 (d, 2C), 119.65 (s, 1C), 124.21 (s, $^1$JCF=272.5 Hz, 1C), 125.34 (d, $^3$JCF=3.6 Hz, 2C), 127.63 (d, 2C), 128.05 (d, 2C), 128.51 (s, $^2$JCF=31.7 Hz, 1C), 128.63 (s, 1C), 141.51 (s, 1C), 142.86 (s, 1C), 160.11 (s, 1C), 160.76 (s, 1C), 174.95 (s, 1C); LC-MS (Method A): Rt 1.82, [M+H] 461.

3-{2-[4-(4-Chloro-benzyloxy)-phenyl]-6,7-dihydro-H-oxazolo[4,5-c]pyridine-5-yl}-2-methyl-propionic acid (157)

Compound 157 was prepared following route C. $^1$H NMR (400 MHz, DMSO-$d_6$), □ ppm: 1.19 (d, J=7.4 Hz, 3H), 3.00-3.12 (m, 3H), 3.18 (dd, J=13.2, 5.3 Hz, 1H), 3.52 (dd, J=13.2, 7.1 Hz, 1H), 3.56-3.66 (bs, 2H), 4.24 (br. s., 2H), 5.11 (s, 2H), 7.08 (d, J=9.0 Hz, 2H), 7.35-7.43 (m, 4H), 7.81 (d, J=9.0 Hz, 2H), 10.57-11.92 (bs, 1H); $^{13}$C NMR (101 MHz, DMSO-$d_6$), □ PPM: 16.44 (q, 1C), 19.19 (t, 1C), 35.09 (d, 1C), 49.1 (br. t., 1C), 49.6 (br. t., 1C), 57.17 (t, 1C), 68.72 (t, 1C), 115.59 (d, 2C), 119.50 (s, 1C), 127.60 (d, 2C), 128.45 (d, 2C), 128.52 (s, 1C), 129.51 (d, 2C), 132.58 (s, 1C), 135.69 (s, 1C), 142.79 (s, 1C), 160.22 (s, 1C), 160.80 (s, 1C), 174.92 (s, 1C); LC-MS (Method A): Rt 1.72, [M+H] 427.

3-{2-[4-(4-(2,3-Difluoro-benzyloxy)-phenyl]-6,7-dihydro-H-oxazolo[4,5-c]pyridine-5-yl}-butyric acid (175)

Compound 175 was prepared following route C. $^1$H NMR (400 MHz, DMSO-$d_6$), □□ ppm: 1.27 (d, J=6.6 Hz, 3H), 2.5-2.6 (m, 1H), 2.8-3.1 (m, 3H), 3.1-3.5 (bs, 2H), 3.6-3.7 (bs, 1H), 3.9-4.1 (bs, 2H), 5.28 (s, 2H), 7.0-7.2 (m, 2H), 7.2-7.3 (m, 1H), 7.4-7.5 (m, 2H), 7.9-8.0 (m, 2H), 12.16 (br. s., 1H); LC-MS (Method A): Rt 1.3, [M+H] 429.

3-{2-[4-(4-Trifluoromethyl-benzyloxy)-2-fluoro-phenyl]-6,7-dihydro-H-oxazolo[4,5-c]pyridine-5-yl}-2-methyl-propionic acid (271)

Compound 271 was prepared following route C. $^1$H NMR (400 MHz, DMSO-$d_6$), □ ppm: 1.29 (d, J=7.2 Hz, 3H), 3.06-3.36 (m, 4H), 3.51-3.68 (m, 2H), 3.70-3.90 (bs, 1H), 4.18-458 (bs, 2H), 5.33 (s, 2H), 7.03 (dd, J=8.7, 2.2 Hz, 1H), 7.10 (dd, J=12.9, 2.2 Hz, 1H), 7.65-7.71 (m, 2H), 7.73-7.77 (m, 2H), 7.92 (t, J=8.7 Hz, 1H), 11.01 (br. s., 1H); LC-MS (Method A): Rt 1.56, [M+H] 479.

2-(4-Bromo-phenyl)-6,7-dihydro-H-oxazolo[4,5-c]pyridine-5-carboxylic acid t-butyl ester (28, Rb=H)

To a suspension of compound 20 (Rb=H, 14.3 g, 48.2 mmol) in DCM (300 ml) were added DIPEA (1 eq) and di-t-butyl dicarbonate (11.59 g, 53 mmol, 1.1 eq). The mixture was stirred at room temperature for 16 hrs after which time TLC analysis revealed complete reaction. The mixture was concentrated in vacuo to give crude compound pure 28 (Rb=H) which was used in the next step without further purification.

2-(4-Hydroxy-phenyl)-6,7-dihydro-H-oxazolo[4,5-c]pyridine-5-carboxylic acid t-butyl ester (29, Rb=H)

Compound 28 (Rb=H, 9 g, 20.4 mmol) was dissolved in 1,4-dioxan (90 ml) and to the solution was added potassium hydroxide (4.58 g, 81 mmol, in 90 ml water) and the solution was degassed. To the solution was added 2-di-t-butylphosphino-2',4',6'-triisopropylbiphenyl (346 mg, 0.82 mmol, 0.04 eq) and tris-(dibenzylideneaceton)-dipalladium(0) (373.5 mg, 0.41 mmol, 0.02 eq). The mixture was stirred at 80° C. for 16 hrs after which time LC-MS analysis showed that the conversion was complete. The mixture was cooled to room temperature, diluted with EtOAc, acidified to pH 6 with 0.1N HCl and extracted with EtOAc. The organic layers were dried on MgSO$_4$, filtered and concentrated in vacuo. The residue was purified by silica gel column chromatography (DCM/MeOH, 97/3, v/v) to give compound pure 29 (Rb=H, 6 g, 83%).

2-[4-(4-Trifluoromethyl-benzyloxy)-phenyl)-6,7-dihydro-H-oxazolo[4,5-c]pyridine-5-carboxylic acid t-butyl ester (30, Ra=4CF$_3$, Rb=H)

Compound 29 (Rb=H, 6 g, 17 mmol) was dissolved in DCM/water, 2/1, v/v (78 ml/mmol) and to this solution was added sodium hydroxide (27 ml, 2N, 3 eq). To this mixture was added tetrabutylammonium bromide (549 mg, 0.1 eq) and 4-trifluoromethyl-benzyl bromide (4.48 g, 18.75 mmol, 1.1 eq). The mixture was stirred for 16 hrs at room temperature after which time LC-MS analysis showed complete reaction. The mixture was diluted with DCM (200 ml), the layers were separated and the water layer was extracted with DCM. The organic layers were dried on MgSO$_4$, filtered and concentrated in vacuo. The residue was purified by silica gel column chromatography (eluent: EtOAc/petroleum ether, 1/3) to give compound pure 30 (Rb=H, 9.0 g, 96%) as a colorless foam.

2-[4-(4-Trifluoromethyl-benzyloxy)-phenyl)-6,7-dihydro-H-oxazolo[4,5-c]pyridine (30, Ra=4CF$_3$, Rb=H)

Compound 30 (9.6 g, 18.5 mmol) was dissolved in DCM (150 ml) and trifluoroacetic acid (8.5 ml, 111 mmol, 6 eq) was added. The solution was refluxed for 16 hrs after which time TLC analysis showed complete reaction. The mixture was neutralized with 5% aq. NaHCO$_3$. The mixture was extracted with DCM (3×) and the combined organic layers were washed with brine, dried on Na$_2$SO$_4$ and concentrated in vacuo to give compound 27 (Ra=4CF$_3$, Rb=H) which was used in the next step without further purification.

3-{2-[4-(4-Trifluoromethoxybenzyloxy)-phenyl]-6,7-dihydro-H-oxazolo[4,5-c]pyridine-5-yl}-cyclobutane carboxylic acid (306)

Compound 27 (Ra=4CF$_3$, Rb=H 0.71 g, 1.8 mmol) was suspended in 1,2-dichloroethane (40 ml). To this suspension was added 3-oxocyclobutanecarboxylic acid (0.27 g, 2.34 mmol, 1.3 eq) and sodium triacetoxy borohydride (0.61 g, 2.88 mmol, 1.6 eq). The mixture was stirred at room temperature for 16 hrs after which time TLC analysis revealed complete reaction. The solution was diluted with 5% NaHCO3 (15 ml/mmol) and the mixture was extracted with DCM. The combined organic layers were dried on Na$_2$SO$_4$, concentrated in vacuo and the residue was purified by silica gel column chromatography to furnish a mixture of cis and trans stereoisomers in a ratio of 2 to 1. A second silica gel column chromatography purification (DCM/MeOH, 9/1, v/v) resulted in the isolation of two enriched stereoisomer fractions. Compound 307-cis (Rf, 0.2, 0.46 g, 51%, cis/trans=95/5) and 306-trans (Rf 0.25, 0.21 g, 25%, cis/trans=5/95). 307-cis: $^1$H NMR (400 MHz, DMSO-$d_6$): □ ppm 1.92-2.05 (m, 2H); 2.26-2.37 (m, 2H); 2.68 (t, J=4.5 Hz, 2H); 2.70-2.79 (m, 3H); 2.89-3.00 (m, 1H); 3.30-3.41 (bs, 1H); 5.21 (s, 2H) 7.14 (d, J=8.8 Hz, 2H); 7.41 (d, J=8.5 Hz, 2H); 7.61 (d, J=8.5 Hz, 2H); 7.87 (d, J=8.8 Hz, 2H); 12.15 (br. s., 1H); 306-trans: $^1$H NMR (400 MHz, DMSO-$d_6$) ⸺ ppm: 2.10-2.21 (m, 2H); 2.22-2.34

(m, 2H); 2.67 (t, J=4.8 Hz, 2H); 2.71-278 (m., 2H); 2.84-2.95 (m, J=9.6 Hz, 1H); 3.17 (quin, J=7.4 Hz, 1H); 3.31-3.40 (bs, 2H); 5.21 (s, 2H); 7.14 (d, J=8.8 Hz, 2H); 7.41 (d, J=8.5 Hz, 2H); 7.61 (d, J=8.5 Hz, 2H); 7.87 (d, J=8.8 Hz, 2H); 12.20 (br. s., 1H). LC-MS Rt 1.41, [M+H]=489.

3-{2-[4-(3,4-Difluorobenzyloxy)-phenyl]-6,7-dihydro-H-oxazolo[4,5-c]pyridine-5-yl}-cyclobutane carboxylic acid (277)

Compounds 278-cis and 277-trans were prepared as described for 306. 278-cis: $^1$H NMR (400 MHz, DMSO-$d_6$): ☐ppm 1.93-2.04 (m, 2H) 2.26-2.36 (m, 2H) 2.68 (t, J=4.8 Hz, 2H) 2.70-2.80 (m, 3H) 2.88-3.00 (m, 1H) 3.33-3.40 (bs, 2H) 5.16 (s, 2H) 7.14 (d, J=8.8 Hz, 2H) 7.29-7.38 (m, 1H) 7.47 (dt, J=10.7, 8.4 Hz, 1H) 7.56 (ddd, J=11.5, 8.0, 2.0 Hz, 1H) 7.87 (d, J=8.8 Hz, 2H) 12.15 (br. s., 1H); LC-MS (method A): Rt 1.33, [M+H]=441; 277-trans: $^1$H NMR (400 MHz, DMSO-$d_6$): ☐ ppm 2.09-2.20 (m, 2H) 2.23-2.31 (m, 2H) 2.67 (t, J=4.5 Hz, 2H) 2.70-2.77 (m, 2H) 2.84-2.93 (m, 1H) 3.12-3.22 (m, 1H) 3.32-3.39 (bs, 2H) 5.16 (s, 2H) 7.14 (d, J=8.8 Hz, 2H) 7.30-7.37 (m, 1H) 7.47 (dt, J=10.8, 8.4 Hz, 1H) 7.56 (ddd, J=11.4, 8.0, 1.9 Hz, 1H) 7.87 (d, J=8.8 Hz, 2H) 12.20 (br. s., 1H); LC-MS (method A): Rt 1.31, [M+H]=441.

3-Bromo-N-benzyloxycarbonyl-4-piperidone (502)

To a cooled (0° C.) solution of N-benzyloxycarbonyl-4-piperidone (501, 27.3 g 117 mmol) in DCM (3 ml/mmol) was added DIPEA (25.5 ml, 146.2 mmol, 1.25 eg) and trimethylsilyl trifluoromethane sulfonate (25.4 ml, 141 mmol, 1.2 eg). The mixture was stirred for 30 minutes at 0° C. Next, N-bromosuccinimide (21.2 g, 119.3 mml, 1.02 eg) was added and stirring was continued for 16 hrs at room temperature. The reaction mixture was washed with 5% NaHCO$_3$ and the organic layer was dried (MgSO$_4$) and subsequently concentrated under reduced pressure. The resulting oil was purified by silica gel chromatography (diethyl ether/petroleum ether, 1/1 to 1/0, v/v, Rf 0.1) giving 502 in a yield of 90% as a yellow oil.

2-(4-Methoxy-phenyl)-6,7-dihydro-4H-thiazolo[5,4-c]pyridine-5-carboxylic acid benzyl ester (504)

Compound 502 (2.0 g, 6.5 mmol) was dissolved in ethanol (20 ml). To the solution was added 4-methoxythiobenzamide (503, 1.09 g, 6.5 mmol, 1 eq) and the yellow mixture was refluxed for 17 hrs after which time TLC analysis showed full conversion of 502. The reaction mixture was concentrated in vacuo and the residue was dissolved in EtOAc, washed with 5% Na$_2$SO$_4$ and the organic layer was dried (MgSO$_4$) and subsequently concentrated under reduced pressure. The resulting oil was purified by silica gel chromatography (diethyl ether, Rf 0.3) giving compound 504 in a yield of 49% as a colorless oil. Compounds having a Rb substitute can be prepared by choosing a properly substituted (Rb)-4-methoxythiobenzamide (503).

4-(4,5,6,7-Tetrahydro-thiazolo[5,4-c]pyridine-2-yl)-phenol 505

Compound 504 (18.0 g, 47.3 mmol) was dissolved in ethanol (300 ml). To the cooled (−78° C.) solution was added boron tribromide (5 eg, 236 mmol) dropwise. After one hour cooling was removed and the mixture was stirred 16 hrs at room temperature. The reaction was quenched with MeOH, the mixture was concentrated in vacuo to give compound 505 as an oil which was used in the next step without further purification.

General Procedure for the Synthesis of Compounds 508

Compounds 508 are prepared starting from compounds 505 in a similar fashion as described for the synthesis of compounds 7 and 21 (see schemes 1-4). As a typical example we describe the synthesis of compound 508 (Ra=F, Rb=H, Rc=C2).

3-[2-(4-(Hydroxy-phenyl)-6,7-dihydro-4H-thiazolo [5,4-c]pyridine-5-yl]-propionic acid t-butyl ester (506, Rb=H, Rc=C2)

To a suspension of 505 (Rb=H, 5.8 g, 25.1 mmol) in MeOH (100 ml) and DIPEA (5.1 ml, 30.1 mmol, 1.2 eq) was added t-butyl acrylate (4.4 ml, 30.1 mmol, 1.2 eq) and the mixture was refluxed for 16 hrs after which time TLC analysis (diethyl ether, Rf 0.2) showed full conversion of 505. The reaction mixture was concentrated in vacuo and the residue was dissolved in EtOAc, washed with 5% NaHCO3 and the organic layer was dried (Na$_2$SO$_4$) and subsequently concentrated under reduced pressure. The resulting oil was purified by silica gel chromatography (diethyl ether) giving compound 506 (Rb=H, Rc=C2) in a yield of 79% as a white solid material.

3-[2-(4-(2-Fluoro-benzyloxy)-phenyl)-6,7-dihydro-4H-thiazolo[5,4-c]pyridine-5-yl]-propionic acid t-butyl ester (507, Ra=2F, Rb=H, Rc=C2)

To a suspension of 506 (Rb=H, Rc=C2, 0.5 g, 1.4 mmol) in DMA (4 ml) was added triphenyl phosphine (0.45 g, 1.7 mmol, 1.25 eg), diisopropyl azodicarboxylate (0.33 ml, 1.7 mmol, 1.25 eq) and 2-fluoro benzyl alcohol (0.17 ml, 1.56 mmol, 1.15 eg) and the mixture was stirred at room temperature for 16 hrs. The reaction mixture was diethyl ether (150 ml) and washed with 3×50 ml water. The combined organic layers were dried (Na$_2$SO$_4$) and subsequently concentrated under reduced pressure. The resulting oil was purified by silica gel chromatography (diethyl ether/petroleum ether, 2/1, v/v) giving compound 507 (Ra=2F, Rb=H, Rc=C2) in a yield of 67% as a white solid material.

3-[2-(4-(2-Fluoro-benzyloxy)-phenyl)-6,7-dihydro-4H-thiazolo[5,4-c]pyridine-5-yl]-propionic acid (38, Ra=2F, Rb=H, Rc=C2)

Compound 507, Ra=2F, Rb=H, Rc=C2, 0.43 g, 0.9 mmol) was dissolved in 4N HCl in dioxane (10 ml). The mixture was stirred for 16 hrs at room temperature. The mixture was concentrated in vacuo and the resulting solid was washed with diisopropyl ether to give 38 as a white solid (Ra=2F, Rb=H, Rc=C2, 0.42 g, 97%). Compound 38: $^1$H NMR (400 MHz, DMSO-$d_6$), ⌣ ppm 2.88-3.03 (m, 2H), 3.06-3.14 (m, 1H), 3.20 (m, 1H), 3.48 (broad signal, 3H), 3.73-3.87 (m, 1H), 4.44 (bd, J=15.9, 6.0 Hz, 1H), 4.72 (b, J=15.9 Hz, 1H), 5.22 (s, 2H), 7.16 (d, J=8.6 Hz, 2H), 7.23-7.32 (m, 2H), 7.41-7.49 (m, 1H), 7.59 (dt, J=7.6, 1.5 Hz, 1H), 7.87 (d, J=8.6 Hz, 2H), 11.63 (br. s., 1H); LC-MS (Method A): Rt 1.3, [M+H] 473.

4-Bromo-N-(4-chloro-pyridin-3-yl)-benzamide (510)

A mixture of 4-amino-3-chloropyridine (509, 5.9 g, 46.2 mmol), 4-bromobenzoyl chloride (15, 11.15 g, 50.8 mmol) and potassium carbonate (22.4 g, 161.7 mmol) in acetonitril (150 ml) was refluxed for 24 hrs. The reaction mixture was concentrated in vacuo, redissolved in DCM and the solution was washed with water. The organic layer was dried (MgSO$_4$), concentrated and the resulting oil was purified by silica gel column chromatography (DCM/MeOH, 99/1, v/v, Rf 0.2) to give pure 510 (10.4 g, 72%) as an oil. When a substituted compound 15 is used, the Rb in compound 510 is introduced.

2-(4-Bromo-phenyl)-thiazolo-[4,5c]-pyridine (511)

Compound 510 (10.4 g, 33.4 mmol) was suspended in toluene (400 ml) and Lawesson's reagent (9.4 g, 23.4 mmol, 0.7 eq) was added and the mixture was refluxed for 24 hrs after which time TLC analysis (DCM/MeOH, 97/3, v/v, Rf 0.7) revealed the reaction to be complete. The mixture was concentrated in vacuo and to the oil was added NaHCO$_3$ (5% solution, 200 ml) and the suspension was extracted with DCM (3×200 ml). The combined organic layers was dried over MgSO$_4$, concentrated and the oil was purified by silica gel column chromatography (DCM/MeOH, 99/1 to 97/3, v/v) to give pure 511 (8.7 g, 89%) as an oil.

2-(4-Benzyloxy-phenyl)-4,5,6,7-tetrahydro-thiazolo-[4,5c]-pyridine (518)

Compounds 518 were obtained starting from 511 in a similar fashion as described for the synthesis of compounds 27 in schemes 4 and 7. The appropriate tails Rc could be linked to 518 in a similar fashion as described for compounds 27.

4-{2-[4-(3,5-Difluoro-benzyloxy)-phenyl]-6,7-dihydro-4H-thiazolo-[4,5c]-pyridin-5-yl}-butyric acid (446, Ra=3,5-F, Rb=H, Rc=C3)

Compound 519 (Ra=3,5-F, Rb=H, Rc=C3, 0.79 g, 1.58 mmol) was dissolved in 4N HCl in dioxan (25 ml) was stirred for 18 hrs at 50° C. and for 70 hrs at room temperature. The mixture was concentrated in vacuo and the resulting oil was stirred in diethyl ether to yield 446 as a white solid (0.72 g, 94%). $^1$H NMR (400 MHz, DMSO-d$_6$): □ ppm: 2.03-2.15 (m, 2H), 2.40 (t, J=7.3 Hz, 2H), 3.12-3.22 (m, 1H), 3.32 (broad signal, 3H), 3.40-3.51 (m, 1H), 3.75-3.90 (m, 1H), 4.36 (dd, J=15.2, 6.8 Hz, 1H), 4.59 (d, J=15.2 Hz, 1H), 5.21 (s, 2H), 7.05 (tt, J=9.0, 2.3 Hz, 1H), 7.09-7.18 (m, 4H), 7.84 (d, J=8.9 Hz, 2H), 11.17 (br. s., 1H); Rt 1.33, [M+H] 502.

2-{2-[4-(3,5-Difluoro-benzyloxy)-phenyl]-6,7-dihydro-H-oxazolo[4,5-c]pyridine-5-yl}-acetic acid (463)

2-[4-(3,5-difluoro-benzyloxy)-phenyl]-4,5,6,7-tetrahydro-oxazolo[4,5-c]pyridine (27, Ra=3,5-diF, Rb=H) was synthesized following route C as described above. Compound 27 (Ra=3,5-diF, Rb=H, 0.4 g, 1.17 mmol) was dissolved in acetonitril (20 ml). To the solution was added DIPEA (0.51 ml, 2.9 mmol, 2.5 eq) and t-butyl bromoacetate (0.19 ml, 1.29 mmol, 1.1 eq). The mixture was refluxed for 6 hrs after which time LCMS analysis showed the reaction to be complete. The mixture was concentrated in vacuo, water was added and the suspension was extracted with DCM (3×200 ml). The combined organic layers was dried over MgSO$_4$, concentrated and the oil was purified by silica gel column chromatography (diethyl ether/petroleum ether, 3/1, v/v). The resulting oil was suspended in 4N HCl in dioxan (20 ml). The mixture was stirred at 45° C. for 5 hrs and at room temperature for 16 hrs. The mixture was concentrated in vacuo to give a white solid. The solid material was washed 3 times with diethyl ether to give 463 (0.39 g, 91%) as a white solid. $^1$H NMR (400 MHz, DMSO-d$_6$): □ ppm: 3.10-3.20 (m., 2H), 3.70-3.80 (m., 2H), 4.31 (s, 2H), 4.44 (s, 2H), 5.22 (s, 2H), 7.02-7.10 (m, 1H), 7.13-7.20 (m, 4H), 7.92 (d, J=8.8 Hz, 2H), 9.53-12.44 (br.s., 1H); Rt 1.51; [M+H] 401.

2-{2-[4-(3,5-Difluoro-benzyloxy)-phenyl]-6,7-dihydro-H-oxazolo[4,5-c]pyridine-5-yl}-propionic acid (464)

Compound 27 (Ra=3,5-diF, Rb=H, 0.4 g, 1.17 mmol) was dissolved in acetonitril (20 ml). To the solution was added DIPEA (0.51 ml, 2.9 mmol, 2.5 eq) and t-butyl 2-bromo-propionic ester (0.27 gl, 1.29 mmol, 1.1 eq). The mixture was refluxed for 24 hrs after which time LCMS analysis showed the reaction to be complete. The mixture was concentrated in vacuo, water was added and the suspension was extracted with DCM (3×200 ml). The combined organic layers were dried on MgSO$_4$, concentrated and the oil was purified by silica gel column chromatography (diethyl ether/petroleum ether, 3/2, v/v, Rf 0.3). The resulting oil was suspended in 4N HCl in dioxan (20 ml). The mixture was stirred at 45° C. for 5 hrs and at room temperature for 16 hrs. The mixture was concentrated in vacuo to give a white solid. The solid material was washed 3 times with diethyl ether to give 464 (0.41 g, 89%) as a white solid. $^1$H NMR (400 MHz, DMSO-d$_6$): □ ppm, 1.66 (d, J=7.1 Hz, 3H), 3.17 (br. s., 2H), 3.74 (br. s., 2H), 4.33-4.52 (m, 4H), 5.22 (s, 2H), 7.02-7.11 (m, 1H), 7.13-7.25 (m, 4H), 7.92 (d, J=8.8 Hz, 2H); Rt 1.53, [M+H] 415.

3-{2-[4-(3,5-Difluoro-benzyloxy)-phenyl]-6,7-dihydro-4H-oxazolo[4,5-c]-pyridin-5-yl}-cyclopentane carboxylic acid (465, 1/1 cis-trans mixture)

Compound 27 (Ra=3,5-diF, Rb=H, 0.1 g, 0.29 mmol) was dissolved in 1,2-dichloroethane (5 ml). To the solution was added 3-oxo-cyclopentane-carboxylic acid (0.05 g, 0.41 mmol, 1.4 eq), sodium triacetoxy borohydride (0.11 g, 0.53 mmol, 1.8 eq) and AcOH (0.03 ml, 0.58 mmol, 2 eq). The mixture was stirred for 16 hrs after which time LCMS analysis showed the reaction to be complete. To the mixture was added a saturated solution of NH$_4$Cl and the mixture was extracted with DCM. The combined organic layers was concentrated in vacuo and the oil was purified by silica gel column chromatography (DCM/MeOH, 9/1, v/v) to give compound 465 as a cis/trans mixture in a ratio of 1/1.
Rt 1.27, [M+H] 455.

4-{2-[4-(2,3-Difluoro-benzyloxy)-2-methyl-phenyl]-6,7-dihydro-4H-oxazolo-[4,5c]-pyridin-5-yl}-pentanoic acid (393)

Compound 22 (Rb=2Me, Rc=H) was prepared by stirring 29 (Rb=2Me) in a mixture of TFA and DCM for 16 hrs. The solvents were evaporated to give crude 22 (Rb=2Me, Rc=H) as an oil which was used in the next step without further purification. A SCX-2 column was used to make the free base of compound 22 (Rb=2Me, Rc=H, 1 g, 4.3 mmol), which was dissolved in MeOH. To this solution was added ethyl levulinate (2.46 ml, 17.4 mmol, 4 eq), AcOH (0.5 ml, 8.7 mmol, 2 eq) and palladium hydroxide on carbon. The reaction mixture was shaken at a pressure of 4 atm of hydrogen. After 16 hrs, ELSD showed that the reaction was not yet complete. Another portion of ethyl levulinate (2.46 ml, 17.4 mmol, 4 eq) and palladium hydroxide on carbon was added and hydrogenation at 4 atm was continued for 72 hrs. The mixture was degassed, filtered over Hyflo and the residue was washed with MeOH.

The filtrate was concentrated in vacuo and the resulting oil was purified by silica gel column chromatography to give 522 (Rb=2Me, Rc=xCH$_2$(CH$_3$)CH$_2$CH$_2$C(=O)OEt) in an yield of 41%. Subsequent benzylation of 522 with 2,3-di-fluoro-benzyl bromide was performed in a similar fashion as described for the compounds of Schemes 1-5 giving compound 523. Finally, the latter was dissolved in a solution of sodium hydroxide in ethanol (18 ml, 0.3M) and the solution was stirred at 50° C. for 16 hrs. The mixture was concentrated in vacuo and the residue was stirred in diethyl ether to give 393 as a white solid (Ra=2,3-diF, Rb=2Me, Rc=CH$_2$(CH$_3$)CH—$_2$CH$_2$C(=O)OH). $^1$H NMR (400 MHz, DMSO-d$_6$): □ ppm 1.40 (d, J=5.9 Hz, 3H), 1.74-1.93 (m, 1H), 2.15-2.30 (m, 1H), 2.31-2.50 (m, 3H), 2.63 (s, 3H), 3.04-3.15 (m, 1H), 3.22-3.35 (m, 1H), 3.45-3.69 (m, 2H), 3.72-3.85 (m, 1H), 4.22-4.46 (m, 2H), 5.25 (s, 2H), 6.98-7.07 (m, 2H), 7.20-7.29 (m, 1H), 7.34-7.45 (m, 2H), 7.87 (d, J=8.6 Hz, 1H), 10.49-10.69 (br. band, 1H), 11.47-13.29 (br. band, 1H). Rt 1.37, [M+H] 457.

4-{2-[4-(2,3-Difluoro-benzyloxy)-2-methyl-phenyl]-6,7-dihydro-4H-oxazolo[4,5-c]-pyridin-5-yl}-2-methyl-butyric acid (394)

Compound 22 (Rb=2Me, 1 g, 3.8 mmol) was dissolved in acetonitril (10 ml) and to the solution was added DIPEA (1.93 ml, 11.25 mmol), sodium iodide (0.56 g, 3.75 mmol) and 4-chloro-2-methylbutyric acid methyl ester (0.85 g, 5.6 mmol). The mixture was stirred at 60° C. for 16 hrs, after which time again added DIPEA (1.93 ml, 11.25 mmol), sodium iodide (0.56 g, 3.75 mmol) and 4-chloro-2-methylbutyric acid methyl ester (0.85 g, 5.6 mmol) were added and stirring was continued for 30 hrs at 60° C. The mixture was concentrated in vacuo and purified by silica gel column chromatography (DCM/MeOH, 95/5 to 9/1, v/v) to give 525 (Rb=2Me; Rd=Me) as an oil. Compound 525 (Rb=2Me; Rd=Me) was benzylated at Mitsunobu conditions in a similar fashion as described above for the synthesis of 23. The resulting compounds 526 (0.5 mmol) were dissolved in ethanol (20 ml) and 2N NaOH solution was added (4 ml) and the mixture was stirred for 2 hrs at 50° C. The solution was neutralized with 1M HCl, extracted with DCM (3×20 ml) and the organic layers were dried on MgSO$_4$. Evaporation of the solvent resulted in the isolation of pure compound 394. $^1$H NMR (400 MHz, DMSO-d$_6$): □ ppm 1.09 (d, J=7.1 Hz, 3H), 1.51-1.61 (m, 1H), 1.80-1.92 (m, 1H), 2.36-2.46 (m, 1H), 2.56 (t, J=7.1 Hz, 2H), 2.60 (s, 3H), 2.72-2.78 (m, 2H), 2.79-2.85 (m, 2H), 3.39-3.47 (m, 2H), 5.24 (s, 2H), 6.95-7.04 (m, 2H), 7.20-7.29 (m, 1H), 7.35-7.47 (m, 2H), 7.82 (d, J=8.6 Hz, 1H), 10.85-13.06 (br. band, 1H). LC-MS: Rt 1.38, [M+H] 457.

4-{2-[4-(2,3-Difluoro-benzyloxy)-2-methyl-phenyl]-6,7-dihydro-4H-oxazolo-[4,5c]-pyridin-5-yl}-3-methyl-butyric acid (437)

Synthesis of 4-Chloro-3-methyl-butyric acid methyl ester

4-Methyl-dihydro-furan-2-one (4 g, 39.95 mmol) was dissolved in MeOH (10 ml) and the solution was cooled to −10° C. Thionyl chloride (3.6 ml, 49.9 mmol) was added dropwise. The mixture was stirred at −10° C. for 2 hrs and hereafter for 16 hrs at room temperature. The mixture was concentrated in vacuo to give crude 4-Chloro-3-methyl-butyric acid methyl ester (4 g, 87%) which was used in the next step without further purification.

Compound 22 (Rb=2Me, Rd=Me) was selectively alkylated at the nitrogen position with 4-chloro-3-methyl-butyric acid methyl ester to give 528. Subsequent benzylation of 528 under previously described Mitsunobu conditions gave 529. Compound 529 was demethylated in a similar fashion as described above for the synthesis of compound 394 to give compound 437 (Ra=2,3-diF, Rb=2Me, Rd=H) as a white solid. $^1$H NMR (400 MHz, DMSO-d$_6$): □ ppm 1.12 (d, J=6.6 Hz, 3H), 2.26 (dd, J=16.3, 7.3 Hz, 1H), 2.44-2.57 (m, 2H), 2.63 (s, 3H), 2.99-3.96 (m, 6H), 4.10-4.65 (br. b., 2H), 5.24 (s, 2H), 6.96-7.08 (m, 2H), 7.18-7.27 (m, 1H), 7.31-7.43 (m, 2H), 7.88 (d, J=8.6 Hz, 1H), 10.17-11.21 (br. band, 1H), 11.46-13.30 (br. band, 1H). LC-MS: Rt 1.44, [M+H] 457.

3-{2-[4-(2-phenyl-cyclopropyl)-3-fluoro-phenyl]-6,7-dihydro-4H-oxazolo-[4,5-c]-pyridin-5-yl}-cyclobutane carboxylic acid (459 trans)

2-Phenyl-cyclopropyl-trifluoroborane 4,4,5,5-Tetramethyl-2-(2-phenyl-cyclopropyl)-[1,3,2]dioxaborolane (3.1 g, 12.7 mmol) in MeOH (48 ml) and water (12 ml) was cooled to 0° C. Potassium bifluoride (6.96 g, 88.9 mmol, 7 eq) was added and the mixture was stirred for 16 hrs at room temperature. The mixture was concentrated in vacuo and the residue was co-evaporated with acetonitril (3×40 ml). The residue was washed with warm acetonitril (3×40 ml) and the combined actonitril washings were concentrated to give 2-phenyl-cyclopropyl-trifluoroborane (2 g, 71%). This trifluoroborane derivative (1.8 g, 8.2 mmol, 1.3 mmol) was dissolved in degassed toluene/water (137.5 ml, 10/1, v/v) and potassium phosphate tribasic (5.2 g, 24.7 mmol, 3.9 eq) was added. The mixture was stirred for 15 minutes and to this solution was added compound 28 (Rb=3F, 2.5 g, 6.3 mmol), palladium(II) acetate (71.2 mg, 0.3 mmol, 0.05 eq) and 2-dicyclohexylphosphino-2,6-di-isopropoxy-1,1-biphenyl (296 mg, 0.6 mmol, 0.1 eq, RuPhos). The mixture was stirred at 115° C. for 3 hrs after which time TLC analysis (Et$_2$O/PA, 3/7, v/v) revealed the reaction to be complete. The mixture was allowed to reach room temperature and was diluted with EtOAc (300 ml) and the solution was washed with water. The organic layer was dried on MgSO$_4$ and concentrated in vacuo to give an oil which was purified by silica gel column chromatography (Et$_2$O/PA, 3/7, v/v) to give pure 530 (2.54 g, 92%) as a white solid. The BOC in 530 was removed under acidic conditions to give 531, which was transformed to 532 under conditions for introducing the Rc-tail as described above. Compound 532 (pure trans, 0.45 g, 0.94 mmol) was dissolved in 20 ml 4M HCl in dioxan. The solution was stirred for 16 hrs at room temperature. The mixture was concentrated in vacuo and stirred in diethyl ether. The resulting solid was filtered to give compound 459 (trans, 0.36 g, 83%). $^1$H NMR (400 MHz, DMSO-d$_6$): □ ppm 1.27 (d, J=7.3 Hz, 3H), 1.51-1.70 (m, 2H), 2.26-2.40 (m, 2H), 3.05-3.23 (m, 3H), 3.27 (dd, J=13.1, 4.8 Hz, 2H), 3.55-3.84 (m, 3H), 4.37 (br. s., 2H), 7.14-7.23 (m, 3H), 7.26-7.35 (m, 3H), 7.64 (d, J=11.1, Hz, 1H), 7.74 (d, J=8.3 Hz, 1H), 10.00-11.79 (br. band, 1H), 11.93-13.53 (br. band, 1H). LC-MS: Rt 1.36, [M+H] 433.

4-(2-{4-[2-(3,5-Difluoro-phenyl)-vinyl]-phenyl}-6,7-dihydro-4H-oxazolo-[4,5c]-pyridin-5-yl)-butyric acid (451)

A solution of compound 28 (Rb=H, 4.3 g, 11.1 mmol), trans-2-(3,5-difluorophenyl)vinyl boronic acid pinacol ester (4.09 ml, 16.7 mmol, 1.5 eq) in toluene (100 ml) was degassed. To this solution was added chloro(2-dicyclohexylphosphino-2,4,6-tri-isopropopyl-1,1-biphenyl)[2-(2-aminoethyl)pentyl]palladium(II) methyl-tbutyl ether adduct (183.8 mg, 0.22 mmol, 0.02 eq) and potassium phosphate tribasic (7.08 g, 33.3 mmol, 3.0 eq) was added. The mixture was stirred for 24 hrs at 115° C. after which time LC-MS analysis revealed the reaction to be complete. The mixture was allowed to reach room temperature and was diluted with EtOAc (300 ml) and the solution was washed with a 5% NaHCO3 solution. The organic layer was dried on $MgSO_4$ and concentrated in vacuo to give an oil which was purified by silica gel column chromatography (DCM/MeOH, 99.5/0.5, v/v) to give pure 533 (3.4 g, 69%) as a white solid. The BOC in 533 was removed under acidic conditions to give 534, which was transformed to 535 under conditions for introducing the Rc-tail as described above. Compound 535 (0.45 g, 0.94 mmol) was dissolved in 20 ml 4M HCl in dioxan. The solution was stirred for 16 hrs at 55° C. The mixture was concentrated in vacuo and stirred in diethyl ether. The resulting solid was filtered to give compound 451 (0.426 g, 95%).

$^1$H NMR (400 MHz, DMSO-$d_6$) ☐ ppm 2.02-2.14 (m, 2H) 2.40 (t, J=7.1 Hz, 2H) 3.07-3.18 (m, 1H) 3.23-3.38 (m, 3H) 3.65-3.72 (m, 1H) 3.78-3.89 (m, 1H) 4.23-4.35 (m, 1H) 4.41-4.54 (m, 1H) 6.96-7.05 (m, 1H) 7.28-7.37 (m, 3H) 7.41 (d, J=16.4 Hz, 1H) 7.74 (d, J=8.3 Hz, 2H) 7.98 (d, J=8.3 Hz, 2H) 11.25 (br. s., 1H). LC-MS: Rt 1.39, [M+H] 425.

4-(2-{4-[2-(3,5-Difluoro-phenyl)-ethyl]-phenyl}-6,7-dihydro-4H-oxazolo[4,5c]pyridin-5-yl)-butyric acid (452)

Compound 533 (1.5 g, 3.4 mmol) was dissolved in MeOH (250 ml). To the suspension was added palladium hydroxide on carbon (20%, 0.2 g, 1.42 mmol, 0.42 eq). The mixture was placed under a blanket of hydrogen at room temperature and 1 atmosphere. After 24 hrs, LC-MS analysis revealed the reaction to be complete (TLC analysis: DCM/MeOH, 99/1, v/v). The mixture was filtered over Hyflo and the filtrate was concentrated in vacuo to give 536 (1.43 g, 95%) as an oil. Compound 536 was converted to the corresponding tail derivative 538 as described above. The tBu or methyl esters were deprotected in a similar fashion as described above. Compound 452: $^1$H NMR (400 MHz, DMSO-$d_6$) ☐ ppm 1.99-2.13 (m, 2H) 2.39 (t, J=7.2 Hz, 2H) 2.96 (s, 4H) 3.18 (broad band, 2H) 3.25-3.33 (m, 2H) 3.51-3.95 (broad band, 2H) 4.34 (br. s., 2H) 6.85-6.98 (m, 3H) 7.37 (d, J=8.3 Hz, 2H) 7.88 (d, J=8.3 Hz, 2H) 10.67-11.61 (broad band, 1H) 11.86-12.71 (broad band, 1H). LC-MS: Rt 1.36, [M+H] 427.

Preparation of the Pure Enantiomers of Chiral Compounds 1 and 2.

Compounds having for example a methyl substitution in the Rc-tail give mixtures of enantiomers as the testcompound. Separation of this mixture in the pure enantiomers can be performed by chiral HPLC techniques from the moment that the chiral tail is introduced in the core, i.e. of for example compounds 1, 2, 7, 8, 9, 21, 22, 23. For those skilled in the art, it is obvious that small changes in the core can lead to a different behavior in the chiral separation process.

Therefore, each compound has been screened using a broad set of conditions such as chiral column material and eluents. In that way, for each compound was determined in which stage and under which chiral separation conditions the separation would be most succesfull. The separated endproducts were named as Rel1 and Rel2 as the absolute configuration was not yet determined. This process is illustrated by the following typical examples.

3-[2-(4-Hydroxy-phenyl)-4,5,6,7-tetrahydro-oxazolo[4,5-c]pyridine]-2-methyl-propionic acid t-butyl ester (+) and (−) enantiomers of 22b (Rb=H)

Compound 22b was made as an enantiomeric mixture as described in Scheme 5. Enantiomeric mixture was separated by chiral HPLC using the following chiral HPLC system. Stationary phase: Chiralcel OD-H (5 micron); mobile phase: n-heptane/2-propanol (90/10, v/v) +0.1% TFA; flowrate 1 ml/min; detection by UV at 280 nm. Compound 22b-rel1: $[\alpha]^{25}$=+37.1; $^1$H NMR (400 MHz, Chloroform-d) ☐ ppm 1.14 (d, J=6.8 Hz, 3H) 1.43 (s, 9H) 2.54 (dd, J=12.1, 6.2 Hz, 1H) 2.60-2.70 (m, 1H) 2.73-2.77 (m, 2H) 2.80-2.97 (m, 3H) 3.49 (d, J=14.1 Hz, 1H) 3.60 (d, J=14.1 Hz, 1H) 6.71-6.96 (br. band, 1H) 6.84 (d, J=8.6 Hz, 2H) 7.82 (d, J=8.6 Hz, 2H). Compound 22-rel2: $[\alpha]^{25}$=−35.9; $^1$H NMR (400 MHz, Chloroform-d) ☐ ppm 1.14 (d, J=6.8 Hz, 3H) 1.42 (s, 9H) 2.53 (dd, J=12.4, 6.2 Hz, 1H) 2.60-2.70 (m, 1H) 2.72-2.79 (m, 2H) 2.80-2.96 (m, 3H) 3.49 (d, J=14.1 Hz, 1H) 3.59 (d, J=14.1 Hz, 1H) 6.83 (d, J=8.6 Hz, 2H) 7.45-7.75 (br. band, 1H) 7.79 (d, J=8.6 Hz, 2H).

3-[2-(4-hydroxy-3-F-phenyl)-4,5,6,7-tetrahydro-oxazolo[4,5-c]pyridine]-2-methyl-propionic acid t-butyl ester (+) and (−) enantiomers of 22b (Rb=3F)

Compound 22b (Rb=H) was made as an enantiomeric mixture as described in Scheme 5. Enantiomeric mixture was separated by chiral HPLC using the following chiral HPLC system. Stationary phase: Chiralcel OD-H (5 micron); mobile phase: n-heptane/2-propanol (90/10, v/v)+0.1% TFA; flowrate 1 ml/min; detection by UV at 280 nm. Compound 22b-rel1: $[\alpha]^{25}$=−36.4 (MeOH). Compound 22-rel2: $[\alpha]^{25}$=+34.8; $^1$H NMR (400 MHz, Chloroform-d) ☐ ppm 1.15 (d, J=6.8 Hz, 3H) 1.43 (s, 9H) 2.54 (dd, J=11.9, 6.2 Hz, 1H) 2.60-2.71 (m, 1H) 2.73-2.79 (m, 2H) 2.81-2.96 (m, 3H) 3.49 (d, J=14.1 Hz, 1H) 3.59 (d, J=14.1 Hz, 1H) 4.88-6.89 (br. band, 1H) 7.02 (t, J=8.5 Hz, 1H) 7.61-7.73 (m, 2H).

3-{2-[4-(4-2,3-diF-benzyloxy)-phenyl]-6,7-dihydro-H-oxazolo[4,5-c]pyridine-5-yl}-butyric acid rel 1 and rel 2 of compound 175

The tbutylprotected derivative of 175 was separated in its pure enantiomers by chiral HPLC. Stationary phase: Chiralpak IC (5μ); column code no.: WJH022830; dimensions: 250×4.6 mm; Mobile phase: n-Heptane/DCM/ethanol (50/50/1)+0.1% DEA; flowrate: 1 ml/min; Injection: 5 μl; Detection: UV (290 nm). Deprotection of thus obtained pure enantiomers resulted in the isolation of the testcompounds 426 and 425. Compound 426, rel1: $[\alpha]^{25}$=−22 (MeOH), Rt 1.3, [M+H] 429. Compound 425 rel2: $[\alpha]^{25}$=+19.9 (MeOH); Rt 1.3, [M+H] 429.

TABLE 1

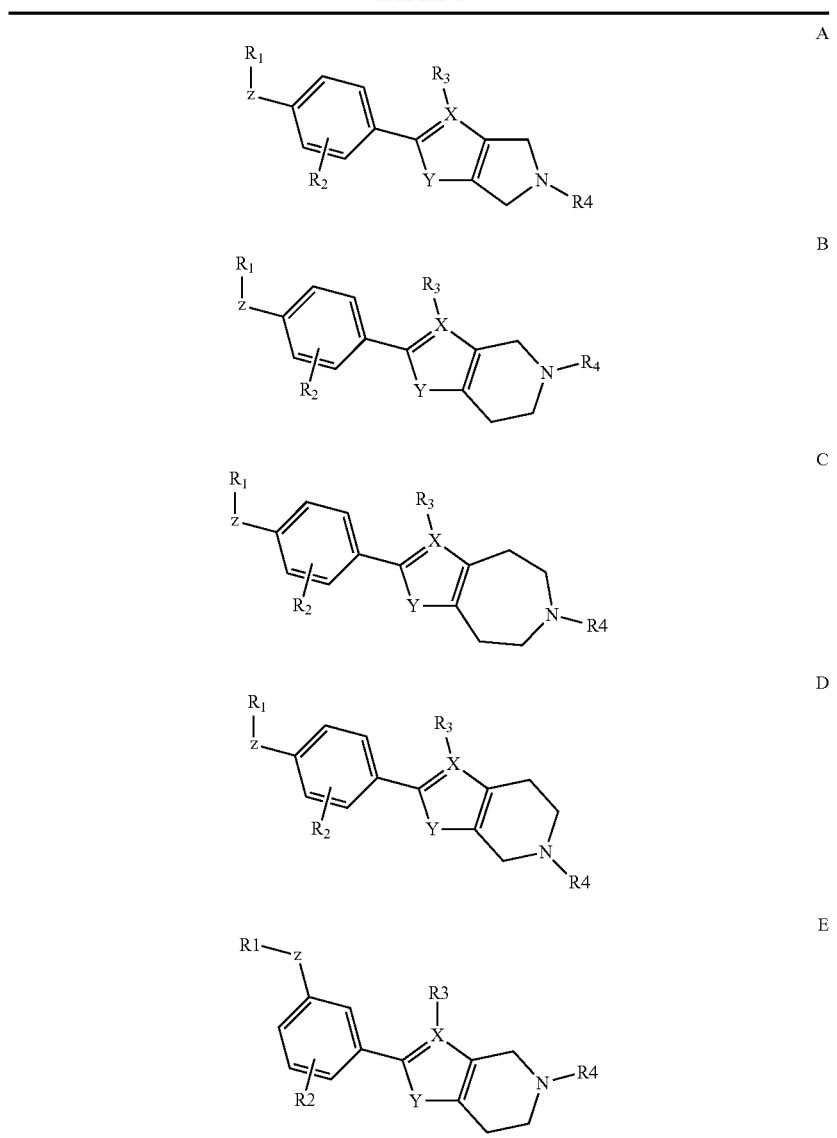

| No. | R1 | Z | R2 | X | Y | R3 | Structure | R4 | Rt (min) LC-MS |
|---|---|---|---|---|---|---|---|---|---|
| 31 | 4-Cl-phenyl | CH₂N | H | C | O | H | B | —(CH₂)₂—COOH | 1,37 |
| 32 | cyclohexyl | CH₂O | H | C | O | H | B | —(CH₂)₃—COOH | 1,46 |
| 33 | 2F-phenyl | CH₂O | H | C | O | H | B | —(CH₂)₂—COOH | 1,39 |
| 34 | 2,6diCl-phenyl | CH₂O | H | C | O | H | B | —(CH₂)₃—COOH | 1,4 |
| 35 | 2F-phenyl | CH₂O | H | C | O | H | B | —(CH₂)₃—COOH | 1.37 |
| 36 | 2F-3pyridyl | CH₂O | H | C | O | H | B | —(CH₂)₂—COOH | 1,21 |
| 37 | phenyl | CH₂ | H | C | O | H | B | —(CH₂)₂—COOH | 1,38 |
| 38 | 2F-phenyl | CH₂O | H | N | S | H | D | —(CH₂)₂—COOH | 1,3 |
| 39 | phenyl | N | H | C | O | H | B | —(CH₂)₂—COOH | 1,31 |
| 40 | 2,6diCl-phenyl | CH₂O | H | N | S | H | D | —(CH₂)₃—COOH | 1,35 |
| 41 | phenyl | C≡C | H | C | O | H | B | —(CH₂)₂—COOH | 1,42 |
| 42 | phenyl | (CH₂)₂ | H | C | O | H | B | —(CH₂)₂—COOH | 1,45 |
| 43 | phenyl | SO₂ | H | C | O | H | B | —(CH₂)₂—COOH | # |
| 44 | phenyl | S | H | C | O | H | B | —(CH₂)₂—COOH | 1,43 |
| 45 | benzyl | S | H | C | O | H | B | —(CH₂)₂—COOH | 1,41 |

TABLE 1-continued

| | | | | | | | | | |
|---|---|---|---|---|---|---|---|---|---|
| 46 | phenyl | O | H | C | O | H | B | —(CH$_2$)$_2$—COOH | 1,37 |
| 47 | phenyl | CH$_2$O | H | N | O | | B | —(CH$_2$)$_2$—COOH | 1,32 |
| 48 | 2F-phenyl | CH$_2$O | 2Cl | C | O | H | B | —(CH$_2$)$_2$—COOH | 1,43 |
| 49 | phenyl | CH$_2$SO$_2$ | H | C | O | H | B | —(CH$_2$)$_2$—COOH | 1,16 |
| 50 | phenyl | CH$_2$O | 3-pyr | C | O | H | B | —(CH$_2$)$_2$—COOH | 1,27 |
| 51 | 2F-phenyl | CH$_2$O | 3F | C | O | H | B | —(CH$_2$)$_2$—COOH | 1,34 |
| 52 | phenyl | C=O | H | C | O | H | B | —(CH$_2$)$_2$—COOH | 1,23 |
| 53 | phenyl | CH$_2$O | H | N | O | | B | —(CH$_2$)$_3$—COOH | 1,17 |
| 54 | 2F-phenyl | CH$_2$O | H | N | O | | B | —(CH$_2$)$_2$—COOH | 1,18 |
| 55 | 2,3-diF-phenyl | CH$_2$O | H | N | O | | B | —(CH$_2$)$_2$—COOH | 1,19 |
| 56 | 2F-phenyl | CH$_2$O | H | N | O | | B | —(CH$_2$)$_3$—COOH | 1,15 |
| 57 | 2,3-diF-phenyl | CH$_2$O | H | N | O | | B | —(CH$_2$)$_3$—COOH | 1,16 |
| 58 | 4Cl-phenyl | CH$_2$O | H | N | O | | B | —(CH$_2$)$_2$—COOH | 1,37 |
| 59 | 2F-phenyl | CH(Me—O) | H | C | O | H | B | —(CH$_2$)$_3$—COOH | # |
| 60 | 2,6-diCl-phenyl | CH$_2$O | H | N | O | | B | —(CH$_2$)$_3$—COOH | 1,32 |
| 61 | 4Cl-phenyl | CH$_2$O | H | N | O | | B | —(CH$_2$)$_3$—COOH | 1,29 |
| 62 | 2,6-diCl-phenyl | CH$_2$O | H | N | O | | B | —(CH$_2$)$_2$—COOH | 1,36 |
| 63 | 2F-phenyl | NH | H | C | O | H | E | —(CH$_2$)$_2$—COOH | 1,33 |
| 64 | 2F-phenyl | CH$_2$O | H | C | N | H | A | —(CH$_2$)$_2$—COOH | 1,32 |
| 65 | 2F-phenyl | bond | H | C | O | H | E | —(CH$_2$)$_2$—COOH | 1,33 |
| 66 | 2F-phenyl | O | H | C | O | H | E | —(CH$_2$)$_2$—COOH | 1,34 |
| 67 | 2F-phenyl | CH$_2$O | H | C | O | H | E | —(CH$_2$)$_2$—COOH | 1,36 |
| 68 | 2F-phenyl | CH$_2$N | H | C | O | H | E | —(CH$_2$)$_2$—COOH | 1,29 |
| 69 | 2F-phenyl | CH$_2$O | H | C | O | CH$_3$ | B | —(CH$_2$)$_2$—COOH | 1,38 |
| 70 | 2F-phenyl | CH$_2$O | H | C | O | H | C | —(CH$_2$)$_3$—COOH | 1,35 |
| 71 | 2F-phenyl | CH$_2$O | H | C | O | H | A | —(CH$_2$)$_2$—COOH | 1,32 |
| 72 | 2F-phenyl | CH$_2$O | H | C | O | H | D | —(CH$_2$)$_2$—COOH | 1,36 |
| 73 | 2F-phenyl | CH$_2$O | 2F | C | O | H | B | —(CH$_2$)$_3$—COOH | 1,35 |
| 74 | 4CF$_3$-phenyl | CH$_2$O | H | C | O | H | B | —(CH$_2$)$_2$—COOH | # |
| 75 | phenyl | CH$_2$O | H | C | O | H | B | —CH$_2$—CH(CH$_3$)— | 1,46 |
| 76 | phenyl | CH$_2$O | H | C | O | H | B | —CH(CH$_3$)—CH$_2$—COOH | 1,46 |
| 77 | 4Cl-phenyl | CH$_2$O | H | C | O | H | B | —CH$_2$—CH(CH$_3$)— | 1,56 |
| 78 | 4Cl-phenyl | CH$_2$O | H | C | O | H | B | —CH$_2$—C(CH$_3$)$_2$— | 1,76 |
| 79 | 2F-phenyl | cyclopropyl | H | C | O | H | B | —(CH$_2$)$_2$—COOH | 1,46 |
| 80 | 2F-phenyl | OCH$_2$ | H | C | O | H | B | —(CH$_2$)$_2$—COOH | 1,39 |
| 81 | phenyl | CH$_2$O | 2F | N | O | | B | —(CH$_2$)$_3$—COOH | 1,54 |
| 82 | phenyl | C≡C | H | C | O | H | E | —(CH$_2$)$_2$—COOH | 1,63 |
| 83 | 2F-phenyl | C≡C | H | C | O | H | E | —(CH$_2$)$_2$—COOH | 1,65 |
| 84 | 3F,5Cl-phenyl | CH$_2$O | H | C | O | H | B | —(CH$_2$)$_2$—COOH | 1,8 |
| 85 | 4CF$_3$-phenyl | CH$_2$O | 2F | N | O | | B | —(CH$_2$)$_3$—COOH | 1,77 |
| 86 | 4Cl-phenyl | CH$_2$O | 2F | N | O | | B | —(CH$_2$)$_3$—COOH | 1,65 |
| 87 | 2F-phenyl | CH$_2$O | 2F | N | O | | B | —(CH$_2$)$_3$—COOH | 1,58 |
| 88 | 2,3-diF-phenyl | CH$_2$O | 2F | N | O | | B | —(CH$_2$)$_3$—COOH | 1,59 |
| 89 | 2F-phenyl | CH$_2$O | 2CH$_3$ | N | O | | B | —(CH$_2$)$_3$—COOH | 1,61 |
| 90 | phenyl | CH$_2$O | 2CH$_3$ | N | O | | B | —(CH$_2$)$_3$—COOH | 1,69 |

TABLE 1-continued

| | | | | | | | | |
|---|---|---|---|---|---|---|---|---|
| 91 | 4Cl-phenyl | CH$_2$O | 2CH$_3$ | N | O | B | —(CH$_2$)$_3$—COOH | 1,75 |
| 92 | 2,3-diF-phenyl | O | 2CH$_3$ | N | O | B | —(CH$_2$)$_3$—COOH | 1,77 |
| 93 | 3,4-diF-phenyl | O | 2CH$_3$ | N | O | B | —(CH$_2$)$_3$—COOH | 1,8 |
| 94 | 4CF$_3$-phenyl | O | 2CH$_3$ | N | O | B | —(CH$_2$)$_3$—COOH | 1,98 |
| 95 | 2CH$_3$-phenyl | O | H | N | O | B | —(CH$_2$)$_2$—COOH | 2,09* |
| 96 | 4CF$_3$-phenyl | CH$_2$O | H | N | O | B | —(CH$_2$)$_2$—COOH | 1,97* |
| 97 | 4CH$_3$O-phenyl | CH$_2$O | H | N | O | B | —(CH$_2$)$_2$—COOH | 1,93* |
| 98 | 4CF$_3$-phenyl | CH$_2$O | H | N | O | B | —(CH$_2$)$_2$—COOH | 2.1* |
| 99 | 4CF$_3$O-phenyl | CH$_2$O | H | N | O | B | —(CH$_2$)$_2$—COOH | 2,08* |
| 100 | 4F-phenyl | CH$_2$O | H | N | O | B | —(CH$_2$)$_2$—COOH | 1,98* |
| 101 | 3CH$_3$O-phenyl | CH$_2$O | H | N | O | B | —(CH$_2$)$_2$—COOH | 1,86* |
| 102 | 3F-phenyl | CH$_2$O | H | N | O | B | —(CH$_2$)$_2$—COOH | 1,87* |
| 103 | 3CF$_3$O-phenyl | CH$_2$O | H | N | O | B | —(CH$_2$)$_2$—COOH | 2* |
| 104 | 3CF$_3$-phenyl | CH$_2$O | H | N | O | B | —(CH$_2$)$_2$—COOH | 2,04* |
| 105 | 2,6diF-phenyl | CH$_2$O | H | N | O | B | —(CH$_2$)$_2$—COOH | 1,82* |
| 106 | 2,5diF-phenyl | CH$_2$O | H | N | O | B | —(CH$_2$)$_2$—COOH | 1,83* |
| 107 | 2F,6Cl-phenyl | CH$_2$O | H | N | O | B | —(CH$_2$)$_2$—COOH | 1,84* |
| 108 | 2,3,6-triF-phenyl | CH$_2$O | H | N | O | B | —(CH$_2$)$_2$—COOH | 1,82* |
| 109 | 3,4diF-phenyl | CH$_2$O | H | N | O | B | —(CH$_2$)$_2$—COOH | 1,84* |
| 110 | 2,4diF-phenyl | CH$_2$O | H | N | O | B | —(CH$_2$)$_2$—COOH | 1,84* |
| 111 | 3CH$_3$-phenyl | CH$_2$O | H | N | O | B | —(CH$_2$)$_2$—COOH | 1,86* |
| 112 | 3,5diF-phenyl | CH$_2$O | H | N | O | B | —(CH$_2$)$_2$—COOH | 1,85* |
| 113 | 2CF3-phenyl | CH$_2$O | H | N | O | B | —(CH$_2$)$_2$—COOH | 1,88* |
| 114 | 3,4diF-phenyl | CH$_2$O | 2F | N | O | B | —(CH$_2$)$_2$—COOH | 1,68 |
| 115 | 2F-phenyl | CH$_2$O | 2CH$_3$ | N | O | B | —(CH$_2$)$_2$—COOH | 1,53 |
| 116 | phenyl | CH$_2$O | 2CH$_3$ | N | O | B | —(CH$_2$)$_2$—COOH | 1,53 |
| 117 | 4Cl-phenyl | CH$_2$O | 2CH$_3$ | N | O | B | —(CH$_2$)$_2$—COOH | 1,59 |
| 118 | 2,3diF-phenyl | CH$_2$O | 2CH$_3$ | N | O | B | —(CH$_2$)$_2$—COOH | 1,52 |
| 119 | 3,4diF-phenyl | CH$_2$O | 2CH$_3$ | N | O | B | —(CH$_2$)$_2$—COOH | 1,74 |
| 120 | 4CF3-phenyl | CH$_2$O | 2CH$_3$ | N | O | B | —(CH$_2$)$_2$—COOH | 1,8 |
| 121 | 4CH$_3$-phenyl | CH$_2$O | 2F | N | O | B | —(CH$_2$)$_2$—COOH | 1,86* |
| 122 | 4CF$_3$-phenyl | CH$_2$O | 2F | N | O | B | —(CH$_2$)$_2$—COOH | 1,89* |
| 123 | 4CF$_3$O-phenyl | CH$_2$O | 2F | N | O | B | —(CH$_2$)$_2$—COOH | 1,93* |
| 124 | 4F-phenyl | CH$_2$O | 2F | N | O | B | —(CH$_2$)$_2$—COOH | 1,83* |
| 125 | 3CH$_3$O-phenyl | CH$_2$O | 2F | N | O | B | —(CH$_2$)$_2$—COOH | 1,82* |
| 126 | 3F-phenyl | CH$_2$O | 2F | N | O | B | —(CH$_2$)$_2$—COOH | 1,82* |
| 127 | 4Cl-phenyl | CH$_2$O | 2F | N | O | B | —(CH$_2$)$_2$—COOH | 1,88* |
| 128 | 3CF$_3$O-phenyl | CH$_2$O | 2F | N | O | B | —(CH$_2$)$_2$—COOH | 1,91* |
| 129 | 2F-phenyl | CH$_2$O | 2F | N | O | B | —(CH$_2$)$_2$—COOH | 1,82* |
| 130 | 3CF$_3$-phenyl | CH$_2$O | 2F | N | O | B | —(CH$_2$)$_2$—COOH | 1,9* |

TABLE 1-continued

| | | | | | | | | |
|---|---|---|---|---|---|---|---|---|
| 131 | 2CH₃-phenyl | CH₂O | 2F | N | O | B | —(CH₂)₂—COOH | 1,85* |
| 132 | 2,6diF-phenyl | CH₂O | 2F | N | O | B | —(CH₂)₂—COOH | 1,8* |
| 133 | 2,5diF-phenyl | CH₂O | 2F | N | O | B | —(CH₂)₂—COOH | 1,84* |
| 134 | 2F,6Cl-phenyl | CH₂O | 2F | N | O | B | —(CH₂)₂—COOH | 1,89* |
| 135 | 2,3,6triF-phenyl | CH₂O | 2F | N | O | B | —(CH₂)₂—COOH | 1,84* |
| 136 | 2,6diCl-phenyl | CH₂O | 2F | N | O | B | —(CH₂)₂—COOH | 1,87* |
| 137 | 2,3diF-phenyl | CH₂O | 2F | N | O | B | —(CH₂)₂—COOH | 1,84* |
| 138 | 3,4diF-phenyl | CH₂O | 2F | N | O | B | —(CH₂)₂—COOH | 1,86* |
| 139 | 2,4diF-phenyl | CH₂O | 2F | N | O | B | —(CH₂)₂—COOH | 1,86* |
| 140 | 2,5diCl-phenyl | CH₂O | 2F | N | O | B | —(CH₂)₂—COOH | 1,91* |
| 141 | 3CH₃-phenyl | CH₂O | 2F | N | O | B | —(CH₂)₂—COOH | 1,86* |
| 142 | 3,5diF-phenyl | CH₂O | 2F | N | O | B | —(CH₂)₂—COOH | 1,84* |
| 143 | 2Cl-phenyl | CH₂O | 2F | N | O | B | —(CH₂)₂—COOH | 1,9* |
| 144 | 2CF₃-phenyl | CH₂O | 2F | N | O | B | —(CH₂)₂—COOH | 1,89* |
| 145 | 3,4diCl-phenyl | CH₂O | 2F | N | O | B | —(CH₂)₂—COOH | 1,95* |
| 146 | phenyl | CH₂O | H | N | O | B | —CH₂—CH(CH₃)— | 1,48 |
| 147 | phenyl | CH₂O | H | N | O | D | —(CH₂)₂—COOH | 1,28 |
| 148 | 3,4diF-phenyl | CH₂O | 3Me | C | O | B | —(CH₂)₃—COOH | 1,68 |
| 149 | 4CF₃-phenyl | CH₂O | H | N | O | B | —(CH₂)₃—COOH | 1,63 |
| 150 | 2CH₃-phenyl | CH₂O | H | N | O | B | —(CH₂)₃—COOH | 1,48 |
| 151 | 3,4diF-phenyl | CH₂O | H | N | O | B | —(CH₂)₃—COOH | 1,56 |
| 152 | 4F-phenyl | CH₂O | H | N | O | B | —(CH₂)₃—COOH | 1,55 |
| 153 | 3,5diF-phenyl | CH₂O | H | N | O | B | —(CH₂)₃—COOH | 1,48 |
| 154 | 2,3diF-phenyl | CH₂O | H | N | O | B | —CH₂—CH(CH₃)— | 1,32 |
| 155 | 3,4diF-phenyl | CH₂O | H | N | O | B | —CH₂—CH(CH₃)— | 1,63 |
| 156 | 4CF₃-phenyl | CH₂O | H | N | O | B | —CH₂—CH(CH₃)— | 1,82 |
| 157 | 4Cl-phenyl | CH₂O | H | N | O | B | —CH₂—CH(CH₃)— | 1,72 |
| 158 | 2F-phenyl | CH₂O | H | N | O | B | —CH₂—CH(CH₃)— | 1,44 |
| 159 | phenyl | CH₂O | H | N | O | B | —CH(CH₃)—CH₂—COOH | 1,87* |
| 160 | 4CF₃-phenyl | CH₂O | H | N | O | B | —CH(CH₃)—CH₂—COOH | 2,03* |
| 161 | 4CF₃O-phenyl | CH₂O | H | N | O | B | —CH(CH₃)—CH₂—COOH | 2,03* |
| 162 | 4F-phenyl | CH₂O | H | N | O | B | —CH(CH₃)—CH₂—COOH | 1,89* |
| 163 | 3CH₃O-phenyl | CH₂O | H | N | O | B | —CH(CH₃)—CH₂—COOH | 1,85* |
| 164 | 3F-phenyl | CH₂O | H | N | O | B | —CH(CH₃)—CH₂—COOH | 1,89* |
| 165 | 4Cl-phenyl | CH₂O | H | N | O | B | —CH(CH₃)—CH₂—COOH | 1,94* |
| 166 | 3CF₃O-phenyl | CH₂O | H | N | O | B | —CH(CH₃)—CH₂—COOH | 1,97* |
| 167 | 2F-phenyl | CH₂O | H | N | O | B | —CH(CH₃)—CH₂—COOH | 1,92* |
| 168 | 3CF₃-phenyl | CH₂O | H | N | O | B | —CH(CH₃)—CH₂—COOH | 2* |
| 169 | 3Cl-phenyl | CH₂O | H | N | O | B | —CH(CH₃)—CH₂—COOH | 1,95* |
| 170 | 2CH₃-phenyl | CH₂O | H | N | O | B | —CH(CH₃)—CH₂—COOH | 1,91* |
| 171 | 4CH₃-phenyl | CH₂O | H | N | O | B | —CH(CH₃)—CH₂—COOH | 1,92* |

TABLE 1-continued

| | | | | | | | | |
|---|---|---|---|---|---|---|---|---|
| 172 | 2,6-diF-phenyl | CH₂O | H | N | O | | B | —CH(CH₃)—CH₂—COOH | 1,89* |
| 173 | 2F,6Cl-phenyl | CH₂O | H | N | O | | B | —CH(CH₃)—CH₂—COOH | 1,92* |
| 174 | 2,6diCl-phenyl | CH₂O | H | N | O | | B | —CH(CH₃)—CH₂—COOH | 1,97* |
| 175 | 2,3-diF-phenyl | CH₂O | H | N | O | | B | —CH(CH₃)—CH₂—COOH | 1,3 |
| 176 | 3,4-diF-phenyl | CH₂O | H | N | O | | B | —CH(CH₃)—CH₂—COOH | 1,89* |
| 177 | 2,4-diF-phenyl | CH₂O | H | N | O | | B | —CH(CH₃)—CH₂—COOH | 1,89* |
| 178 | 2,5-diCl-phenyl | CH₂O | H | N | O | | B | —CH(CH₃)—CH₂—COOH | 1,99* |
| 179 | 3CH₃-phenyl | CH₂O | H | N | O | | B | —CH(CH₃)—CH₂—COOH | 1,93* |
| 180 | 3,5-diF-phenyl | CH₂O | H | N | O | | B | —CH(CH₃)—CH₂—COOH | 1,9* |
| 181 | 2CF₃-phenyl | CH₂O | H | N | O | | B | —CH(CH₃)—CH₂—COOH | 1,96* |
| 182 | 4-CH₃O-phenyl | CH₂O | H | N | O | | B | —CH(CH₃)—CH₂—COOH | 2,0* |
| 183 | 3,4-diCl-phenyl | CH₂O | H | N | O | | B | —CH(CH₃)—CH₂—COOH | 1,6 |
| 184 | 4pyridinyl | CH₂O | H | N | O | | B | —CH(CH₃)—CH₂—COOH | 1,51* |
| 185 | 2F,4Cl-phenyl | CH₂O | H | N | O | | B | —CH(CH₃)—CH₂—COOH | 1,95* |
| 186 | 2F,4CH₃-phenyl | CH₂O | H | N | O | | B | —CH(CH₃)—CH₂—COOH | 1,95* |
| 187 | 4CN-phenyl | CH₂O | H | N | O | | B | —CH(CH₃)—CH₂—COOH | 1,84* |
| 188 | 2,3,6-triF | CH₂O | H | N | O | | B | —CH(CH₃)—CH₂—COOH | 1,89* |
| 189 | 2,5-diF-phenyl | CH₂O | H | N | O | | B | —CH(CH₃)—CH₂—COOH | 1,89* |
| 190 | chexyl | CH₂O | H | N | O | | B | —CH(CH₃)—CH₂—COOH | 2,05* |
| 191 | 2Cl,4F-phenyl | CH₂O | H | C | O | H | B | —(CH₂)₃—COOH | 1,43 |
| 192 | 2,3-diCl-phenyl | CH₂O | H | C | O | H | B | —(CH₂)₃—COOH | 1,48 |
| 193 | phenyl | CH₂O | H | N | O | | B | —(CH₂)₃—COOH | 1,24 |
| 194 | 2F-phenyl | CH₂O | H | N | O | | B | —C[(CH₂)₂]—CH₂—COOH | 1,87 |
| 195 | 4CF₃O-phenyl | CH₂O | 2F | N | O | | B | —(CH₂)₃—COOH | 1,47 |
| 196 | 4F-phenyl | CH₂O | 2F | N | O | | B | —(CH₂)₃—COOH | 1,35 |
| 197 | phenyl | CH₂O | 3CH₃O | N | O | | B | —(CH₂)₂—COOH | 1,3 |
| 198 | 4Cl-phenyl | CH₂O | 3CH₃O | N | O | | B | —(CH₂)₂—COOH | 1,37 |
| 199 | 2,4diF-phenyl | CH₂O | 2F | N | O | | B | —(CH₂)₃—COOH | 1,36 |
| 200 | 4Me-phenyl | CH₂O | 2F | N | O | | B | —(CH₂)₃—COOH | 1,39 |
| 201 | 3,4diF-phenyl | CH₂O | 3CH₃O | N | O | | B | —(CH₂)₂—COOH | 1,35 |
| 202 | 3,5diF-phenyl | CH₂O | 3CH₃O | N | O | | B | —(CH₂)₂—COOH | 1,35 |
| 203 | 4CF3-phenyl | CH₂O | 3CH₃O | N | O | | B | —(CH₂)₂—COOH | 1,41 |
| 204 | 2F-phenyl | CH₂O | 3CH₃O | N | O | | B | —(CH₂)₂—COOH | 1,28 |
| 205 | 2,3diF-phenyl | CH₂O | 3CH₃O | N | O | | B | —(CH₂)₂—COOH | 1,32 |
| 206 | 4CF₃-phenyl | CH₂O | 3F | N | O | | B | —(CH₂)₃—COOH | 2,05* |
| 207 | 4F-phenyl | CH₂O | 3F | N | O | | B | —(CH₂)₃—COOH | 1,97* |
| 208 | 3CH₃O-phenyl | CH₂O | 3F | N | O | | B | —(CH₂)₃—COOH | 1,25* |
| 209 | 3F-phenyl | CH₂O | 3F | N | O | | B | —(CH₂)₃—COOH | 2,1* |
| 210 | 3CF₃O-phenyl | CH₂O | 3F | N | O | | B | —(CH₂)₃—COOH | 2,06* |
| 211 | 4Cl-phenyl | CH₂O | 3F | N | O | | B | —(CH₂)₃—COOH | 2,03* |
| 212 | 2F-phenyl | CH₂O | 3F | N | O | | B | —(CH₂)₃—COOH | 1,96* |

TABLE 1-continued

| | | | | | | | | |
|---|---|---|---|---|---|---|---|---|
| 213 | 3Cl-phenyl | CH$_2$O | 3F | N | O | B | —(CH$_2$)$_3$—COOH | 2* |
| 214 | 4CH$_3$-phenyl | CH$_2$O | 3F | N | O | B | —(CH$_2$)$_3$—COOH | 2,02* |
| 215 | 2,6diF-phenyl | CH$_2$O | 3F | N | O | B | —(CH$_2$)$_3$—COOH | 1,94* |
| 216 | 2,3,6-triF-phenyl | CH$_2$O | 3F | N | O | B | —(CH$_2$)$_3$—COOH | 1,98* |
| 217 | 2,6diCl-phenyl | CH$_2$O | 3F | N | O | B | —(CH$_2$)$_3$—COOH | 2,03* |
| 218 | 2,3diF-phenyl | CH$_2$O | 3F | N | O | B | —(CH$_2$)$_3$—COOH | 2,03* |
| 219 | 2,5diCl-phenyl | CH$_2$O | 3F | N | O | B | —(CH$_2$)$_3$—COOH | 2,06* |
| 220 | 3,4diF-phenyl | CH$_2$O | 3F | N | O | B | —(CH$_2$)$_3$—COOH | 2* |
| 221 | 3,4diF-phenyl | CH$_2$O | 3F | N | O | B | —(CH$_2$)$_3$—COOH | 1,98* |
| 222 | 3CH$_3$-phenyl | CH$_2$O | 3F | N | O | B | —(CH$_2$)$_3$—COOH | 2,03* |
| 223 | 2CF$_3$-phenyl | CH$_2$O | 3F | N | O | B | —(CH$_2$)$_3$—COOH | 2,03* |
| 224 | 4CH$_3$O-phenyl | CH$_2$O | 3F | N | O | B | —(CH$_2$)$_3$—COOH | 1,96* |
| 225 | 3,5diF-phenyl | CH$_2$O | 3F | N | O | B | —(CH$_2$)$_3$—COOH | 1,99* |
| 226 | 2,4diF-phenyl | CH$_2$O | 3F | N | O | B | —(CH$_2$)$_3$—COOH | 1,98* |
| 227 | 3,4diCl-phenyl | CH$_2$O | 2F | N | O | B | —(CH$_2$)$_3$—COOH | 1,42 |
| 228 | 2F,4CH$_3$-phenyl | CH$_2$O | 3F | N | O | B | —(CH$_2$)$_3$—COOH | 1,86* |
| 229 | 3,4diCl-phenyl | CH$_2$O | 3F | N | O | B | —(CH$_2$)$_3$—COOH | 2,07* |
| 230 | 3,5diF-phenyl | CH$_2$O | 2F | N | O | B | —(CH$_2$)$_3$—COOH | 1,33 |
| 231 | 2CH$_3$-phenyl | CH$_2$O | 3F | N | O | B | —(CH$_2$)$_3$—COOH | 1,99* |
| 232 | 2Cl-phenyl | CH$_2$O | 3F | N | O | B | —(CH$_2$)$_3$—COOH | 2,01* |
| 233 | 4F-phenyl | CH$_2$O | 2CH$_3$ | N | O | B | —(CH$_2$)$_2$—COOH | 1,38 |
| 234 | 2,4diF-phenyl | CH$_2$O | 2CH$_3$ | N | O | B | —(CH$_2$)$_2$—COOH | 1,38 |
| 235 | 3CF$_3$-phenyl | CH$_2$O | 2F | N | O | B | —(CH$_2$)$_3$—COOH | 1,39 |
| 236 | 4CF$_3$O-phenyl | CH$_2$O | 3CH$_3$O | N | O | B | —(CH$_2$)$_2$—COOH | 1,44 |
| 237 | 2F-phenyl | CH$_2$O | 3CH$_3$O | N | O | B | —(CH$_2$)$_3$—COOH | 1,26 |
| 238 | 3CF$_3$-phenyl | CH$_2$O | 3F | N | O | B | —(CH$_2$)$_3$—COOH | 2,06* |
| 239 | 2F, 6Cl-phenyl | CH$_2$O | 3F | N | O | B | —(CH$_2$)$_3$—COOH | 1,99* |
| 240 | 2,3diF-phenyl | CH$_2$O | 3CH$_3$O | N | O | B | —(CH$_2$)$_3$—COOH | 1,26 |
| 241 | 3CF$_3$O-phenyl | CH$_2$O | 2F | N | O | B | —(CH$_2$)$_3$—COOH | 1,42 |
| 242 | 2F-phenyl | CH$_2$O | H | N | O | B | —CH$_2$—CF$_2$—COOH | 2,16 |
| 243 | 4CH$_3$-phenyl | CH$_2$O | 2CH$_3$ | N | O | B | —(CH$_2$)$_3$—COOH | 1,37 |
| 244 | 4F-phenyl | CH$_2$O | 2CH$_3$ | N | O | B | —(CH$_2$)$_3$—COOH | 1,33 |
| 245 | 2,4diF-phenyl | CH$_2$O | 2CH$_3$ | N | O | B | —(CH$_2$)$_3$—COOH | 1,33 |
| 246 | 3,4diF-phenyl | CH$_2$O | 3CH$_3$O | N | O | B | —(CH$_2$)$_3$—COOH | 1,3 |
| 247 | 3,5diF-phenyl | CH$_2$O | 3CH$_3$O | N | O | B | —(CH$_2$)$_3$—COOH | 1,3 |
| 248 | 3,5diF-phenyl | CH$_2$O | 3CH$_3$O | N | O | B | —(CH$_2$)$_3$—COOH | 1,32 |
| 249 | 4CF$_3$-phenyl | CH$_2$O | 3CH$_3$O | N | O | B | —(CH$_2$)$_3$—COOH | 1,38 |
| 250 | 4CF$_3$O-phenyl | CH$_2$O | 3CH$_3$O | N | O | B | —(CH$_2$)$_3$—COOH | 1,38 |
| 251 | 3CF$_3$-phenyl | CH$_2$O | 2CH$_3$ | N | O | B | —(CH$_2$)$_3$—COOH | 1,4 |
| 252 | 3,4diCl-phenyl | CH$_2$O | 2CH$_3$ | N | O | B | —(CH$_2$)$_3$—COOH | 1,45 |

TABLE 1-continued

| | | | | | | | | |
|---|---|---|---|---|---|---|---|---|
| 253 | 3CF$_3$O-phenyl | CH$_2$O | 2CH$_3$ | N | O | B | —(CH$_2$)$_3$—COOH | 1,48 |
| 254 | 4Cl-phenyl | CH$_2$O | 2Cl | N | O | B | —(CH$_2$)$_3$—COOH | 1,38 |
| 255 | 3,4diF-phenyl | CH$_2$O | 2Cl | N | O | B | —(CH$_2$)$_3$—COOH | 1,36 |
| 256 | 3,5diF-phenyl | CH$_2$O | 2Cl | N | O | B | —(CH$_2$)$_3$—COOH | 1,39 |
| 257 | 4CF$_3$-phenyl | CH$_2$O | 2Cl | N | O | B | —(CH$_2$)$_3$—COOH | 1,42 |
| 258 | 2F-phenyl | CH$_2$O | 3F | N | O | B | —(CH$_2$)$_2$—COOH | 1,35 |
| 259 | 4CF3-phenyl | CH$_2$O | 3F | N | O | B | —(CH$_2$)$_2$—COOH | 3,02 |
| 260 | 3,5diF-phenyl | CH$_2$O | 3F | N | O | B | —(CH$_2$)$_2$—COOH | 2,98 |
| 261 | 2F-phenyl | CH$_2$O | 2Cl | N | O | B | —(CH$_2$)$_3$—COOH | 2,94 |
| 262 | 3,5diF-phenyl | CH$_2$O | 2CH$_3$ | N | O | B | —(CH$_2$)$_3$—COOH | 1,66 |
| 263 | 2,3diF-phenyl | CH$_2$O | 2Cl | N | O | B | —(CH$_2$)$_3$—COOH | 1,33 |
| 264 | 4CF$_3$O-phenyl | CH$_2$O | 2Cl | N | O | B | —(CH$_2$)$_3$—COOH | 1,46 |
| 265 | 3,5diCl-phenyl | CH$_2$O | 2Cl | N | O | B | —(CH$_2$)$_3$—COOH | 1,49 |
| 266 | 3,5diF-Phenyl | CH$_2$O | 2Cl | N | O | B | —(CH$_2$)$_2$—COOH | 1,42 |
| 267 | 4CF$_3$-phenyl | CH$_2$O | 2Cl | N | O | B | —(CH$_2$)$_2$—COOH | 1,5 |
| 268 | 2F-phenyl | CH$_2$O | 2Cl | N | O | B | —(CH$_2$)$_2$—COOH | 1,36 |
| 269 | 2,6diCH$_3$-phenyl | CH$_2$O | 2F | N | O | B | —(CH$_2$)$_2$—COOH | 1,36 |
| 270 | 2,3diF-phenyl | CH$_2$O | H | N | O | B | —CH$_2$—C[(CH$_2$)$_2$]— | 1,56 |
| 271 | 4CF$_3$-phenyl | CH$_2$O | 2F | N | O | B | —CH$_2$—CH(CH$_3$)— | 1,56 |
| 272 | 2,6diCH$_3$-phenyl | CH$_2$O | 2CH$_3$ | N | O | B | —(CH$_2$)$_2$—COOH | 1,46 |
| 273 | 3,4diF-phenyl | CH$_2$O | 2CH$_3$O | N | O | B | —CH(CH$_3$)—CH$_2$—COOH | 1,42 |
| 274 | 4CF$_3$-phenyl | CH$_2$O | 2CH$_3$O | N | O | B | —CH(CH$_3$)—CH$_2$—COOH | 1,51 |
| 275 | 2F-phenyl | CH$_2$O | 2CH$_3$O | N | O | B | —CH(CH$_3$)—CH$_2$—COOH | 1,37 |
| 276 | 3,5diF-phenyl | CH$_2$O | 2CH$_3$O | N | O | B | —CH(CH$_3$)—CH$_2$—COOH | 1,42 |
| 277 | 3,4diF-phenyl | CH$_2$O | H | N | O | B | -cyclobutyl-COOH | 1,31 |
| 278 | 3,4diF-phenyl | CH$_2$O | H | N | O | B | -cyclobutyl-COOH | 1,33 |
| 279 | 4Cl-phenyl | CH$_2$O | H | N | O | B | -cyclobutyl-COOH | 1,36 |
| 280 | 4Cl-phenyl | CH$_2$O | H | N | O | B | -cyclobutyl-COOH | 1,37 |
| 281 | 4F-phenyl | CH$_2$O | 3Cl | N | O | B | —(CH$_2$)$_3$—COOH | 2,03* |
| 282 | 4CF$_3$-phenyl | CH$_2$O | 3Cl | N | O | B | —(CH$_2$)$_3$—COOH | 2,11* |
| 283 | 2F-phenyl | CH$_2$O | 3Cl | N | O | B | —(CH$_2$)$_3$—COOH | 1,99* |
| 284 | 4CF$_3$O-phenyl | CH$_2$O | 3Cl | N | O | B | —(CH$_2$)$_3$—COOH | 2,1* |
| 285 | 4Cl-phenyl | CH$_2$O | 3Cl | N | O | B | —(CH$_2$)$_3$—COOH | 2,07* |
| 286 | 3CF$_3$O-phenyl | CH$_2$O | 3Cl | N | O | B | —(CH$_2$)$_3$—COOH | 2,14* |
| 287 | 3,4diF-phenyl | CH$_2$O | 3Cl | N | O | B | —(CH$_2$)$_3$—COOH | 2,03* |
| 288 | 2,4diF-phenyl | CH$_2$O | 3Cl | N | O | B | —(CH$_2$)$_3$—COOH | 2,02* |
| 289 | 3,4diCl-phenyl | CH$_2$O | 3Cl | N | O | B | —(CH$_2$)$_3$—COOH | 2,16* |
| 290 | 3,5diF-phenyl | CH$_2$O | 3Cl | N | O | B | —(CH$_2$)$_3$—COOH | 2,03* |
| 291 | 2Cl-phenyl | CH$_2$O | 3Cl | N | O | B | —(CH$_2$)$_3$—COOH | 2,05* |
| 292 | 2F,4Cl-phenyl | CH$_2$O | 3Cl | N | O | B | —(CH$_2$)$_3$—COOH | 2,06* |

TABLE 1-continued

| | | | | | | | | |
|---|---|---|---|---|---|---|---|---|
| 293 | 3CF$_3$-phenyl | CH$_2$O | 3Cl | N | O | B | —(CH$_2$)$_3$—COOH | 2,09* |
| 294 | 2,5diF-phenyl | CH$_2$O | 3Cl | N | O | B | —(CH$_2$)$_3$—COOH | 2,02* |
| 295 | 4CF$_3$-phenyl | CH$_2$O | 2F | N | O | B | —CH(CH$_3$)—CH$_2$—COOH | 1,56 |
| 296 | 4CF$_3$O-phenyl | CH$_2$O | 2CH$_3$O | N | O | B | —CH(CH$_3$)—CH$_2$—COOH | 1,54 |
| 297 | 3,4diF-phenyl | CH$_2$O | 2F | N | O | B | —CH$_2$—CH(CH$_3$)— | 1,47 |
| 298 | 3,4diF-phenyl | CH$_2$O | 3Cl | N | O | B | —(CH$_2$)$_2$—COOH | 1,44 |
| 299 | 2,3diF-phenyl | CH$_2$O | 3Cl | N | O | B | —(CH$_2$)$_3$—COOH | 2,01* |
| 300 | 2,3diF-phenyl | CH$_2$O | H | N | NH | B | —CH$_2$—CH(CH$_3$)— | 1,1 |
| 301 | 2F-phenyl | CH$_2$O | H | N | O | B | —(CH$_2$)$_2$—COOH | 1,38 |
| 302 | 2F-phenyl | CH$_2$O | H | N | O | B | -cyclobutyl-COOH | 1,29 |
| 303 | 2F-phenyl | CH$_2$O | H | N | O | B | -cyclobutyl-COOH | 1,3 |
| 304 | 4-fluoro-indan-2-yl | O | H | N | O | B | —(CH$_2$)$_2$—COOH | 1,39 |
| 305 | indan-2-yl | O | H | N | O | B | —(CH$_2$)$_2$—COOH | 1,37 |
| 306 | 4CF$_3$O-phenyl | CH$_2$O | H | N | O | B | -cyclobutyl-COOH | 1,41 |
| 307 | 4CF$_3$O-phenyl | CH$_2$O | H | N | O | B | -cyclobutyl-COOH | 1,43 |
| 308 | indan-1-yl | O | H | N | O | B | —(CH$_2$)$_2$—COOH | 1,39 |
| 309 | 4-fluoro-indan-1-yl | O | H | N | O | B | —(CH$_2$)$_2$—COOH | 1,4 |
| 310 | 4Cl-phenyl | CH$_2$O | 3Cl | N | O | B | —(CH$_2$)$_2$—COOH | 1,48 |
| 311 | 3,4diF-phenyl | CH$_2$O | 2F | N | O | B | —CH(CH$_3$)—CH$_2$—COOH | 1,45 |
| 312 | 4F-phenyl | CH$_2$O | H | N | O | B | -cyclobutyl-COOH | 1,28 |
| 313 | 4F-phenyl | CH$_2$O | H | N | O | B | -cyclobutyl-COOH | 1,3 |
| 314 | 4CF$_3$-phenyl | CH$_2$O | H | N | O | B | -cyclobutyl-COOH | 1,41 |
| 315 | 4CF$_3$-phenyl | CH$_2$O | H | N | O | B | -cyclobutyl-COOH | 1,42 |
| 316 | 3F,4Cl-phenyl | CH$_2$O | H | N | O | B | —CH(CH$_3$)—CH$_2$—COOH | 1,52 |
| 317 | 2,4,6-triF- | CH$_2$O | H | N | O | B | —CH(CH$_3$)—CH$_2$—COOH | 1,43 |
| 318 | 2Cl,4F-phenyl | CH$_2$O | H | N | O | B | —CH(CH$_3$)—CH$_2$—COOH | 1,5 |
| 319 | 2F,3Cl-phenyl | CH$_2$O | H | N | O | B | —CH(CH$_3$)—CH$_2$—COOH | 1,49 |
| 320 | 3F,5Cl-phenyl | CH$_2$O | H | N | O | B | —CH(CH$_3$)—CH$_2$—COOH | 1,54 |
| 321 | 2,6-diF,4Cl- | CH$_2$O | H | N | O | B | —CH(CH$_3$)—CH$_2$—COOH | 1,52 |
| 322 | 2,3-diCl-phenyl | CH$_2$O | H | N | O | B | —CH(CH$_3$)—CH$_2$—COOH | 1,59 |
| 323 | 2Cl-phenyl | CH$_2$O | H | N | O | B | —CH(CH$_3$)—CH$_2$—COOH | 1,48 |
| 324 | 2,4-diCl-phenyl | CH$_2$O | H | N | O | B | —CH(CH$_3$)—CH$_2$—COOH | 1,6 |
| 325 | 3,5-diCl-phenyl | CH$_2$O | H | N | O | B | —CH(CH$_3$)—CH$_2$—COOH | 1,63 |
| 326 | 3,5diF-phenyl | CH$_2$O | H | N | O | B | -cyclobutyl-COOH | 1,34 |
| 327 | 3,5diF-phenyl | CH$_2$O | H | N | O | B | -cyclobutyl-COOH(cis) | 1,34 |
| 328 | 3,4-diCl-phenyl | CH$_2$O | H | N | O | B | -cyclobutyl-COOH | 1,45 |
| 329 | 3,4-diCl-phenyl | CH$_2$O | H | N | O | B | -cyclobutyl-COOH(cis) | 1,46 |
| 330 | 4Cl-phenyl | CH$_2$O | H | N | NH | B | —CH(CH$_3$)—CH$_2$—COOH | 1,16 |
| 331 | 3,4diF-phenyl | CH$_2$O | H | N | NH | B | —CH(CH$_3$)—CH$_2$—COOH | 1,11 |
| 332 | 3,5-diCl-phenyl | CH$_2$O | H | N | NH | B | —CH(CH$_3$)—CH$_2$—COOH | 1,11 |

TABLE 1-continued

| | | | | | | | | |
|---|---|---|---|---|---|---|---|---|
| 333 | 3F-phenyl | CH₂O | H | N | O | | B | —CH₂—CH(CH₃)— | 1,57 |
| 334 | 3,5diF-phenyl | CH₂O | H | N | O | | B | —CH₂—CH(CH₃)— | 1,65 |
| 335 | 2,5diF-phenyl | CH₂O | H | N | O | | B | —CH₂—CH(CH₃)— | 1,61 |
| 336 | 2F,6Cl-phenyl | CH₂O | H | N | O | | B | —CH₂—CH(CH₃)— | 1,62 |
| 337 | 2,4diF-phenyl | CH₂O | H | N | O | | B | —CH₂—CH(CH₃)— | 1,59 |
| 338 | 4F-phenyl | CH₂O | H | N | O | | B | —CH₂—CH(CH₃)— | 1,55 |
| 339 | 2F,3Cl-phenyl | CH₂O | H | N | O | | B | —CH₂—CH(CH₃)— | 1,7 |
| 340 | 2,4,6triF-phenyl | CH₂O | H | N | O | | B | —CH₂—CH(CH₃)— | 1,6 |
| 341 | 2,6diF,4Cl- | CH₂O | H | N | O | | B | —CH₂—CH(CH₃)— | # |
| 342 | 2,3diCl-phenyl | CH₂O | H | N | O | | B | —CH₂—CH(CH₃)— | # |
| 343 | 2Cl-phenyl | CH₂O | H | N | O | | B | —CH₂—CH(CH₃)— | # |
| 344 | 2F,4Cl-phenyl | CH₂O | H | N | O | | B | —CH₂—CH(CH₃)— | # |
| 345 | 2Cl,4F-phnyl | CH₂O | H | N | O | | B | —CH₂—CH(CH₃)— | # |
| 346 | 3F,4Cl-phenyl | CH₂O | H | N | O | | B | —CH₂—CH(CH₃)— | # |
| 347 | 2,6diCl-phenyl | CH₂O | H | N | O | | B | —CH₂—CH(CH₃)— | 1,71 |
| 348 | 3Cl,5F-phenyl | CH₂O | H | N | O | | B | —CH₂—CH(CH₃)— | 1,76 |
| 349 | 4Cl-phenyl | CH₂O | H | C | S | H | B | —(CH₂)₂—COOH | #) |
| 350 | 4CF₃-phenyl | CH₂O | H | C | S | H | B | —(CH₂)₂—COOH | 1.57 |
| 351 | phenyl | CH₂O | 3 CF₃ | N | O | | B | —CH₂—CH(CH₃)— | 1.59 |
| 352 | 3,5diCl-phenyl | CH₂O | H | C | S | H | B | —(CH₂)₂—COOH | 1.6 |
| 353 | 3,5diCl-phenyl | CH₂O | H | N | O | | B | —CH₂—CH(CH₃)— | # |
| 354 | 3,5-diF-phenyl | CH₂O | H | C | S | H | B | —(CH₂)₂—COOH | 1.46 |
| 355 | 3,4diCl-phenyl | CH₂O | H | N | O | | B | —CH₂—CH(CH₃)— | #) |
| 356 | 2,4diCl-phenyl | CH₂O | H | N | O | | B | —CH₂—CH(CH₃)— | # |
| 357 | 3,4diCl-phenyl | CH₂O | 3Cl | N | O | | B | —(CH₂)₂—COOH | 1.56 |
| 358 | 3,4-diF-phenyl | CH₂O | 3Cl | N | O | | B | —CH₂—CH(CH₃)— | 1.58 |
| 359 | 4-Cl-phenyl | CH₂O | 3Cl | N | O | | B | —CH(CH₃)—CH₂—COOH | 1.73 |
| 360 | 3,4-diCl-phenyl | CH₂O | 3Cl | N | O | | B | —CH₂—CH(CH₃)— | 1.73 |
| 361 | 4-CF₃-phenyl | O | H | N | O | | B | —(CH₂)₂—COOH | 1.45 |
| 362 | 2,4,6-triF- | CH₂O | H | N | O | | B | —(CH₂)₂—COOH | 1.36 |
| 363 | 2F, 3Cl-phenyl | CH₂O | H | N | O | | B | —(CH₂)₂—COOH | 1.4 |
| 364 | 2F, 4Cl-phenyl | CH₂O | H | N | O | | B | —(CH₂)₂—COOH | 1.44 |
| 365 | 2Cl, 4F-phenyl | CH₂O | H | N | O | | B | —(CH₂)₂—COOH | 1.44 |
| 366 | 3Cl, 5F-phenyl | CH₂O | H | N | O | | B | —(CH₂)₂—COOH | 1.44 |
| 367 | 3F,4Cl-phenyl | CH₂O | H | N | O | | B | —(CH₂)₂—COOH | 1.45 |
| 368 | 2,6-diF,4Cl- | CH₂O | H | N | O | | B | —(CH₂)₂—COOH | 1.45 |
| 369 | 2,3-diCl-phenyl | CH₂O | H | N | O | | B | —(CH₂)₂—COOH | 1.5 |
| 370 | 2Cl-phenyl | CH₂O | H | N | O | | B | —(CH₂)₂—COOH | 1.4 |
| 371 | 4-Cl-phenyl | CH₂O | 3CF₃ | N | O | | B | —CH₂—CH(CH₃)— | 1.67 |
| 372 | 3,4-diCl-phenyl | CH₂O | 3CF₃ | N | O | | B | —CH₂—CH(CH₃)— | 1.78 |

TABLE 1-continued

| | | | | | | | | |
|---|---|---|---|---|---|---|---|---|
| 373 | 3,4-diF-phenyl | CH$_2$O | 3CF$_3$ | N | O | B | —CH$_2$—CH(CH$_3$)— | 1.61 |
| 374 | 3,4-diF-phenyl | CH$_2$O | 2CF$_3$ | N | O | B | —CH$_2$—CH(CH$_3$)— | 1.61 |
| 375 | 4Cl-phenyl | CH$_2$O | 2CF$_3$ | N | O | B | —CH$_2$—CH(CH$_3$)— | 1.68 |
| 376 | 3,5-diF-phenyl | CH$_2$O | 2CF$_3$ | N | O | B | —CH$_2$—CH(CH$_3$)— | 1.61 |
| 377 | 4 CF$_3$-phenyl | CH$_2$O | 2CF$_3$ | N | O | B | —CH$_2$—CH(CH$_3$)— | 1.72 |
| 378 | 4 CF$_3$-phenyl | CH$_2$O | 3CF$_3$ | N | O | B | —CH$_2$—CH(CH$_3$)— | 1.72 |
| 379 | 3,4-diCl-phenyl | CH$_2$O | H | N | O | B | —(CH$_2$)$_2$—COOH | 1.5 |
| 380 | 3,5-diCl-phenyl | CH$_2$O | H | N | O | B | —(CH$_2$)$_2$—COOH | 1.53 |
| 381 | 2,4-diCl-phenyl | CH$_2$O | H | N | O | B | —(CH$_2$)$_2$—COOH | 1.52 |
| 382 | 3,4-diF-phenyl | CH$_2$O | 2Me | N | O | B | —CH$_2$—CH(CH$_3$)— | 1.5 |
| 383 | 3,5-diF-phenyl | CH$_2$O | 2Me | N | O | B | —CH$_2$—CH(CH$_3$)— | 1.52 |
| 384 | 4CF$_3$-phenyl | CH$_2$O | 2Me | N | O | B | —CH$_2$—CH(CH$_3$)— | 1.62 |
| 385 | 2,3-diF-phenyl | CH$_2$O | 2Me | N | O | B | —CH$_2$—CH(CH$_3$)— | 1.48 |
| 386 | 3,4-diCl-phenyl | CH$_2$O | 2Me | N | O | B | —CH$_2$—CH(CH$_3$)— | 1.66 |
| 387 | 4Cl-phenyl | CH$_2$O | 2Me | N | O | B | —CH$_2$—CH(CH$_3$)— | 1.57 |
| 388 | 3,5-diF-phenyl | CH$_2$O | 3CF$_3$ | N | O | B | —CH$_2$—CH(CH$_3$)— | 1.62 |
| 389 | 2,3-diF-phenyl | CH$_2$O | 3CF$_3$ | N | O | B | —CH$_2$—CH(CH$_3$)— | 1.57 |
| 390 | 3,4-diF-phenyl | CH$_2$O | 3Cl | N | O | B | —CH$_2$—CH(CH$_3$)— | 1.56 |
| 391 | 4Cl-phenyl | CH$_2$O | 3Cl | N | O | B | —CH$_2$—CH(CH$_3$)— | 1.6 |
| 392 | 3,4-diCl-phenyl | CH$_2$O | 3Cl | N | O | B | —CH(CH$_3$)—CH$_2$—COOH | 1.67 |
| 393 | 2,3-diF-phenyl | CH$_2$O | 2Me | N | O | B | —CH(CH$_3$)—(CH$_2$)$_2$— | 1.37 |
| 394 | 2,3-diF-phenyl | CH$_2$O | 2Me | N | O | B | —(CH$_2$)$_2$—CH(CH$_3$)—COOH | 1.38 |
| 395 | 4-Cl-phenyl | CH$_2$O | 2Me | N | O | B | —(CH$_2$)$_2$—CH(CH$_3$)—COOH | 1.43 |
| 396 | 4-CF$_3$-phenyl | CH$_2$O | 2Me | N | O | B | —(CH$_2$)$_2$—CH(CH$_3$)—COOH | 1.47 |
| 397 | 3,4-diF-phenyl | CH$_2$O | 2Me | N | O | B | —(CH$_2$)$_2$—CH(CH$_3$)—COOH | 1.39 |
| 398 | 3,5-diF-phenyl | CH$_2$O | 2,6-dF | N | O | B | —(CH$_2$)$_3$—COOH | 1.34 |
| 399 | 4CF$_3$-phenyl | CH$_2$O | 2,6-dF | N | O | B | —(CH$_2$)$_3$—COOH | 1.42 |
| 400 | 2,3-diF-phenyl | CH$_2$O | H | N | O | B | —(CH$_2$)$_2$—CH(CH$_3$)—COOH | # |
| 401 | Me | O | H | N | O | B | —(CH$_2$)$_2$—COOH | #) |
| 402 | Me | O | H | N | O | B | —(CH$_2$)$_3$—COOH | # |
| 403 | 3,4-diF-phenyl | CH$_2$O | H | N | O | B | —CH(CH$_3$)—(CH$_2$)$_2$— | # |
| 404 | 4Cl-phenyl | CH$_2$O | 2Me | N | O | B | —CH(CH$_3$)—(CH$_2$)$_2$— | 1.42 |
| 405 | 4CF$_3$-phenyl | CH$_2$O | 2Me | N | O | B | —CH(CH$_3$)—(CH$_2$)$_2$— | 1.45 |
| 406 | 4Cl-phenyl | CH$_2$O | 2,3diF | N | O | B | —(CH$_2$)$_3$—COOH | 1.37 |
| 407 | 3,5-diF-phenyl | CH$_2$O | 2,3diF | N | O | B | —(CH$_2$)$_3$—COOH | 1.35 |
| 408 | 4Cl-phenyl | CH$_2$O | 2,3diF | N | O | B | —CH(CH$_3$)—CH$_2$—COOH | 1.53 |
| 409 | 3,5-diF-phenyl | CH$_2$O | 2,3diF | N | O | B | —CH(CH$_3$)—CH$_2$—COOH | 1.48 |
| 410 | 4Cl-phenyl | CH$_2$O | 2,3diF | N | O | B | trans cyclobutyl-COOH | 1.41 |
| 411 | 3,5-diF-phenyl | CH$_2$O | 2,3diF | N | O | B | cis cyclobutyl-COOH | 1.41 |
| 412 | 3,5-diF-phenyl | CH$_2$O | 2,3diF | N | O | B | trans cyclobutyl-COOH | 1.36 |
| 413 | 3,5-diF-phenyl | CH$_2$O | 2,3diF | N | O | B | cis cyclobutyl-COOH | 1.35 |

TABLE 1-continued

| | | | | | | | | |
|---|---|---|---|---|---|---|---|---|
| 414 | 3,4-diF-phenyl | CH$_2$O | 2Me | N | O | B | cis cyclobutyl-COOH | # |
| 415 | 3,4-diF-phenyl | CH$_2$O | 2Me | N | O | B | trans cyclobutyl-COOH | # |
| 416 | 2,3-diF-phenyl | CH$_2$O | 3F | N | O | B | —CH(CH$_3$)—CH$_2$—COOH | # |
| 417 | 2,3-diF-phenyl | CH$_2$O | 3F | N | O | B | —CH$_2$—CH(CH$_3$)— | # |
| 418 | 2,3-diF-phenyl | CH$_2$O | 3F | N | O | B | cis-cyclobutyl-COOH | # |
| 419 | 3,5-diF-phenyl | CH$_2$O | 3Me | N | O | B | —(CH$_2$)$_3$—COOH | 1.38 |
| 420 | 3,5-diF-phenyl | CH$_2$O | 3Me | N | O | B | —CH$_2$—CH(CH$_3$)— | 1.66 |
| 421 | 3,5-diF-phenyl | CH$_2$O | 3Me | N | O | B | —CH(CH$_3$)—CH$_2$—COOH | 1.63 |
| 422 | 4CF$_3$-phenyl | CH2S | H | N | O | B | —(CH$_2$)$_3$—COOH | 1.12 |
| 423 | 3,4-diF-phenyl | CH2S | H | N | O | B | —(CH$_2$)$_3$—COOH | 1.09 |
| 424 | 2,3-diF-phenyl | CH$_2$O | 3F | N | O | B | trans cyclobutyl-COOH | # |
| 425 | 2,3-diF-phenyl | CH$_2$O | H | N | O | B | —CH(CH$_3$)—CH$_2$—COOH chiral2 | 1.11 |
| 426 | 2,3-diF-phenyl | CH$_2$O | H | N | O | B | —CH(CH$_3$)—CH$_2$—COOH chiral1 | 1.2 |
| 427 | 3,5-diF-phenyl | CH$_2$O | 3Me | N | O | B | trans cyclobutyl-COOH | 1.37 |
| 428 | 2,3-diF-phenyl | CH$_2$O | 3Me | N | O | B | cis cyclobutyl-COOH | 1.39 |
| 429 | 2,3-diF-phenyl | CH$_2$O | 3Me | N | O | B | trans cyclobutyl-COOH | 1.35 |
| 430 | 2,3-diF-phenyl | CH$_2$O | 3Me | N | O | B | cis cyclobutyl-COOH | 1.36 |
| 431 | 3,5-diF-phenyl | CH$_2$O | 2Me | N | O | B | —CH(CH$_3$)—CH$_2$—COOH | 1.5 |
| 432 | 3,5-diF-phenyl | CH$_2$O | 2Me | N | O | B | trans cyclobutyl-COOH | 1.35 |
| 433 | 3,5-diF-phenyl | CH$_2$O | 2Me | N | O | B | cis cyclobutyl-COOH | 1.35 |
| 434 | 2,3-diF-phenyl | CH$_2$O | 2Me | N | O | B | —CH(CH$_3$)—CH$_2$—COOH | 1.47 |
| 435 | 4-Cl-phenyl | CH$_2$O | 2Me | N | O | B | —CH$_2$—CH(CH$_3$)— | 1.49 |
| 436 | 4-CF$_3$-phenyl | CH$_2$O | 2Me | N | O | B | —CH$_2$—CH(CH$_3$)— | 1.53 |
| 437 | 2,3-diF-phenyl | CH$_2$O | 2Me | N | O | B | —CH$_2$—CH(CH$_3$)— | 1.42 |
| 438 | 3,4-diF-phenyl | CH$_2$O | 2Me | N | O | B | —CH$_2$—CH(CH$_3$)— | 1.44 |
| 439 | 2,3-diF-phenyl | CH$_2$O | 3Me | N | O | B | —CHCH$_3$—CH$_2$—COOH | 1.49 |
| 440 | 2,3-diF-phenyl | CH$_2$O | 3Me | N | O | B | —CH$_2$—CH(CH$_3$)— | 1.5 |
| 441 | 4-Cl-phenyl | CH$_2$S | H | N | O | B | —(CH$_2$)$_3$—COOH | 1.38 |
| 442 | 2,3-diF-phenyl | CH$_2$S | H | N | O | B | —(CH$_2$)$_3$—COOH | 1.33 |
| 443 | 3,5-diF-phenyl | CH$_2$S | H | N | O | B | —(CH$_2$)$_3$—COOH | 1.34 |
| 444 | 3,4-diCl-phenyl | CH$_2$S | H | N | O | B | —(CH$_2$)$_3$—COOH | 1.44 |
| 445 | 4-Cl-phenyl | CH$_2$O | H | N | S | B | —(CH$_2$)$_3$—COOH | 1.36 |
| 446 | 3,5-diF-phenyl | CH$_2$O | H | N | S | B | —(CH$_2$)$_3$—COOH | 1.33 |
| 447 | 4-Cl-phenyl | CH$_2$O | H | N | S | B | —CH(CH$_3$)—CH$_2$—COOH | 1.53 |
| 448 | 3,5-diF-phenyl | CH$_2$O | H | N | S | B | —CH(CH$_3$)—CH$_2$—COOH | 1.48 |
| 449 | 4-Cl-phenyl | CH$_2$O | H | N | S | B | —CH$_2$—CH(CH$_3$)— | 1.52 |
| 450 | 3,5-diF-phenyl | CH$_2$O | H | N | S | B | —CH$_2$—CH(CH$_3$)— | 1.48 |
| 451 | 3,5-diF-phenyl | C═C | H | N | O | B | —(CH$_2$)$_3$—COOH | 1.39 |
| 452 | 3,5-diF-phenyl | (CH$_2$)$_2$ | H | N | O | B | —(CH$_2$)$_3$—COOH | 1.36 |
| 453 | 3,5-diF-phenyl | C═C | H | N | O | B | —CH$_2$—CH(CH$_3$)— | 1.59 |

TABLE 1-continued

| | | | | | | | |
|---|---|---|---|---|---|---|---|
| 454 | 3,5-diF-phenyl | (CH$_2$)$_2$ | H | N | O | B | —CH$_2$—CH(CH$_3$)— | 1.53 |
| 455 | phenyl | cyclopropyl | 3F | N | O | B | trans cyclobutyl-COOH | 1.36 |
| 456 | phenyl | cyclopropyl | 3F | N | O | B | cis-cyclobutyl-COOH | 1.39 |
| 457 | phenyl | cyclopropyl | 3F | N | O | B | —CH(CH$_3$)—CH$_2$—COOH | 1.55 |
| 458 | phenyl | cyclopropyl | 3F | N | O | B | —CH$_2$—CH(CH$_3$)— | 1.55 |
| 459 | phenyl | cyclopropyl | 3F | N | O | B | trans cyclobutyl-COOH | 1.36 |
| 460 | phenyl | cyclopropyl | 3F | N | O | B | cis-cyclobutyl-COOH | 1.39 |
| 461 | phenyl | cyclopropyl | 3F | N | O | B | —CH(CH$_3$)—CH$_2$—COOH | 1.55 |
| 462 | phenyl | cyclopropyl | 3F | N | O | B | —CH$_2$—CH(CH$_3$)— | 1.55 |
| 463 | 3,5-diF-phenyl | CH$_2$O | H | N | O | B | —CH$_2$COOH | 1.51 |
| 464 | 3,5-diF-phenyl | CH$_2$O | H | N | O | B | —CH(CH$_3$)—COOH | 1.53 |
| 465 | 3,5-diF phenyl | CH$_2$O | H | N | O | B | 1,3-cyclopentyl-COOH | 1.27 |

\* = determined with LC-MS method B
\# = NMR in accordance with proposed structure

§6. Pharmacological Tests & Data

In Vitro Functional Activity (Agonism) on Human S1P5 Receptors

The CHO-human-S1P5-Aeqorin assay was bought from Euroscreen, Brussels (Euroscreen, Technical dossier, Human Lysophospholid S1P5 (Edg8) receptor, DNA clone and CHO AequoScreen™ recombinant cell-line, catalog no: ES-593-A, September 2006). Human-S1P5-Aequorin cells express mitochondrial targeted apo-Aequorin. Cells have to be loaded with coelanterazine, in order to reconstitute active Aequorin. After binding of agonists to the human S1P5 receptor the intracellular calcium concentration increases and binding of calcium to the apo-Aequorin/coelenterazine complex leads to an oxidation reaction of coelenterazine, which results in the production of apo-Aequorin, coelenteramide, CO$_2$ and light ($\lambda_{max}$ 469 nm). This luminescent response is dependent on the agonist concentration. Luminescence is measured using the MicroBeta Jet (Perkin Elmer). Agonistic effects of compounds are expressed as pEC$_{50}$. Compounds were tested at a 10 points half log concentration range, and 3 independent experiments were performed in single point's measurements.

In Vitro Functional Activity (Agonism) on Human S1P3 Receptors

The CHO-human-S1P3-Aeqorin assay (CHO/Gα16/AEQ/h-S1P$_3$) was established at Solvay Pharmaceuticals. The plasmid DNA coding for the S1P3 receptor (accession number in GenBank NM_005226 was purchased from UMR cDNA resource Centre (Rolla, Mo.). The pcDNA3.1/hS1P3 construct carrying the mitochondrially targeted apo-Aeqorin and Gα16 protein was transfected in CHO K1 cell-line. Human-S1P3-Aequorin cells express mitochondrial targeted apo-Aequorin. Cells have to be loaded with coelanterazine, in order to reconstitute active Aequorin. After binding of agonists to the human S1P3 receptor the intracellular calcium concentration increases and binding of calcium to the apo-Aequorin/coelenterazine complex leads to an oxidation reaction of coelenterazine, which results in the production of apo-Aequorin, coelenteramide, CO$_2$ and light ($\square_{max}$ 469 nm). This luminescent response is dependent on the agonist concentration. Luminescence is measured using the MicroBeta Jet (Perkin Elmer). Agonistic effects of compounds are expressed as pEC$_{50}$. Compounds were tested at a 10 points half log concentration range, and 3 independent experiments were performed in single point's measurements.

In Vitro Functional Activity (Agonism) on Human S1P1 Receptors (Method A)

The CHO-K1-human-S1P1-Aeqorin assay was bought from Euroscreen Fast, Brussels (Euroscreen, Technical dossier, Human S1P1 (Edg1) receptor, DNA clone and CHO-K1 AequoScreen™ recombinant cell-line, catalog no: FAST-0197L, February 2010). Human-S1P1-Aequorin cells express mitochondrial targeted apo-Aequorin. Cells have to be loaded with coelanterazine, in order to reconstitute active Aequorin. After binding of agonists to the human S1P1 receptor the intracellular calcium concentration increases and binding of calcium to the apo-Aequorin/coelenterazine complex leads to an oxidation reaction of coelenterazine, which results in the production of apo-Aequorin, coelenteramide, CO$_2$ and light ($\square_{max}$ 469 nm). This luminescent response is dependent on the agonist concentration. Luminescence is measured using the MicroBeta Jet (Perkin Elmer). Agonistic effects of compounds are expressed as pEC$_{50}$. Compounds were tested at a 10 points half log concentration range, and 2 independent experiments were performed in single point's measurements.

In Vitro Functional Activity (Agonism) on Human S1P1 Receptors (Method B)

The CHO-K1-Human S1P1-c-AMP assay was performed at Euroscreen fast, Brussels (Euroscreen, Human S1P1 coupling G$_{i/o}$, (Edg1) receptor, catalog no: FAST-0197C, December 2009).

Recombinant CHO-K1 cells expressing human S1P1, grown to mid-log Phase in culture media without antibiotics, detached, centrifuged and re-suspended. For agonist testing cells are mixed with compound and Forskolin and incubated at room temperature. Cells are lyses and cAMP concentration are estimated, according to the manufacturer specification, With the HTRF kit from CIS-BIO International (cat no 62AM2PEB).

Agonistic effects of compounds are expressed as a percentage of the activity of the reference compound at its EC$_{100}$ concentration, EC$_{50}$ is calculated and results are reported as pEC$_{50}$. Compounds were tested at a 10 points half log concentration range duplicated in 1 experiment.

Pharmacological Data (Receptor Agonism) for Selected Compounds:

| Compound | S1P5 pEC$_{50}$ | S1P1$^A$ pEC$_{50}$ | S1P1$^B$ pEC$_{50}$ | S1P3 pEC$_{50}$ |
|---|---|---|---|---|
| 33 | 7.8 | | 7.0 | 5.5 |
| 35 | 8.3 | | 6.6 | 5.3 |
| 47 | 8.0 | | <5.5 | <5 |
| 53 | 7.9 | <4.5 | | <5 |
| 57 | 8.0 | | <5.5 | <5 |
| 73 | 8.2 | | 8.0 | 6.3 |
| 76 | 8.1 | | 6.6 | <5 |
| 77 | 8.4 | | 7.5 | 6.1 |
| 85 | 8.6 | | <5.5 | 6.3 |
| 89 | 8.2 | | 5.9 | <5.0 |
| 146 | 7.8 | | <5.5 | <5.0 |
| 156 | 8.4 | | 6.2 | 5.5 |
| 157 | 8.1 | | 6.2 | 5.3 |
| 175 | 8.3 | | <5.5 | 5.8 |
| 211 | 8.3 | | 6.1 | <5.0 |
| 227 | 8.5 | | 6.0 | <6.0 |
| 271 | 8.0 | | 6.2 | 5.4 |
| 277 (trans) | 8.5 | 5.2 | | <5.0 |
| 278 (cis) | 7.4 | <5 | | <5 |
| 283 | 7.7 | <4.5 | | <5 |
| 306 (trans) | 8.1 | <5 | | <5.0 |
| 307 (cis) | 7.3 | <5 | | <5.0 |

S1P1$^A$: determined using method A
S1P1$^B$: determined using method B

In Vivo Therapeutic Model; T-Maze

Age-related memory deficits occur in humans and rodents. Spontaneous alternation is the innate tendency of rodents to alternate free choices in a T-maze over a series of successive runs. This sequential procedure relies on working memory and is sensitive to various pharmacological manipulations affecting memory processes (Aging and the physiology of spatial memory. Barnes C. A. *Neurobiol. Aging* 1988:563-8; Dember W N, Fowler H. *Spontaneous alternation behavior. Psychol. Bull.* 1958, 55(6):412-427; Gerlai R. *A new continuous alternation task in T-maze detects hippocampal dysfunction in mice. A strain comparison and lesion study. Behav Brain Res* 1998 95(1):91-101).

For this study, male C57BL/6J mice of 2 months or 12 months old were used in the spontaneous alternation task in the T-maze. In short, mice were subjected to 1 session containing 15 trials, consisting of 1 "forced-choice" trial, followed by 14 "free-choice" trials. The animal was considered as entering one of the arms of the maze when all four paws are placed within this arm. A session is terminated and the animal is removed from the maze as soon as 14 free-choice trials have been performed or 15 min have elapsed, whatever event occurs first. The percentage of alternation over the 14 free-choice trials was determined for each mouse and was used as an index of working memory performance. A compound of the invention was administrated p.o. for 21 days prior the T-maze assay and on the day of the T-maze at t=−30 min. It was found that compounds of the invention at doses ranging from of 0.01-15 mg/kg/day reverse the age-related cognitive decline in the 12-month old C57BL6J mice with up to 100%. Thus, treated 12 month old mice were identical in their performance as 2 months old vehicle-treated mice. (See FIG. 1)

CONCLUSION

Compounds of the present invention have a positive effect on age-related cognitive decline.

The invention claimed is:

1. A method of treating age-related cognitive decline mediated by the S1P signaling pathway, the method comprising administering to a patient in need thereof a compound of formula (I), or a pharmaceutically acceptable salt, solvate, or hydrate thereof, or an N-oxide of any of the foregoing:

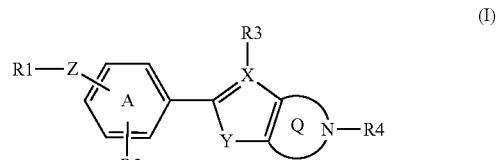

(I)

wherein

R1 is selected from the group consisting of:
  a cyano group;
  a (2-4C)alkenyl group, a (2-4C)alkynyl group, and a (1-4C)alkyl group, wherein each group is optionally substituted with a substituent independently selected from the group consisting of CN and at least one fluoro atom;
  a (3-6C)cycloalkyl group, a (4-6C)cycloalkenyl group, and a (8-10C)bicyclic group, wherein each group is optionally substituted with a substituent selected from the group consisting of a halogen atom and a (1-4C)alkyl group optionally substituted with at least one fluoro atom;
  a phenyl group, a biphenyl group, naphthyl group, wherein each group is optionally substituted with at least one substituent independently selected from the group consisting of halogen, cyano, (1-4C)alkyl optionally substituted with at least one halogen atom, (1-4C)alkoxy optionally substituted with at least one halogen atom, amino, dimethylamino, and (3-6C)cycloalkyl optionally substituted with a phenyl group wherein the phenyl group is optionally substituted with a substituent selected from the group consisting of (1-4C)alkyl and a halogen atom; and
  a phenyl group substituted with a group selected from the group consisting of a phenoxy group, a benzyl group, a benzyloxy group, a phenylethyl group, and a monocyclic heterocycle group, wherein each group is optionally substituted with (1-4C)alkyl;

Z is a —W—(C$_n$-alkylene)-T- group; wherein
  W is attached to R1 and selected from the group consisting of a bond, —O—, —CO—, —S—, —SO—, —SO$_2$—, —NH—, —CH=CH—, —C(CF$_3$)=CH—, —C≡C—, —CH$_2$—O—, —O—CO—, —CO—C—, —CO—NH—, —NH—CO—, and a trans-cyclopropylene;
  n is an integer from 0 to 10; and
  T is attached to the phenylene/pyridyl moiety and selected from the group consisting of a bond, —O—, —S—, —SO—, —SO$_2$—, —NH—, —CO—, —C=C—, —C≡C—, and a trans-cyclopropylene;

R2 is selected from H and at least one substituent independently selected from cyano, halogen, (1-4C)alkyl optionally substituted with at least one halogen atom, and (1-4C)alkoxy optionally substituted with at least one halogen atom;

ring structure A optionally contains a nitrogen atom;

X is selected from the group consisting of C and N;

wherein if X is C, R3 is selected from the group consisting of H and (1-4C)alkyl, and if X is N, R3 is not present;
Y is selected from the group consisting of NH, O, and S;
Structure Q is selected from the group consisting of a 5-, 6- and 7-membered cyclic amine;
and
R4 is selected from the group consisting of:
a (1-4C)alkylene-R5 group wherein at least one carbon atom in the alkylene group may independently be substituted with a substituent selected from the group consisting of at least one halogen atom and a $(CH_2)_2$ to form a cyclopropyl moiety; and
(3-6C)cycloalkylene-R5, —$CH_2$—(3-6C)cycloalkylene-R5, (3-6C)cycloalkylene-$CH_2$—R5, and —CO—$CH_2$—R5, wherein R5 is selected from the group consisting of —OH, —$PO_3H_2$, —$OPO_3H_2$, —COOH, —COO(1-4C)alkyl, and tetrazol-5-yl.

2. The method of claim 1, wherein
R1 is selected from the group consisting of:
a (3-6C)cycloalkyl group and a (8-10C)bicyclic group, wherein the group is optionally substituted with a substituent selected from the group consisting of a halogen atom, and a (1-4C)alkyl; and a phenyl group wherein the phenyl group is optionally substituted with at least one substituent independently selected from the group consisting of a halogen atom, cyano, (1-4C)alkyl, (1-4C)alkoxy, a trifluoromethyl, and a trifluoromethoxy;
W is selected from the group consisting of a bond, —O—, —CO—, —S—, —SO—, —$SO_2$—, —NH—, —CH=CH—, —C≡C—, and a trans-cyclopropylene;
n is an integer from 0 to 4; and
R2 is selected from the group consisting of H and at least one substituent independently selected from the group consisting of a halogen atom, (1-4C)alkyl optionally substituted with at least one fluoro atom, and (1-4C)alkoxy optionally substituted with at least one fluoro atom.

3. The method of claim 1, wherein the compound has the structure (Ia)

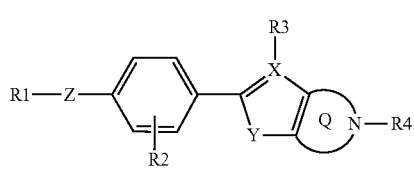

(Ia)

4. The method of claim 1, wherein the compound has the structure (1b)

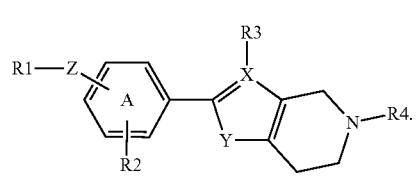

(Ib)

5. The method of claim 1, wherein Y is O.
6. The method of claim 1, wherein R4 is selected from the group consisting of —$(CH_2)_2$—COOH, —$(CH_2)_3$—COOH, —$CH_2$—$CHCH_3$—COOH, —$CH_2$—$C(CH_3)_2$—COOH, —$CHCH_3$—$CH_2$—COOH, —$CH_2$—$CF_2$—COOH, and 1,3-cyclobutylene-COOH.

7. The method of claim 1, wherein R1 is a phenyl group optionally substituted with at least one substituent independently selected from the group consisting of halogen, cyano, (1-4C)alkyl optionally substituted with at least one halogen atom, (1-4C)alkoxy optionally substituted with at least one halogen atom, amino, dimethylamino, and (3-6C)cycloalkyl optionally substituted with a phenyl group, wherein the phenyl group is optionally substituted with a substituent selected from the group consisting of (1-4C)alkyl and a halogen atom.

8. The method of claim 7, wherein R1 is a phenyl group optionally substituted with at least one substituent independently selected from the group consisting of a halogen atom, cyano, (1-4C)alkyl, (1-4C)alkoxy, a trifluoromethyl, and a trifluoromethoxy.

9. The method of claim 1, wherein Z is —$CH_2O$—.
10. The method of claim 1, wherein X is N.
11. The method of claim 1, wherein the compound is selected from the group consisting of:
3-{2-[4-(2-Fluoro-benzyloxy)-phenyl]-6,7-dihydro-4H-furo[3,2-c]pyridine-5-yl}-propionic acid;
3-{2-[4-(4-Chloro-benzyloxy)-phenyl]-6,7-dihydro-4H-furo[3,2-c]pyridine-5-yl}-2-methyl-propionic acid;
3-{2-[4-Benzyloxy-phenyl]-6,7-dihydro-4H-furo[3,2-c]pyridine-5-yl}-butyric acid;
4-{2-[4-(2-Fluoro-benzyloxy)-phenyl]-6,7-dihydro-4H-furo[3,2-c]pyridine-5-yl}-butyric acid;
4-{2-[4-(2-Fluoro-benzyloxy)-2-fluoro-phenyl]-6,7-dihydro-4H-furo[3,2-c]pyridine-5-yl}-butyric acid;
3-{2-[4-(Benzyloxy)-phenyl)]-6,7-dihydro-H-oxazolo[4,5-c]pyridine-5-yl}-propionic acid;
4-{2-[4-(2,3-Difluoro-benzyloxy)-phenyl)]-6,7-dihydro-H-oxazolo[4,5-c]pyridine-5-yl}-butyric acid;
4-{2-[4-Benzyloxy-phenyl]-6,7-dihydro-H-oxazolo[4,5-c]pyridine-5-yl}-butyric acid;
4-{2-[4-(4-Trifluoromethyl-benzyloxy)-2-fluoro-phenyl]-6,7-dihydro-H-oxazolo[4,5-c]pyridine-5-yl}-butyric acid;
4-{2-[4-(2-Fluoro-benzyloxy)-2-methyl-phenyl]-6,7-dihydro-H-oxazolo[4,5-c]pyridine-5-yl}-butyric acid;
4-{2-[4-(3,4-Dichloro-benzyloxy)-2-fluoro-phenyl]-6,7-dihydro-H-oxazolo[4,5-c]pyridine-5-yl}-butyric acid;
4-{2-[4-(2-Fluoro-benzyloxy)-3-chloro-phenyl]-6,7-dihydro-H-oxazolo[4,5-c]pyridine-5-yl}-butyric acid;
4-{2-[4-(4-Chloro-benzyloxy)-3-fluoro-phenyl]-6,7-dihydro-H-oxazolo[4,5-c]pyridine-5-yl}-butyric acid;
3-[2-(4-Benzyloxy-phenyl)-6,7-dihydro-H-oxazolo[4,5-c]pyridine-5-yl]-2-methyl-propionic acid;
3-{2-[4-(4-Trifluoromethyl-benzyloxy)-phenyl]-6,7-dihydro-H-oxazolo[4,5-c]pyridine-5-yl}-2-methyl-propionic acid;
3-{2-[4-(4-Chloro-benzyloxy)-phenyl]-6,7-dihydro-H-oxazolo[4,5-c]pyridine-5-yl}-2-methyl-propionic acid;
3-{2-[4-(4-2,3-Difluoro-benzyloxy)-phenyl]-6,7-dihydro-H-oxazolo[4,5-c]pyridine-5-yl}-butyric acid;
3-{2-[4-(4-Trifluoromethyl-benzyloxy)-2-fluoro-phenyl]-6,7-dihydro-H-oxazolo[4,5-c]pyridine-5-yl}-2-methyl-propionic acid;
Cis and trans 3-{2-[4-(4-Trifluoromethoxybenzyloxy)-phenyl]-6,7-dihydro-H-oxazolo[4,5-c]pyridine-5-yl}-cyclobutane carboxylic acid;
Cis and trans 3-{2-[4-(3,4-Difluorobenzyloxy)-phenyl]-6,7-dihydro-H-oxazolo[4,5-c]pyridine-5-yl}-cyclobutane carboxylic acid;

3-[2-(4-(2-Fluoro-benzyloxy)-phenyl)-6,7-dihydro-4H-thiazolo[5,4-c]pyridine-5-yl]-propionic acid;
4-{2-[4-(3,5-Difluoro-benzyloxy)-phenyl]-6,7-dihydro-4H-thiazolo-[4,5c]-pyridin-5-yl}-butyric acid;
2-{2-[4-(3,5-Difluoro-benzyloxy)-phenyl]-6,7-dihydro-H-oxazolo[4,5-c]pyridine-5-yl}-acetic acid;
2-{2-[4-(3,5-Difluoro-benzyloxy)-phenyl]-6,7-dihydro-H-oxazolo[4,5-c]pyridine-5-yl}-propionic acid;
3-{2-[4-(3,5-Difluoro-benzyloxy)-phenyl]-6,7-dihydro-4H-oxazolo[4,5-c]-pyridin-5-yl}-cyclopentane carboxylic acid;
4-{2-[4-(2,3-Difluoro-benzyloxy)-2-methyl-phenyl]-6,7-dihydro-4H-oxazolo-[4,5c]-pyridin-5-yl}-pentanoic acid;
4-{2-[4-(2,3-Difluoro-benzyloxy)-2-methyl-phenyl]-6,7-dihydro-4H-oxazolo[4,5-c]-pyridin-5-yl}-2-methylbutyric acid;
4-{2-[4-(2,3-Difluoro-benzyloxy)-2-methyl-phenyl]-6,7-dihydro-4H-oxazolo-[4,5c]-pyridin-5-yl}-3-methylbutyric acid;
3-{2-[4-(2-phenyl-cyclopropyl)-3-fluoro-phenyl]-6,7-dihydro-4H-oxazolo-[4,5-c]-pyridin-5-yl}-cyclobutane carboxylic acid;
4-(2-{4-[2-(3,5-Difluoro-phenyl)-vinyl]-phenyl}-6,7-dihydro-4H-oxazolo-[4,5c]-pyridin-5-yl)-butyric acid; and 4-(2-{4-[2-(3,5-Difluoro-phenyl)-ethyl]-phenyl}-6,7-dihydro-4H-oxazolo[4,5c]pyridin-5-yl)-butyric acid;
or a pharmaceutically acceptable salt, solvate, or hydrate thereof, or an N-oxide of any of the foregoing.

12. A method of treating Alzheimer's disease mediated by the S1P signaling pathway, the method comprising administering to a patient in need thereof a compound of formula (I), or a pharmaceutically acceptable salt, solvate, or hydrate thereof, or an N-oxide of any of the foregoing:

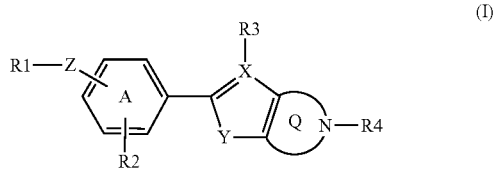

(I)

wherein
R1 is selected from the group consisting of:
a cyano group;
a (2-4C)alkenyl group, a (2-4C)alkynyl group, and a (1-4C)alkyl group, wherein each group is optionally substituted with a substituent independently selected from the group consisting of CN and at least one fluoro atom;
a (3-6C)cycloalkyl group, a (4-6C)cycloalkenyl group, and a (8-10C)bicyclic group, wherein each group is optionally substituted with a substituent selected from the group consisting of a halogen atom and a (1-4C)alkyl group optionally substituted with at least one fluoro atom;
a phenyl group, a biphenyl group, a naphthyl group, wherein each group is optionally substituted with at least one substituent independently selected from the group consisting of halogen, cyano, (1-4C)alkyl optionally substituted with at least one halogen atom, (1-4C)alkoxy optionally substituted with at least one halogen atom, amino, dimethylamino, and (3-6C)cycloalkyl optionally substituted with a phenyl group, wherein the phenyl group is optionally substituted with a substituent selected from the group consisting of (1-4C)alkyl and a halogen atom; and
a phenyl group substituted with a group selected from the group consisting of a phenoxy group, a benzyl group, a benzyloxy group, a phenylethyl group, and a monocyclic heterocycle group, wherein each group is optionally substituted with (1-4C)alkyl;

Z is a —W—($C_n$-alkylene)-T- group; wherein
W is attached to R1 and selected from the group consisting of a bond, —O—, —CO—, S, —SO—, —$SO_2$—, —NH—, —CH=CH—, —C($CF_3$)=CH—, —C≡C—, —$CH_2$—O—, —O—CO—, —CO—O—, —CO—NH—, —NH—CO—, and a trans-cyclopropylene;
n is an integer from 0 to 10; and
T is attached to the phenylene/pyridyl moiety and selected from the group consisting of a bond, —O—, —S—, —SO—, —$SO_2$—, —NH—, —CO—, —C=C—, —C≡C—, and a trans-cyclopropylene;
R2 is selected from H and at least one substituent independently selected from cyano, halogen, (1-4C)alkyl optionally substituted with at least one halogen atom, and (1-4C)alkoxy optionally substituted with at least one halogen atom;
ring structure A optionally contains a nitrogen atom;
X is selected from the group consisting of C and N;
wherein if X is C, R3 is selected from the group consisting of H and (1-4C)alkyl, and if X is N, R3 is not present;
Y is selected from the group consisting of NH, O, and S;
Structure Q is selected from the group consisting of a 5-, 6- and 7-membered cyclic amine;
and
R4 is selected from the group consisting of:
a (1-4C)alkylene-R5 group wherein at least one carbon atom in the alkylene group may independently be substituted with a substituent selected from the group consisting of at least one halogen atom and a ($CH_2$)$_2$ to form a cyclopropyl moiety; and
(3-6C)cycloalkylene-R5, —$CH_2$—(3-6C)cycloalkylene-R5, (3-6C)cycloalkylene-$CH_2$—R5, and —CO—$CH_2$—R5, wherein R5 is selected from the group consisting of —OH, —$PO_3H_2$, —$OPO_3H_2$, —COOH, —COO(1-4C)alkyl, and tetrazol-5-yl.

13. The method of claim 12, wherein
R1 is selected from the group consisting of:
a (3-6C)cycloalkyl group and a (8-10C)bicyclic group, wherein the group is optionally substituted with a substituent selected from the group consisting of a halogen atom, and a (1-4C)alkyl; and a phenyl group wherein the phenyl group is optionally substituted with at least one substituent independently selected from the group consisting of a halogen atom, cyano, (1-4C)alkyl, (1-4C)alkoxy, a trifluoromethyl, and a trifluoromethoxy;
W is selected from the group consisting of a bond, —O—, —CO—, —S—, —SO—, —$SO_2$—, —NH—, —CH=CH—, —C≡C—, and a trans-cyclopropylene;
n is an integer from 0 to 4; and
R2 is selected from the group consisting of H and at least one substituent independently selected from the group consisting of a halogen atom, (1-4C)alkyl optionally substituted with at least one fluoro atom, and (1-4C) alkoxy optionally substituted with at least one fluoro atom.

14. The method of claim 12, wherein the compound has the structure (Ia)

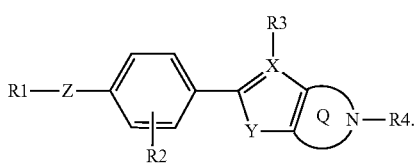

(Ia)

15. The method of claim 12, wherein the compound has the structure (Ib)

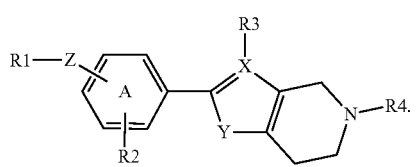

(Ib)

16. The method of claim 12, wherein Y is O.

17. The method of claim 12, wherein R4 is selected from the group consisting of —(CH$_2$)$_2$—COOH, —(CH$_2$)$_3$—COOH, —CH$_2$—CHCH$_3$—COOH, —CH$_2$—C(CH$_2$)$_2$—COOH, —CHCH$_3$—CH$_2$—COOH, —CH$_2$—CF$_2$—COOH, and 1,3-cyclobutylene-COOH.

18. The method of claim 12, wherein R1 is a phenyl group optionally substituted with at least one substituent independently selected from the group consisting of halogen, cyano, (1-4C)alkyl optionally substituted with at least one halogen atom, (1-4C)alkoxy optionally substituted with at least one halogen atom, amino, dimethylamino, and (3-6C)cycloalkyl optionally substituted with a phenyl group, wherein the phenyl group is optionally substituted with a substituent selected from the group consisting of (1-4C)alkyl and a halogen atom.

19. The method of claim 18, wherein R1 is a phenyl group optionally substituted with at least one substituent independently selected from the group consisting of a halogen atom, cyano, (1-4C)alkyl, (1-4C)alkoxy, a trifluoromethyl, and a trifluoromethoxy.

20. The method of claim 12, wherein Z is —CH$_2$O—.

21. The method of claim 12, wherein X is N.

22. The method of claim 12, wherein the compound is selected from the group consisting of:

3-{2-[4-(2-Fluoro-benzyloxy)-phenyl]-6,7-dihydro-4H-furo[3,2-c]pyridine-5-yl}-propionic acid;
3-{2-[4-(4-Chloro-benzyloxy)-phenyl]-6,7-dihydro-4H-furo[3,2-c]pyridine-5-yl}-2-methyl-propionic acid;
3-{2-[4-Benzyloxy-phenyl]-6,7-dihydro-4H-furo[3,2-c]pyridine-5-yl}-butyric acid;
4-{2-[4-(2-Fluoro-benzyloxy)-phenyl]-6,7-dihydro-4H-furo[3,2-c]pyridine-5-yl}-butyric acid;
4-{2-[4-(2-Fluoro-benzyloxy)-2-fluoro-phenyl]-6,7-dihydro-4H-furo[3,2-c]pyridine-5-yl}-butyric acid;
3-{2-[4-(Benzyloxy)-phenyl)]-6,7-dihydro-H-oxazolo[4,5-c]pyridine-5-yl}-propionic acid;
4-{2-[4-(2,3-Difluoro-benzyloxy)-phenyl)]-6,7-dihydro-H-oxazolo[4,5-c]pyridine-5-yl}-butyric acid;
4-{2-[4-Benzyloxy-phenyl]-6,7-dihydro-H-oxazolo[4,5-c]pyridine-5-yl}-butyric acid;
4-{2-[4-(4-Trifluoromethyl-benzyloxy)-2-fluoro-phenyl]-6,7-dihydro-H-oxazolo[4,5-c]pyridine-5-yl}-butyric acid;
4-{2-[4-(2-Fluoro-benzyloxy)-2-methyl-phenyl]-6,7-dihydro-H-oxazolo[4,5-c]pyridine-5-yl}-butyric acid;
4-{2-[4-(3,4-Dichloro-benzyloxy)-2-fluoro-phenyl]-6,7-dihydro-H-oxazolo[4,5-c]pyridine-5-yl}-butyric acid;
4-{2-[4-(2-Fluoro-benzyloxy)-3-chloro-phenyl]-6,7-dihydro-H-oxazolo[4,5-c]pyridine-5-yl}-butyric acid;
4-{2-[4-(4-Chloro-benzyloxy)-3-fluoro-phenyl]-6,7-dihydro-H-oxazolo[4,5-c]pyridine-5-yl}-butyric acid;
3-[2-(4-Benzyloxy-phenyl)-6,7-dihydro-H-oxazolo[4,5-c]pyridine-5-yl]-2-methyl-propionic acid;
3-{2-[4-(4-Trifluoromethyl-benzyloxy)-phenyl]-6,7-dihydro-H-oxazolo[4,5-c]pyridine-5-yl}-2-methyl-propionic acid;
3-{2-[4-(4-Chloro-benzyloxy)-phenyl]-6,7-dihydro-H-oxazolo[4,5-c]pyridine-5-yl]-2-methyl-propionic acid;
3-{2-[4-(4-2,3-Difluoro-benzyloxy)-phenyl]-6,7-dihydro-H-oxazolo[4,5-c]pyridine-5-yl}-butyric acid;
3-{2-[4-(4-Trifluoromethyl-benzyloxy)-2-fluoro-phenyl]-6,7-dihydro-H-oxazolo[4,5-c]pyridine-5-yl}-2-methyl-propionic acid;
Cis and trans 3-{2-[4-(4-Trifluoromethoxybenzyloxy)-phenyl]-6,7-dihydro-H-oxazolo[4,5-c]pyridine-5-yl}-cyclobutane carboxylic acid;
Cis and trans 3-{2-[4-(3,4-Difluorobenzyloxy)-phenyl]-6,7-dihydro-H-oxazolo[4,5-c]pyridine-5-yl}-cyclobutane carboxylic acid;
3-[2-(4-(2-Fluoro-benzyloxy)-phenyl)-6,7-dihydro-4H-thiazolo[5,4-c]pyridine-5-yl]-propionic acid;
4-{2-[4-(3,5-Difluoro-benzyloxy)-phenyl]-6,7-dihydro-4H-thiazolo-[4,5c]-pyridin-5-yl}-butyric acid;
2-{2-[4-(3,5-Difluoro-benzyloxy)-phenyl]-6,7-dihydro-H-oxazolo[4,5-c]pyridine-5-yl}-acetic acid;
2-{2-[4-(3,5-Difluoro-benzyloxy)-phenyl]-6,7-dihydro-H-oxazolo[4,5-c]pyridine-5-yl}-propionic acid;
3-{2-[4-(3,5-Difluoro-benzyloxy)-phenyl]-6,7-dihydro-4H-oxazolo[4,5-c]-pyridin-5-yl}-cyclopentane carboxylic acid;
4-{2-[4-(2,3-Difluoro-benzyloxy)-2-methyl-phenyl]-6,7-dihydro-4H-oxazolo-[4,5c]-pyridin-5-yl}-pentanoic acid;
4-{2-[4-(2,3-Difluoro-benzyloxy)-2-methyl-phenyl]-6,7-dihydro-4H-oxazolo[4,5-c]-pyridin-5-yl}-2-methyl-butyric acid;
4-{2-[4-(2,3-Difluoro-benzyloxy)-2-methyl-phenyl]-6,7-dihydro-4H-oxazolo-[4,5c]-pyridin-5-yl}-3-methyl-butyric acid;
3-{2-[4-(2-phenyl-cyclopropyl)-3-fluoro-phenyl]-6,7-dihydro-4H-oxazolo-[4,5-c]-pyridin-5-yl}-cyclobutane carboxylic acid;
4-(2-{4-[2-(3,5-Difluoro-phenyl)-vinyl]-phenyl}-6,7-dihydro-4H-oxazolo-[4,5c]-pyridin-5-yl)-butyric acid; and
4-(2-{4-[2-(3,5-Difluoro-phenyl)-ethyl]-phenyl}-6,7-dihydro-4H-oxazolo[4,5c]pyridin-5-yl)-butyric acid;
or a pharmaceutically acceptable salt, solvate, or hydrate thereof, or an N-oxide of any of the foregoing.

* * * * *

UNITED STATES PATENT AND TRADEMARK OFFICE
CERTIFICATE OF CORRECTION

PATENT NO. : 9,096,612 B2
APPLICATION NO. : 14/019236
DATED : August 4, 2015
INVENTOR(S) : Pieter Smid et al.

It is certified that error appears in the above-identified patent and that said Letters Patent is hereby corrected as shown below:

IN THE SPECIFICATION

Column 8, line 25, delete "10 ul" and insert --10 μl--.

Column 8, line 27, delete "2.5 um" and insert --2.5 μm--.

Column 8, line 65, delete "50 ul" and insert --50 μl--.

Column 9, line 14, delete "2 ul" and insert --2 μl--.

Column 9, line 16, delete "2.5 ▢m" and insert --2.5 μm--.

Column 9, line 18, delete "2.7 ul" and insert --2.7 μl--.

Column 23, line 15, delete "4 eg" and insert --4 eq--.

Column 23, line 44, delete "1.05 eg" and insert --1.05 eq--.

Column 23, line 54, delete "1,8-diazabicyclo[5.4.0]undec-7-ene(3 eg)" and insert --1,8-diazabicyclo[5.4.0]undec-7-ene(3 eq)--.

Column 25, line 17, delete "5% ag. NaHCO3" and insert --5% aq. NaHCO3--.

Column 26, line 21, delete "1.05 eg" and insert --1.05 eq--.

Column 27, line 18, delete "4 eg" and insert --4 eq--.

Column 27, line 22, delete "2 eg" and insert --2 eq--.

Signed and Sealed this
Twenty-second Day of March, 2016

Michelle K. Lee
*Director of the United States Patent and Trademark Office*

IN THE SPECIFICATION

Column 27, line 42, delete "2.05 eg" and insert --2.05 eq--.

Column 29, line 30, delete "4 eg" and insert --4 eq--.

Column 29, line 35, delete "(2.5 eg)" and insert --(2.5 eq)--.

Column 29, line 60, delete "(1.05 eg)" and insert --(1.05 eq)--.

Column 30, line 49, delete "0.22 eg" and insert --0.22 eq--.

Column 32, line 50, delete "1.05 eg" and insert --1.05 eq--.

Column 37, line 33, delete "☐PPM" and insert --δ ppm--.

Column 37, line 48, delete "☐PPM" and insert --δ ppm--.

Column 39, line 28, delete "☐ ppm" and insert --δ ppm--.

Column 40, line 10, delete "☐☐ ppm" and insert --δ ppm--.

Column 40, line 21, delete "☐ ppm" and insert --δ ppm--.

Column 40, line 37, delete "☐ ppm" and insert --δ ppm--.

Column 40, line 50, delete "☐ ppm" and insert --δ ppm--.

Column 40, line 64, delete "☐ ppm" and insert --δ ppm--.

Column 41, line 11, delete "☐ ppm" and insert --δ ppm--.

Column 41, line 25, delete "☐ ppm" and insert --δ ppm--.

Column 42, line 45, delete "☐ ppm" and insert --δ ppm--.

Column 42, line 58, delete "☐ ppm" and insert --δ ppm--.

Column 42, line 63, delete "☐ PPM" and insert --δ ppm--.

Column 43, line 10, delete "☐ ppm" and insert --δ ppm--.

Column 43, line 15, delete "☐ PPM" and insert --δ ppm--.

CERTIFICATE OF CORRECTION (continued)
U.S. Pat. No. 9,096,612 B2

IN THE SPECIFICATION

Column 43, line 27, delete "□□ ppm" and insert --δ ppm--.

Column 43, line 38, delete "□ ppm" and insert --δ ppm--.

Column 44, line 62, delete "□ ppm" and insert --δ ppm--.

Column 44, line 67, delete "□ ppm" and insert --δ ppm--.

Column 45, line 13, delete "□ ppm" and insert --δ ppm--.

Column 45, line 20, delete "□ ppm" and insert --δ ppm--.

Column 46, line 55, delete "□ ppm" and insert --δ ppm--.

Column 47, line 41, delete "□ ppm" and insert --δ ppm--.

Column 48, line 2, delete "□ ppm" and insert --δ ppm--.

Column 48, line 26, delete "□ ppm" and insert --δ ppm--.

Column 49, line 12, delete "□ ppm" and insert --δ ppm--.

Column 49, line 48, delete "□ ppm" and insert --δ ppm--.

Column 50, line 12, delete "□ ppm" and insert --δ ppm--.

Column 50, line 64, delete "□ ppm" and insert --δ ppm--.

Column 51, line 32, delete "□ ppm" and insert --δ ppm--.

Column 51, line 54, delete "□ ppm" and insert --δ ppm--.

Column 52, line 23, delete "□ ppm" and insert --δ ppm--.

Column 52, line 29, delete "□ ppm" and insert --δ ppm--.

Column 52, line 47, delete "□ ppm" and insert --δ ppm--.

Column 55, line 30, delete "75 phenyl CH2O H C O H B -CH2-CH(CH3)-COOH 1,46".

Column 55, line 32, delete "77 4Cl-phenyl CH2O H C O H B -CH2-CH(CH3)- 1,56" and insert --77 4Cl-phenyl CH2O H C O H B -CH2-CH(CH3)-COOH 1,56--.

CERTIFICATE OF CORRECTION (continued)
U.S. Pat. No. 9,096,612 B2

IN THE SPECIFICATION

Column 55, line 33, delete "78 4Cl-phenyl CH2O H C O H B -CH2-C(CH3)2-COOH 1,76".

Column 59, line 16, delete "146 phenyl CH2O H N O  B -CH2-CH(CH3)- 1,48" and insert --146 phenyl CH2O H N O  B -CH2-CH(CH3)-COOH 1,48--.

Column 59, line 24, delete "154 2,3diF-phenyl CH2O H N O  B -CH2-CH(CH3)-COOH 1,32".

Column 59, line 25, delete "155 3,4diF-phenyl CH2O H N O  B -CH2-CH(CH3)-COOH 1,63".

Column 59, line 26, delete "156 4CF3-phenyl CH2O H N O  B -CH2-CH(CH3)- 1,82" and insert --156 4CF3-phenyl CH2O H N O  B -CH2-CH(CH3)-COOH 1,82--.

Column 59, line 27, delete "157 4Cl-phenyl CH2O H N O  B -CH2-CH(CH3)- 1,72" and insert --157 4Cl-phenyl CH2O H N O  B -CH2-CH(CH3)-COOH 1,72--.

Column 59, line 28, delete "158 2F-phenyl CH2O H N O  B -CH2-CH(CH3)- 1,44".

Column 65, line 18, delete "270 2,3diF-phenyl CH2O H N O  B -CH2-C[(CH2)2]- 1,56".

Column 67, line 5, delete "297 3,4diF-phenyl CH2O 2F N O  B -CH2-CH(CH3)- 1,47".

Column 67, line 8, delete "300 2,3diF-phenyl CH2O H N NH  B -CH2-CH(CH3)- 1,1".

Column 67, line 25, delete "317 2,4,6-triF- CH2O H N O  B -CH(CH3)-CH2-COOH 1,43".

Column 67, line 29, delete "321 2,6-diF,4Cl- CH2O H N O  B -CH(CH3)-CH2-COOH 1,52".

Column 67, line 34, delete "326 3,5diF-phenyl CH2O H N O  B -cyclobutyl-COOH 1,34" and insert --326 3,5diF-phenyl CH2O H N O  B -cyclobutyl-COOH (trans) 1,34--.

Column 67, line 36, delete "328 3,4diCl-phenyl CH2O H N O  B -cyclobutyl-COOH 1,45" and insert --328 3,4diCl-phenyl CH2O H N O  B -cyclobutyl-COOH (trans) 1,45--.

Column 69, line 1, delete "333 3F-phenyl CH2O H N O  B -CH2-CH(CH3)- 1,57".

Column 69, line 2, delete "334 3,5diF-phenyl CH2O H N O  B -CH2-CH(CH3)- 1,65".

Column 69, line 3, delete "335 2,5diF-phenyl CH2O H N O  B -CH2-CH(CH3)- 1,61".

Column 69, line 4, delete "336 2F,6Cl-phenyl CH2O H N O  B -CH2-CH(CH3)- 1,62".

Column 69, line 5, delete "337 2,4diF-phenyl CH2O H N O  B -CH2-CH(CH3)- 1,59".

CERTIFICATE OF CORRECTION (continued)
U.S. Pat. No. 9,096,612 B2

IN THE SPECIFICATION

Column 69, line 6, delete "338 4F-phenyl CH2O H N O B -CH2-CH(CH3)- 1,55".

Column 69, line 7, delete "339 2F,3Cl-phenyl CH2O H N O B -CH2-CH(CH3)- 1,7".

Column 69, line 8, delete "340 2,4,6triF-phenyl CH2O H N O B -CH2-CH(CH3)- 1,6".

Column 69, line 9, delete "341 2,6diF,4Cl-phenyl CH2O H N O B -CH2-CH(CH3)- #".

Column 69, line 10, delete "342 2,3diCl-phenyl CH2O H N O B -CH2-CH(CH3)- #".

Column 69, line 11, delete "343 2Cl-phenyl CH2O H N O B -CH2-CH(CH3)- #".

Column 69, line 12, delete "344 2F,4Cl-phenyl CH2O H N O B -CH2-CH(CH3)- #".

Column 69, line 13, delete "345 2Cl, 4F-phenyl CH2O H N O B -CH2-CH(CH3)- #".

Column 69, line 14, delete "346 3F,4Cl-phenyl CH2O H N O B -CH2-CH(CH3)- #".

Column 69, line 15, delete "347 2,6diCl-phenyl CH2O H N O B -CH2-CH(CH3)- 1,71".

Column 69, line 16, delete "348 3Cl,5F-phenyl CH2O H N O B -CH2-CH(CH3)- 1,76".

Column 69, line 19, delete "351 phenyl CH2O 3 CF3 N O B -CH2-CH(CH3)- 1.59".

Column 69, line 21, delete "353 3,5-diCl-phenyl CH2O H N O B -CH2-CH(CH3)- #".

Column 69, line 23, delete "355 3,4-diCl-phenyl CH2O H N O B -CH2-CH(CH3)- #)".

Column 69, line 24, delete "356 2,4-diCl-phenyl CH2O H N O B -CH2-CH(CH3)- #".

Column 69, line 26, delete "358 3,4-diF-phenyl CH2O 3Cl N O B -CH2-CH(CH3)- 1.58".

Column 69, line 28, delete "360 3,4-diCl-phenyl CH2O 3Cl N O B -CH2-CH(CH3)- 1.73".

Column 69, line 30, delete "362 2,4,6-triF- CH2O H N O B -(CH2)2-COOH 1.36".

Column 69, line 36, delete "368 2,6-diF, 4Cl-phenyl CH2O H N O B -(CH2)2-COOH 1.45".

Column 69, line 39, delete "371 4-Cl-phenyl CH2O 3CF3 N O B -CH2-CH(CH3)- 1.67".

Column 69, line 40, delete "372 3,4-diCl-phenyl CH2O 3CF3 N O B -CH2-CH(CH3)- 1.78".

CERTIFICATE OF CORRECTION (continued)
U.S. Pat. No. 9,096,612 B2

IN THE SPECIFICATION

Column 71, line 1, delete "373 3,4-diF-phenyl CH2O 3CF3 N O  B -CH2-CH(CH3)- 1.61".

Column 71, line 2, delete "374 3,4-diF-phenyl CH2O 2CF3 N O  B -CH2-CH(CH3)- 1.61".

Column 71, line 3, delete "375 4Cl-phenyl CH2O 2CF3 N O  B -CH2-CH(CH3)- 1.68".

Column 71, line 4, delete "376 3,5-diF-phenyl CH2O 2CF3 N O  B -CH2-CH(CH3)- 1.61".

Column 71, line 5, delete "377 4 CF3-phenyl CH2O 2CF3 N O  B -CH2-CH(CH3)- 1.72".

Column 71, line 6, delete "378 4 CF3-phenyl CH2O 3CF3 N O  B -CH2-CH(CH3)- 1.72".

Column 71, line 10, delete "382 3,4-diF-phenyl CH2O 2Me N O  B -CH2-CH(CH3)- 1.5".

Column 71, line 11, delete "383 3,5-diF-phenyl CH2O 2Me N O  B -CH2-CH(CH3)-COOH 1.52".

Column 71, line 12, delete "384 4CF3-phenyl CH2O 2Me N O  B -CH2-CH(CH3)- 1.62".

Column 71, line 13, delete "385 2,3-diF-phenyl CH2O 2Me N O  B -CH2-CHCH3- 1.48".

Column 71, line 14, delete "386 3,4-diCl-phenyl CH2O 2Me N O  B -CH2-CH(CH3)- 1.66".

Column 71, line 15, delete "387 4Cl-phenyl CH2O 2Me N O  B -CH2-CH(CH3)- 1.57".

Column 71, line 16, delete "388 3,5-diF-phenyl CH2O 3CF3 N O  B -CH2-CH(CH3)- 1.62".

Column 71, line 17, delete "389 2,3-diF-phenyl CH2O 3CF3 N O  B -CH2-CH(CH3)- 1.57".

Column 71, line 19, delete "391 4Cl-phenyl CH2O 3Cl N O  B -CH2-CH(CH3)- 1.6".

Column 71, line 31, delete "403 3,4-diF-phenyl CH2O H N O  B -CH(CH3)-(CH2)2- #".

Column 71, line 32, delete "404 4Cl-phenyl CH2O 2Me N O  B -CH(CH3)-(CH2)2- 1.42".

Column 71, line 33, delete "405 4CF3-phenyl CH2O 2Me N O  B -CH(CH3)-(CH2)2- 1.45".

Column 73, line 4, delete "417 2,3-diF-phenyl CH2O 3F N O  B -CH2-CH(CH3)- #".

Column 73, line 7, delete "420 3,5-diF-phenyl CH2O 3Me N O  B -CH2-CH(CH3)-COOH 1.66".

Column 73, line 15, delete "428 3,5-diF-phenyl CH2O 3Me N O  B cis cyclobutyl-COOH 1.39".

CERTIFICATE OF CORRECTION (continued)
U.S. Pat. No. 9,096,612 B2

IN THE SPECIFICATION

Column 73, line 17, delete "430 2,3-diF-phenyl CH2O 3Me N O  B cis cyclobutyl- 1.36".

Column 73, line 19, delete "432 3,5-diF-phenyl CH2O 2Me N O  B trans cyclobutyl-COOH 1.35".

Column 73, line 20, delete "433 3,5-diF-phenyl CH2O 2Me N O  B cis cyclobutyl- 1.35".

Column 73, line 22, delete "435 4-Cl-phenyl CH2O 2Me N O  B -CH2-CH(CH3)- 1.49".

Column 73, line 23, delete "436 4-CF3-phenyl CH2O 2Me N O  B -CH2-CH(CH3)- 1.53".

Column 73, line 24, delete "437 2,3-diF-phenyl CH2O 2Me N O  B -CH2-CH(CH3)- 1.42" and insert --437 2,3-diF-phenyl CH2O 2Me N O  B -CH2-CH(CH3)-CH2-COOH 1.42--.

Column 73, line 25, delete "438 3,4-diF-phenyl CH2O 2Me N O  B -CH2-CH(CH3)- 1.44".

Column 73, line 27, delete "440 2,3-diF-phenyl CH2O 3Me N O  B -CH2-CH(CH3)-COOH 1.5".

Column 73, line 36, delete "449 4-Cl-phenyl CH2O H N S  B -CH2-CH(CH3)- 1.52".

Column 73, line 37, delete "450 3,5-diF-phenyl CH2O H N S  B -CH2-CH(CH3)- 1.48".

Column 73, line 40, delete "453 3,5-diF-phenyl C=C H N O  B -CH2-CH(CH3)- 1.59".

Column 75, line 1, delete "454 3,5-diF-phenyl (CH2)2 H N O  B -CH2-CH(CH3)- 1.53".

Column 75, line 5, delete "458 phenyl cyclo-propyl 3F N O  B -CH2-CH(CH3)- 1.55".

Column 75, line 9, delete "462 phenyl cyclo-propyl 3F N O  B -CH2-CH(CH3)- 1.55".